(12) United States Patent
Conner et al.

(10) Patent No.: US 8,734,312 B2
(45) Date of Patent: May 27, 2014

(54) CONTROL PORTION OF AND DEVICE FOR REMOTELY CONTROLLING AN ARTICULATING SURGICAL INSTRUMENT

(75) Inventors: Craig Conner, Madison, WI (US); Mark Doyle, Del Mar, CA (US); David Gennrich, Fitchburg, WI (US); Curt Irwin, Madison, WI (US); Jose Jacquez, Spring Valley, CA (US); Corey Magers, Oceanside, CA (US); Brooke Skora, San Diego, CA (US)

(73) Assignee: Carefusion 2200, Inc., San Diego, CA (US)

( * ) Notice: Subject to any disclaimer, the term of this patent is extended or adjusted under 35 U.S.C. 154(b) by 775 days.

(21) Appl. No.: 12/869,717

(22) Filed: Aug. 26, 2010

(65) Prior Publication Data

US 2011/0152881 A1 Jun. 23, 2011

Related U.S. Application Data

(60) Provisional application No. 61/237,042, filed on Aug. 26, 2009.

(51) Int. Cl.
*A61B 17/00* (2006.01)
(52) U.S. Cl.
USPC ............................................. 600/1; 600/130

(58) Field of Classification Search
USPC .......... 606/1, 205, 130; 901/8, 14–18, 27, 32, 901/36, 37
See application file for complete search history.

(56) References Cited

U.S. PATENT DOCUMENTS

| 5,410,638 | A | * | 4/1995 | Colgate et al. ................ 700/264 |
| 6,016,607 | A | * | 1/2000 | Morimoto et al. ............. 33/1 M |
| 7,169,141 | B2 | * | 1/2007 | Brock et al. ...................... 606/1 |
| 2002/0128633 | A1 | | 9/2002 | Brock et al. |
| 2003/0013949 | A1 | | 1/2003 | Moll et al. |
| 2005/0090811 | A1 | | 4/2005 | Doyle et al. |
| 2006/0276775 | A1 | | 12/2006 | Rosenberg et al. |

* cited by examiner

*Primary Examiner* — Bill Thompson
*Assistant Examiner* — Boniface N Nganga
(74) *Attorney, Agent, or Firm* — Arent Fox LLP

(57) ABSTRACT

A remotely controlled surgical device control portion comprises a user moveable bi-directional trigger, a finger loop disposed within the trigger, and a flange coupled to the finger loop. The trigger is configured for receiving a motion input in opposing first and second directions. The motion input is for controlling an articulation motion of an articulating surgical instrument. The finger loop is configured for receiving the motion input in the form of a user squeezing the trigger in the first direction with at least one finger or pushing the trigger in the second direction with said at least one finger. The flange is configured for receiving the motion input in the form of pushing the trigger in the second direction with a thumb.

26 Claims, 53 Drawing Sheets

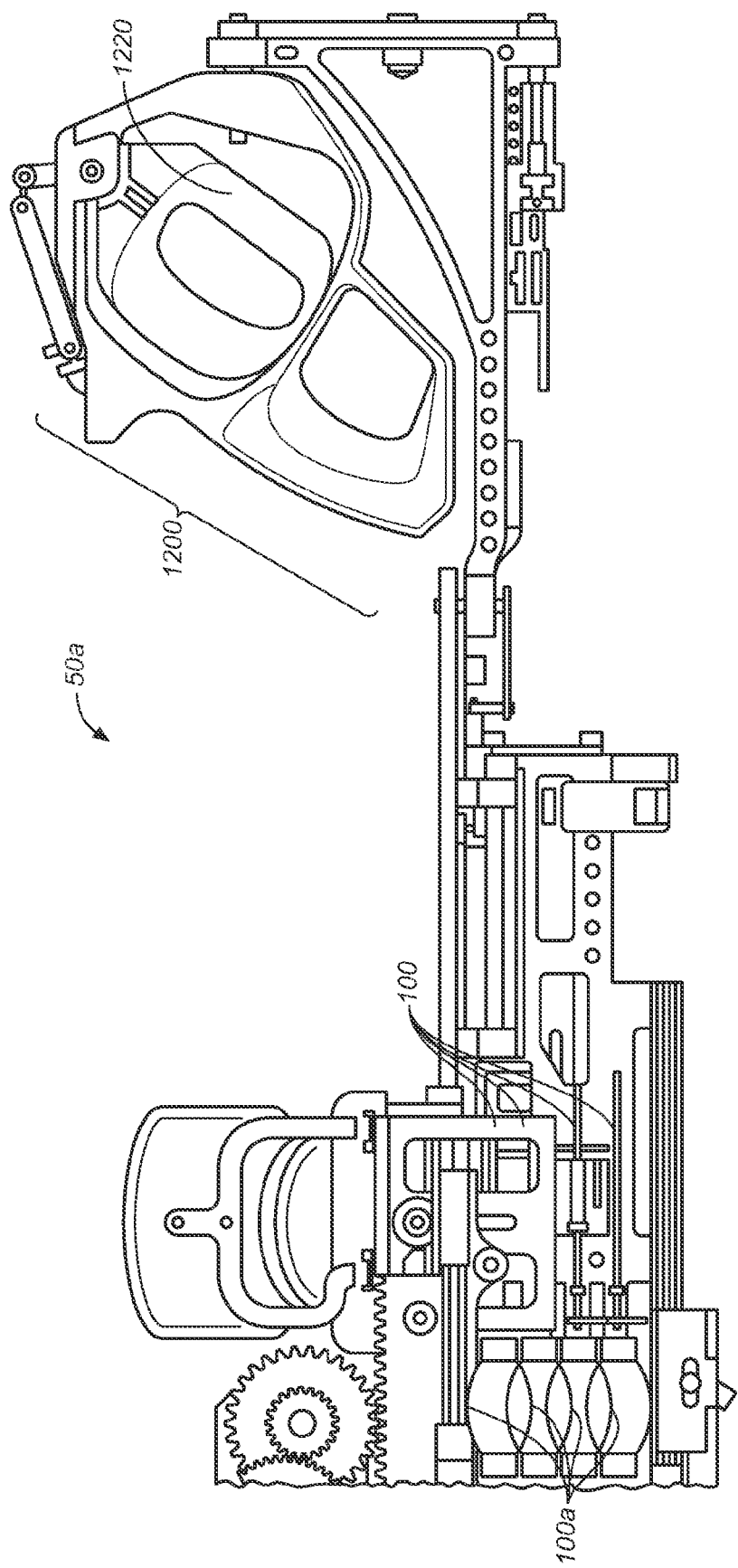

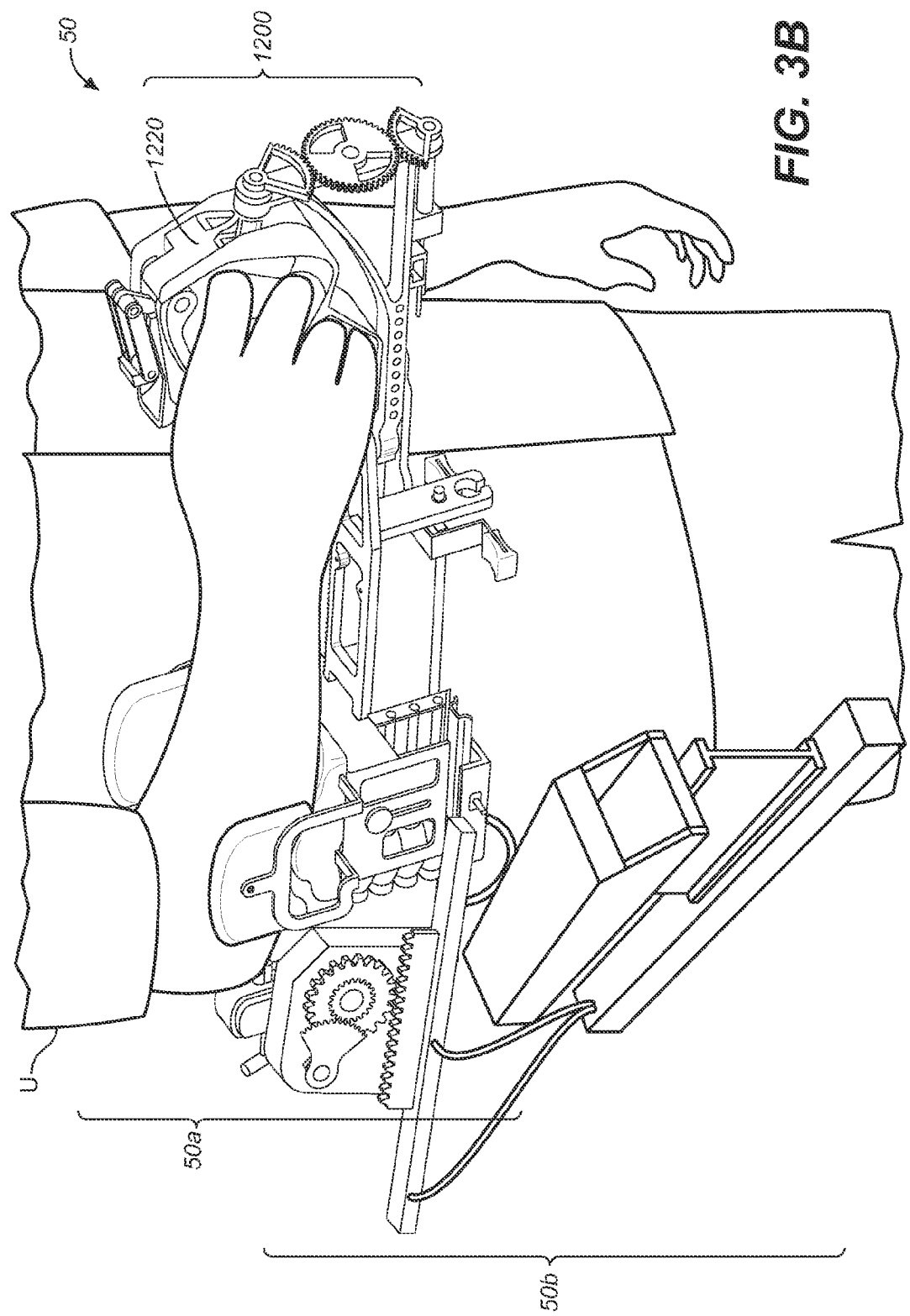

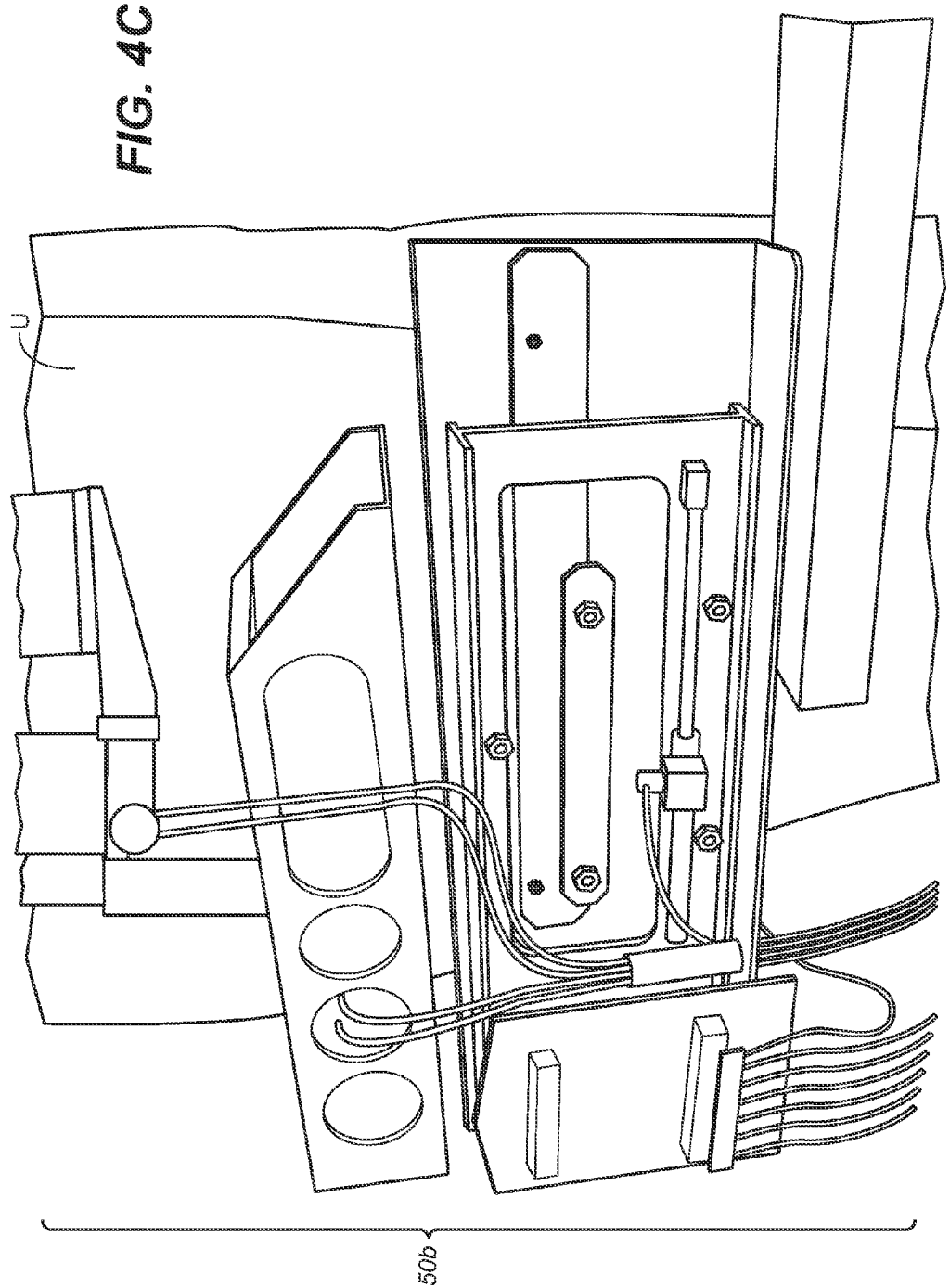

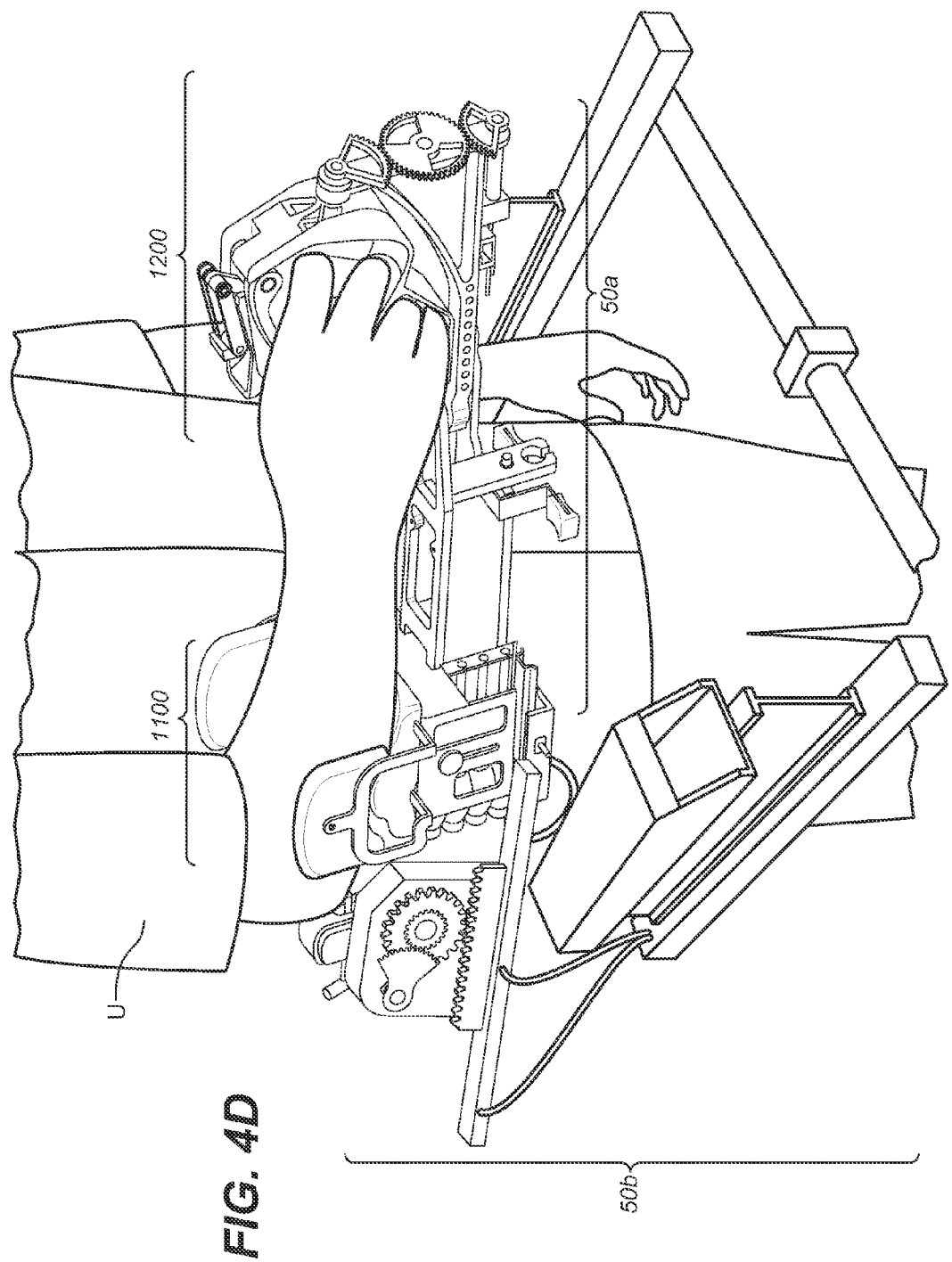

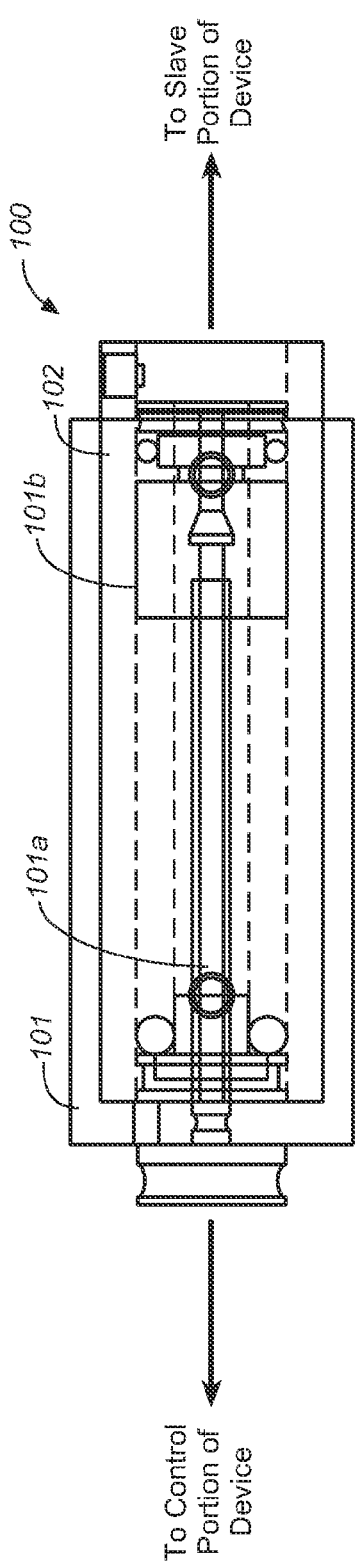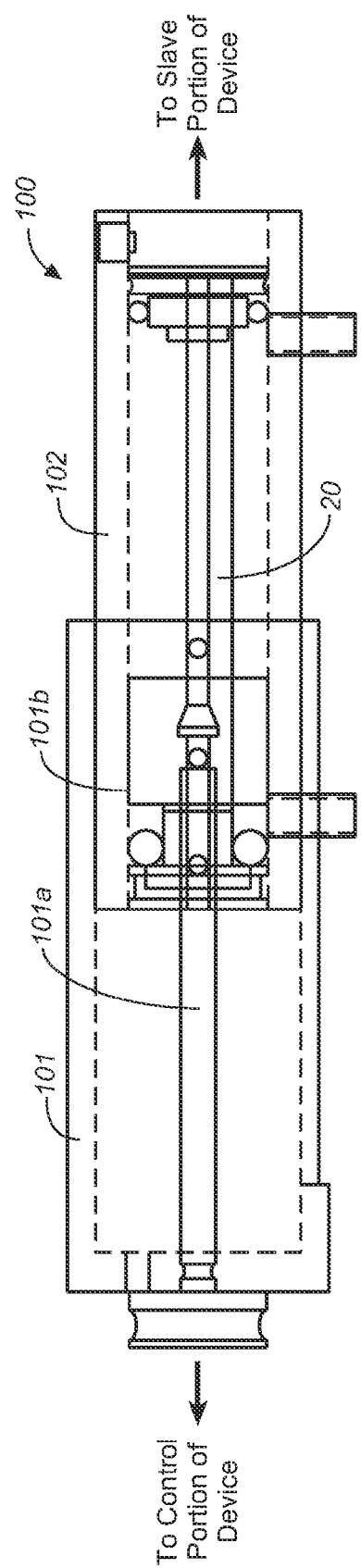
FIG. 5A
FIG. 5B

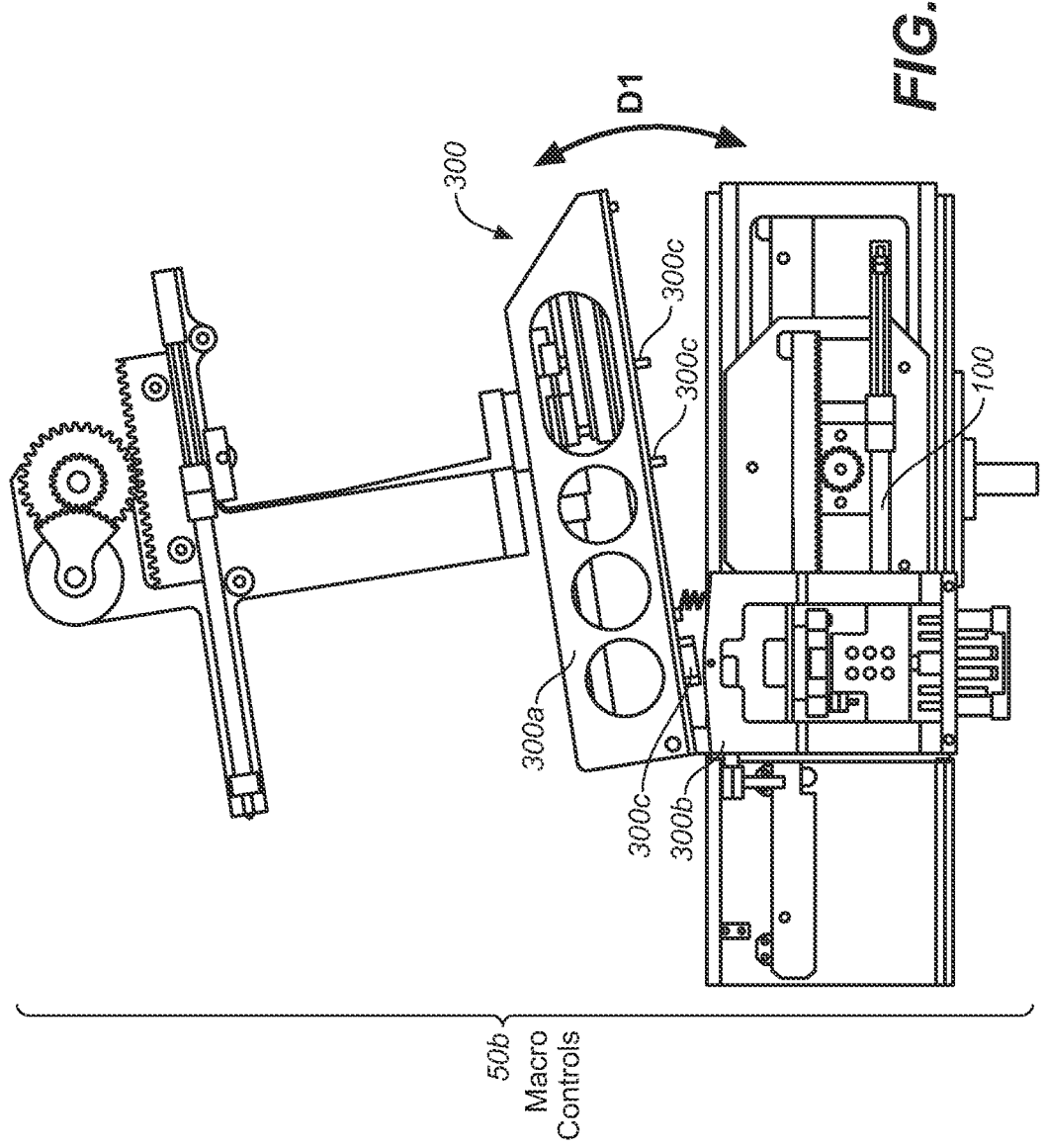

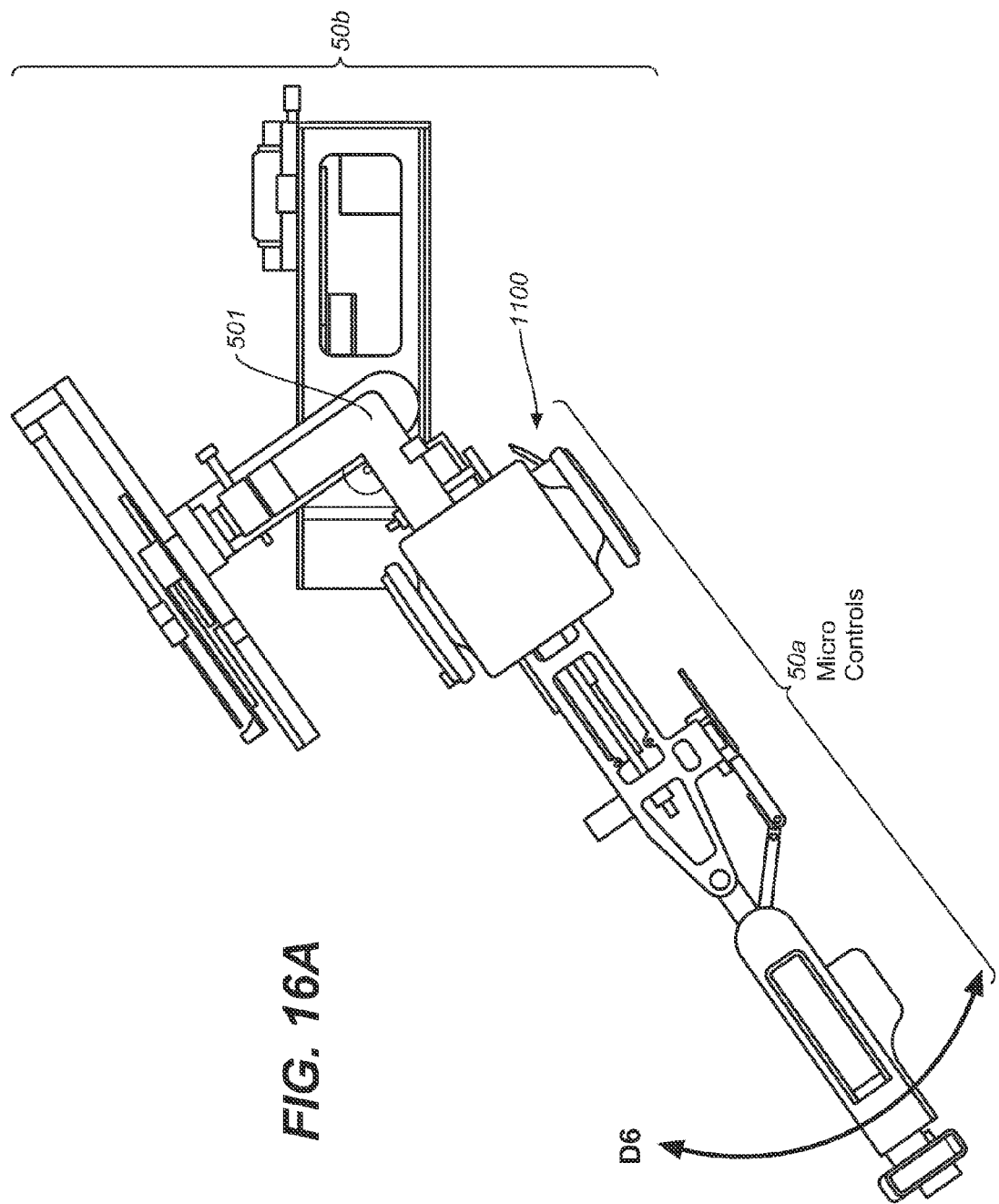

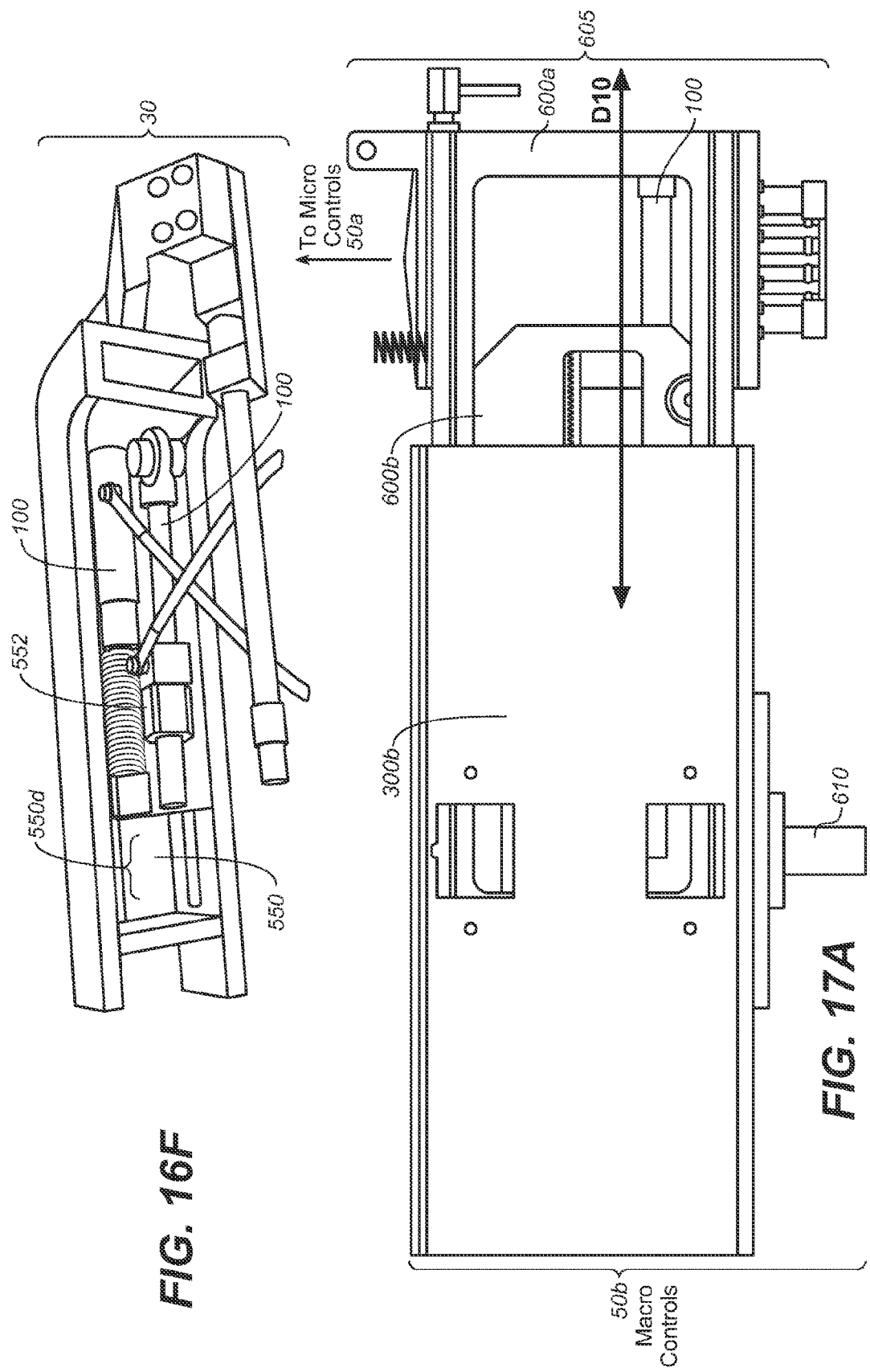

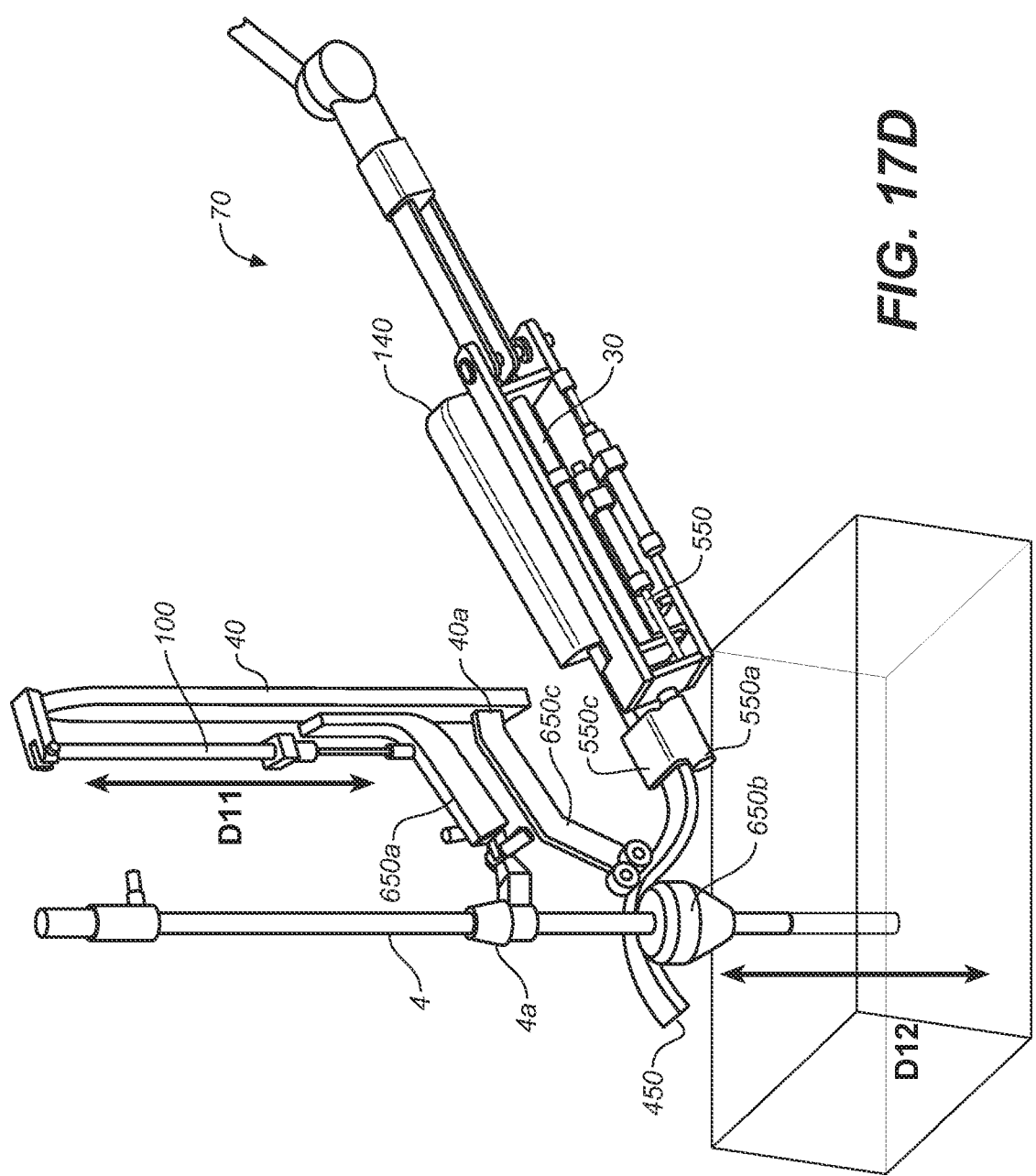

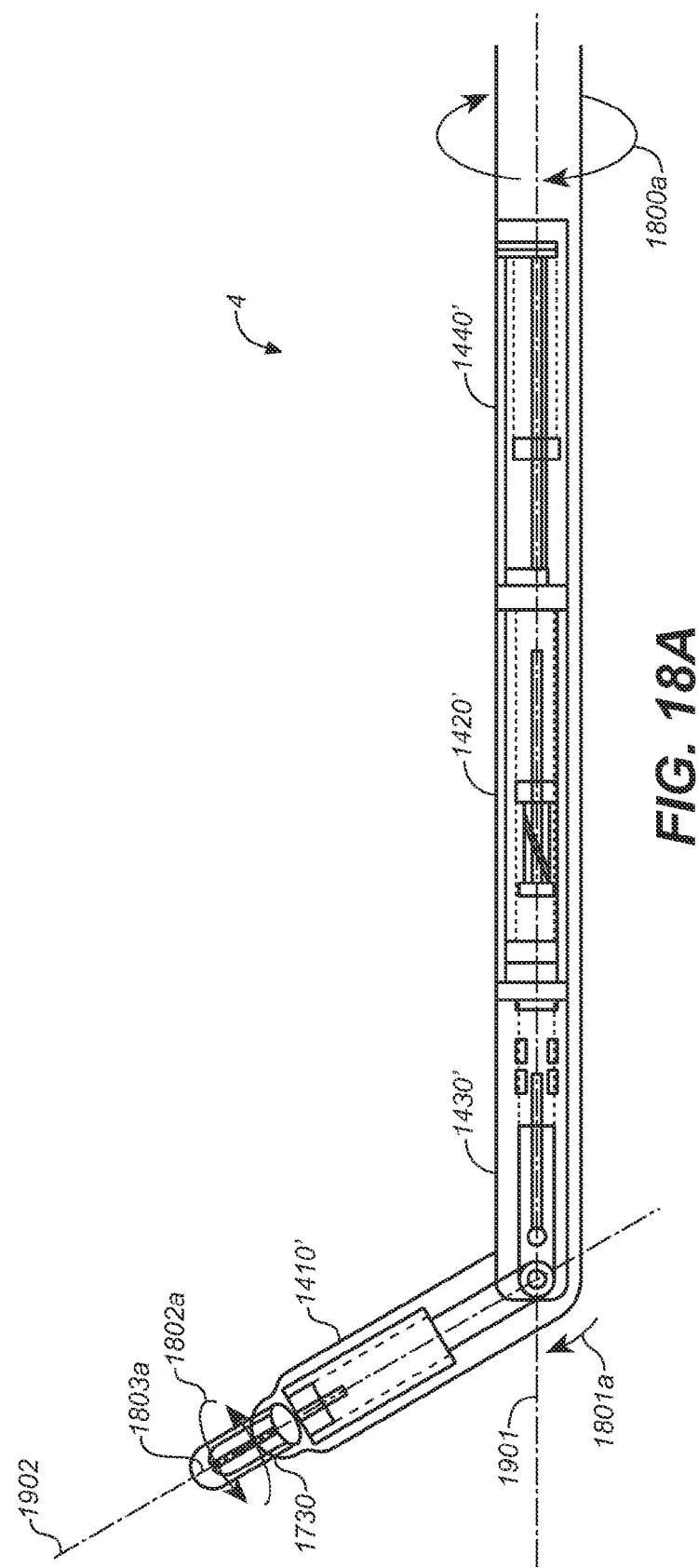

CONTROL PORTION OF AND DEVICE FOR REMOTELY CONTROLLING AN ARTICULATING SURGICAL INSTRUMENT

RELATED U.S. APPLICATION (PROVISIONAL)

This application claims priority to the co-pending provisional patent application, Ser. No. 61/237,042, entitled "Articulated Surgical Tool," filed on Aug. 26, 2009, and assigned to the assignee of the present invention, which is herein incorporated by reference in its entirety.

CROSS REFERENCE TO RELATED APPLICATIONS

The instant Application is related to U.S. patent application Ser. No. 12/869,734, filed on Aug. 26, 2010, entitled "Control Portion Of And Device For Remotely Controlling An Articulating Surgical Instrument," now abandoned, and assigned to the assignee of the present invention. To the extent not repeated herein, the contents of this related patent application are hereby incorporated herein by reference.

The instant Application is related to U.S. patent application Ser. No. 12/869,743, filed on Aug. 26, 2010, entitled "Remotely Controlling an Articulating Surgical Instrument," now abandoned, and assigned to the assignee of the present invention. To the extent not repeated herein, the contents of this related patent application are hereby incorporated herein by reference.

BACKGROUND

Hydraulic systems for applications in laparoscopic surgical tools, as well as tools for other surgical procedures, are known. Current laparoscopic surgical instruments typically have considerable limitations, however, including difficulties in accessing portions of the body obstructed by organs or other objects, difficulties in sterilizing all or portions of such tools, and difficulties in ease of use. Further, while such existing laparoscopic surgical instruments can perform invasive surgical procedures, the instruments are often awkward to manipulate and have problems performing complicated movements often necessary in surgery. In particular, such instruments can be difficult to manipulate around corners, obstacles and to use in obstructed or otherwise difficult to reach environments.

In addition, existing laparoscopic surgical instruments may either have a fairly limited range of motion and/or are not capable of performing certain sophisticated and delicate operations or motions with precision. Further, such instruments may also be fairly limited in their flexibility to accommodate unexpected or unanticipated motion. Also, existing laparoscopic surgical instruments often lack an intuitive connection between motion initiated by the user in the control portion of the device and corresponding motion actuated remotely in the slave portion of the device.

Moreover, existing laparoscopic surgical instruments typically use cables and hydraulic lines to manipulate the surgical tip of the instruments. The hydraulics often require the use of special hydraulic fluid that is not necessarily amenable to surgical environments or other special environments. For example, the use of conventional hydraulic oils in surgical environments is ill-advised and may create an assortment of hazards, especially if the system leaks or the hydraulic conduits are prone to rupture. While more medically compatible hydraulic fluid may be used (e.g., water, mineral oils, etc.), such fluid tends to evaporate at a significant rate. Monitoring and replenishing such fluid manually can be costly and labor intensive. Further, the consequences of not being vigilant concerning fluid levels could be severe, particularly in a surgical environment.

In addition, the tools used by the device can be expensive and difficult to clean and sterilize. Since the cleaning and sterilization procedure must be performed after each use, any expense incurred can substantially add to the cost of use of the device. Alternatively, if disposable tools are used, the need for their continual replacement can add to the cost of the overall system. Also, disposable tools may be made from less robust materials as those meant for multiple uses, leading to increased potential for problems due to equipment malfunction and/or fracture.

Moreover, laparoscopic surgical instruments using cables and hydraulic lines to remotely manipulate the surgical tip of the instruments can be vulnerable to accidental misuse or user overcompensation sometimes due to a lack of direct tactile feedback. This danger is especially significant when the apparatus is not in deliberate use (e.g., when the device is dormant during a critical portion of surgery where other equipment is being used), is being serviced/stored or is not being operated by a skilled practitioner. Inadvertent and potentially damaging maneuvers are possible, for example, when the device is moved in between operating theaters or when routine maintenance is being performed. In particular, problems can arise when a user moves a control for a laparoscopic surgical device in such a way that can cause damage either to the device itself, to ancillary devices and/or to the patient.

BRIEF DESCRIPTION OF THE DRAWINGS

The accompanying drawings, which are incorporated in and form a part of this application, illustrate embodiments of the subject matter, and together with the description of embodiments, serve to explain the principles of the embodiments of the subject matter. Unless noted, the drawings referred to in this brief description of drawings should be understood as not being drawn to scale.

FIG. 3A is a side view of the micro controls 50a of the example control portion shown in FIG. 2A, in accordance with an embodiment;

FIG. 3B is a front perspective view of the control portion of FIG. 3A in use by a user such as a surgeon, in accordance with an embodiment;

FIGS. 4C and 4D are a side view and a front perspective view, respectively, of the macro controls in FIGS. 4A and 4B in use, in accordance with an embodiment of the present invention;

FIGS. 5A and 5B are schematic views of one aspect of an example mechanism that allows actuation of a control cylinder, in accordance with an embodiment of the present invention;

FIG. 13B is a side view of a close up of the clutch safety mechanism of FIG. 13A from the opposite side, in accordance with an embodiment;

FIGS. 16A-16C are a top view, a top view and a side view, respectively, of the control portion, illustrating how an example lateral swivel motion may be actuated by the macro controls, in accordance with an embodiment of the present invention;

FIG. 16F is a perspective view of an example screw mechanism that may actuate the example lateral swivel motion shown in FIGS. 16D and 16E, in accordance with an embodiment;

FIGS. 17A-17C are partial side views of the control portion illustrating how an example extension/retraction motion may be actuated by the macro controls, in accordance with an embodiment of the present invention;

FIGS. 17D and 17E are side perspective views of an example extension/retraction motion in the slave portion that may be actuated by the motion shown in FIGS. 17A-17C, in accordance with an embodiment;

FIG. 18A is a side view of an example instrument to illustrate various articulated motions, in accordance with an embodiment of the present invention.

DESCRIPTION OF EMBODIMENTS

Reference will now be made in detail to various embodiments and aspects of the present invention, examples of which are illustrated in the accompanying drawings. While the subject matter will be described in conjunction with these aspects and embodiments, it will be understood that they are not intended to limit the subject matter to these aspects embodiments. On the contrary, the subject matter described herein is intended to cover alternatives, modifications and equivalents, which may be included within the spirit and scope. In some instances, well-known methods, procedures, objects, devices, structures, and/or circuits have not been described in detail as not to unnecessarily obscure aspects of the subject matter.

Unless otherwise defined, all technical and scientific terms used herein have the same meaning as commonly understood by one of ordinary skill in the art to which aspects and embodiments of the present invention belong. The methods and examples provided herein are illustrative only and not intended to be limiting.

Overview of Components

Figure 1A:
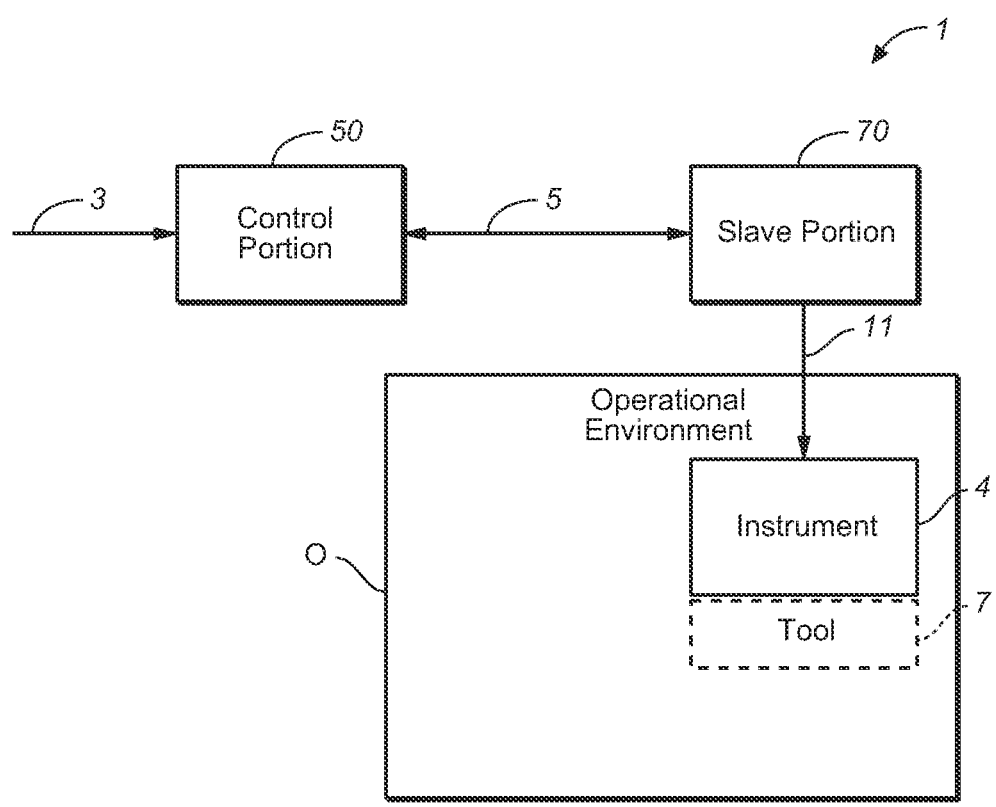
FIG. 1A is a schematic diagram of one aspect of an example device for remotely controlling an instrument or tool in a work environment, in accordance with an embodiment.

FIG. 1A is a schematic diagram of one aspect of an example device 1 for remotely controlling an articulating surgical instrument 4 and/or tool 7 in a work environment O, for example, for performing surgery on a patient. Although the specific aspects of the device may vary according to the application, FIG. 1A-D shows the general overview of this type of device 1, according to one embodiment.

The device 1 may include a control portion 50 operable to receive an input 3, such as a force or motion, to drive the articulating surgical instrument 4 and/or tool 7 which are connected to a slave portion 70 of the device. Although described as being separate components from slave portion 70, it is appreciated that instrument 4 and tool 7 (when included) are also slaved to control portion 50 and thus may be thought of as sub-assemblies of slave portion 70. Herein, articulating surgical instrument 4 is interchangeably referred to as "surgical instrument" and "instrument." The input 3 is transferred from the control portion 50 to the slave portion 70 via a transfer mechanism 5, such as a hydraulic system. Device 1 may be configured to provide a given correlation between input 3 and the resultant output 11 that operates instrument 4 and/or tool 7 within an operational environment O. For example, input 3 may be a linear and/or rotational movement, and output 11 may be a linear and/or rotational movement, and such movements may be combined or correlated in any fashion. For instance, a linear input 3 may be correlated to an output 11 that is linear or rotational, and a rotational input 3 may be correlated to an output 11 that is rotational or linear. Also, the relative degree of transfer may be controlled, e.g., such that a given amount of input 3 produces a given amount of output 11. Further, transfer mechanism 5 may additionally transfer feedback from instrument 4 and/or tool 7 back to control portion 50, thereby providing a user with a direct, tactile feel for the work being performed by the instrument 4 and/or tool 7. In one example of a suitable application for system or device 1, the instrument 4 and/or tool 7 may include an articulating portion for performing surgery within a portion of a body of a patient. Thus, device 1 acts to control, in a precise manner, actions of an instrument 4 and/or tool 7 in an operational environment O from a remote location.

Variations of embodiments of the invention implemented in devices and systems, such as device 1 as well as others, may include a variety of possible movements and motions in both the control and slave portions. Herein, the ability to produce such motions in a device will be described as a "degree of freedom" or "providing a degree of freedom." The term "degree of freedom" is not meant to be used in a strict mathematical or physical sense. Rather, a "degree of freedom" is meant to refer to a certain motion or category of motions that are allowed in the control portion 50, slave portion 70, instrument 4, or other portions of the device 1. One skilled in the art will understand that the systems and devices discussed herein are not limited to the degrees of freedom explicitly described herein. Rather, the devices described herein may be reconfigured even without adding new components such that additional degrees of freedom are included. Further, new components may also be added to devices described herein in order to facilitate new degrees of freedom or to change the scope, direction or other aspect of degrees of freedom discussed herein. Further, the devices discussed herein may also be reconfigured in ways that preserve the degrees of freedom discussed herein. It is to be understood that all such changes are within the scope of embodiments of the invention and that each of the devices configurations and degrees of freedom discussed is merely provided by way of example and not of limitation.

Generally speaking, a large-scale movement that translates multifunctional portions of the device will be referred to as a "macro" movement. However, it is to be understood that this term is not rigorous. For example, macro movements are possible for uni-functional aspects of the device. Macro movements are generally employed for relatively large-scale positioning of the instrument and/or tool closer to or further away from the operational environment O, although macro movements can be employed for other purposes as well. Each macro movement is considered a degree of freedom.

Generally speaking, a small-scale movement that translates a uni-functional portion of the device will be referred to as a "micro" movement. However, it is to be understood that this term is not rigorous. For example, micro movements are possible for multi-functional aspects of the device. Micro movements are generally employed for moving the instrument 4 and/or tool 7 within the operational environment O in order to perform specific operations. However, it is to be understood that micro movements can be employed for other purposes as well. Each micro movement is considered a degree of freedom.

Further, in device 1, the control portion 50 is capable of actuating both macro and micro movements and the slave portion 70 is capable of carrying out both macro and micro movements. Generally, these portions are connected via transfer mechanism 5, such as hydraulic lines. The control portion can provide a user interface to allow actuation of aspects of the slave portion 70 or portions via the hydraulic lines or other mechanisms. Although a particular configuration for the control and slave portions is shown in FIG. 1A, it is to be understood that this is merely one example configuration. As well be shown, several variations of the control and slave portions are part of the spirit and scope of embodiments of the present invention, and variations not shown or discussed herein may also be used in conjunction with embodiments and aspects of the present invention.

Figure 1B:
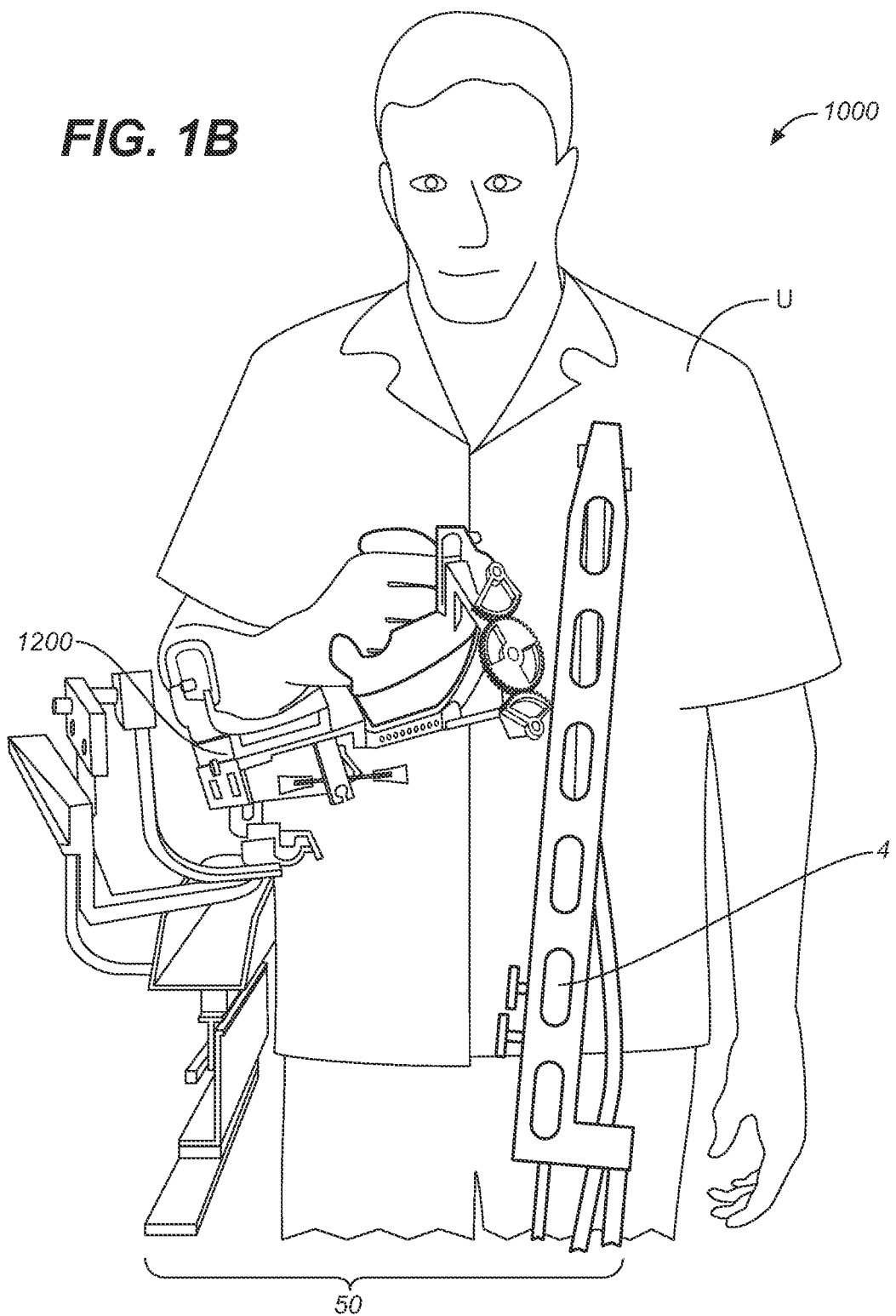
FIG. 1B is a slave end view of one aspect of a manually-actuated, remote surgical system including a control portion that receives inputs to drive a slave portion, for example, to control an instrument or tool in a work environment, in accordance with an embodiment.
Figure 1C:
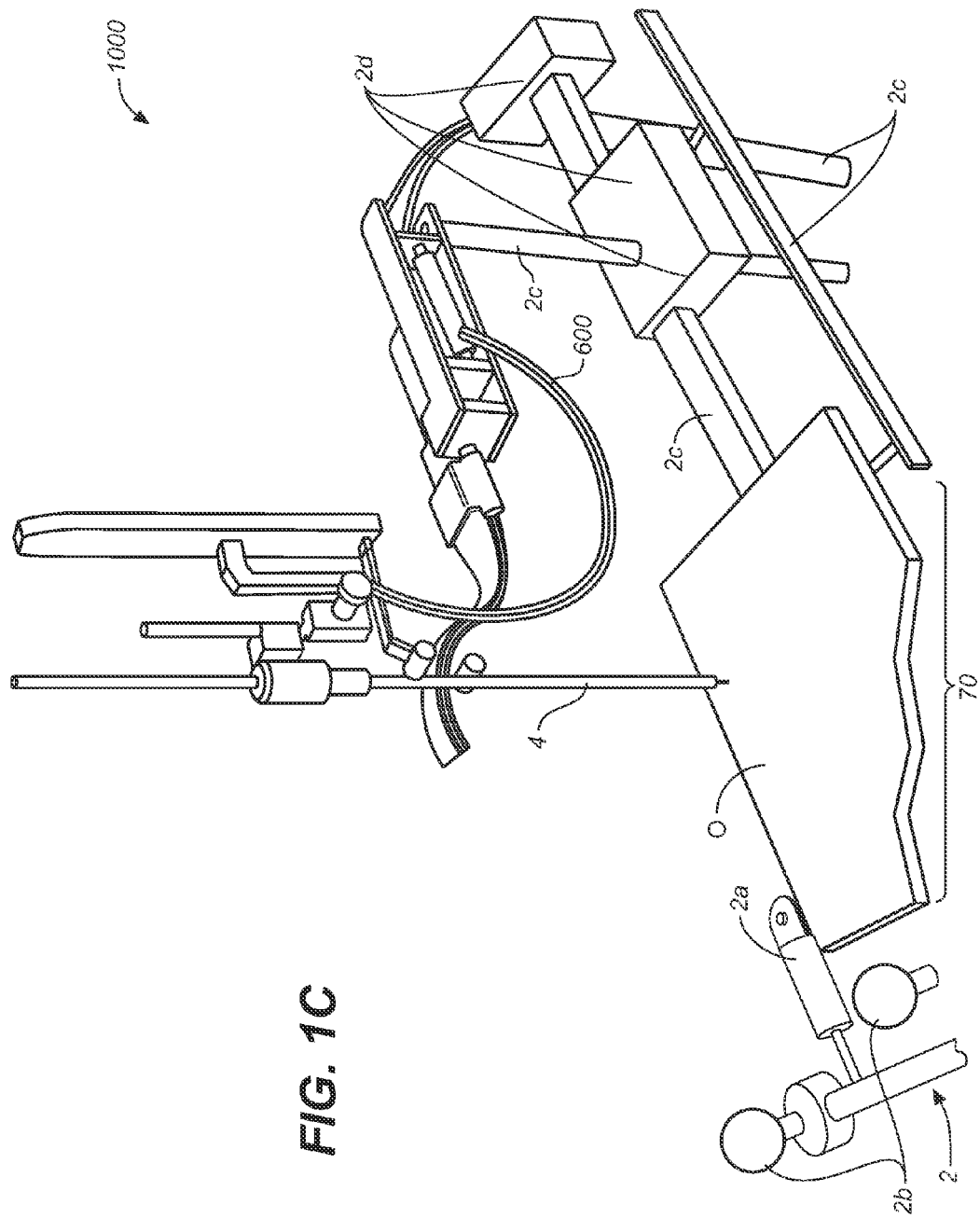
FIG. 1C is a side view the slave portion of FIG. 1A, in accordance with an embodiment.
Figure 1D:
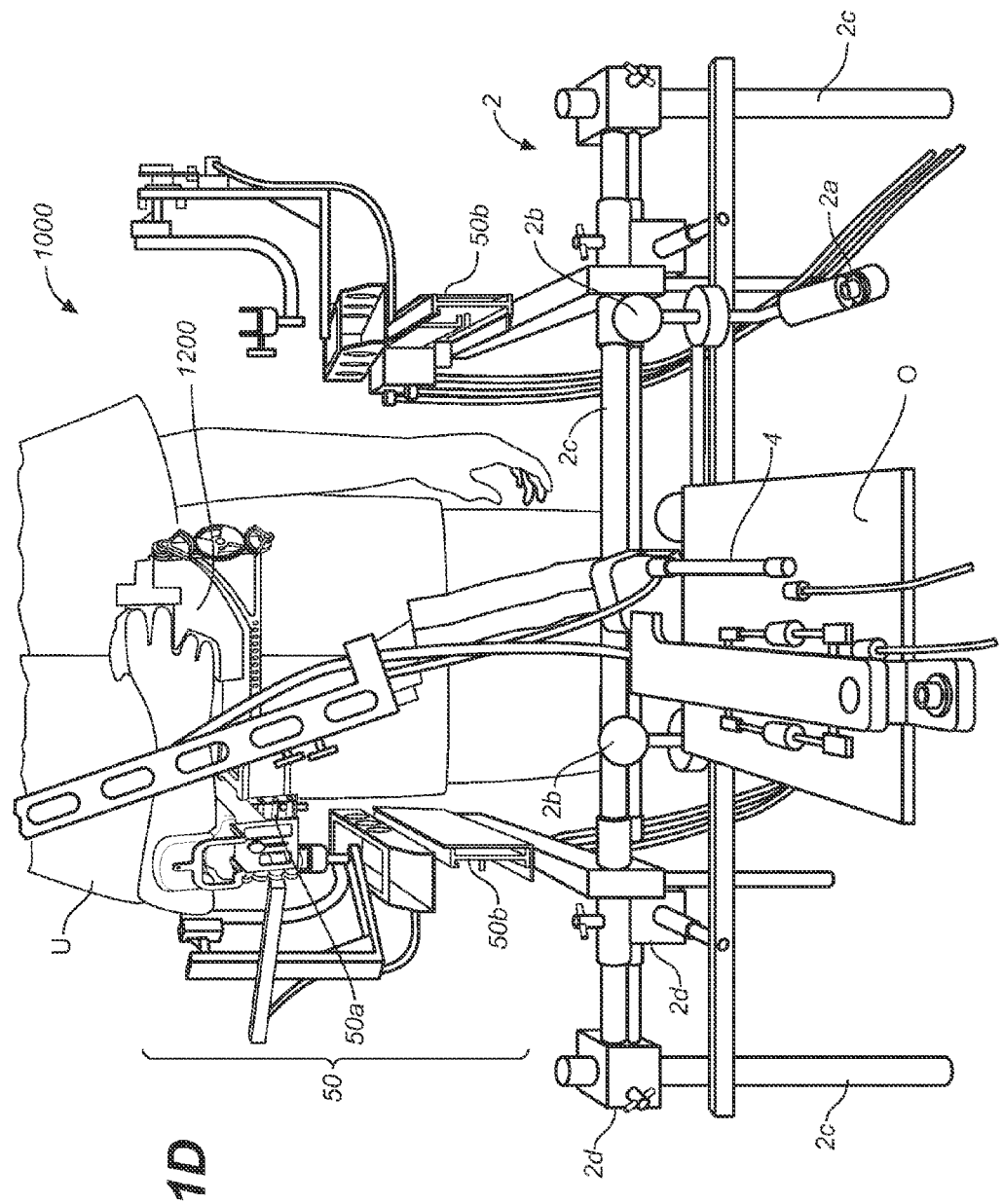
FIG. 1D is a front view of the system of FIG. 1A including additional components, including an additional control portion that may be used to drive an additional slave portion, in accordance with an embodiment.

FIG. 1B shows a variation of a control portion 50 and slave portion 70, and FIG. 1C a more detailed view of the variation of slave portion 70, of an example device 1000 (an embodiment of device 1), according to various embodiments of the present invention. FIG. 1D shows another view of the control and slave portions of FIGS. 1B and 1C, respectively. As shown in FIG. 1B, a user U may operate the control portion 50 by grasping a grasper handle assembly 1200. The grasper handle assembly 1200 and the control portion 50 in general, may have various levers, triggers and/or other actuators. These levers, triggers and/or other actuators are usually connected via a transfer mechanism, such as hydraulic lines, to various parts of the slave portion 70 of the device. For example, FIGS. 1B, 1C and 1D include an instrument 4 and/or tool 7 on the distal end ("distal" end is typically the working end of instrument 4 or tool 7 (when attached to instrument 4) that is located furthest from control portion 50) of the slave portion 70 of the device that may be actuated using the control portion 50 and associated hydraulic systems so that it operates in the operational environment O (FIGS. 1C and 1D). For example, pulling a trigger on the grasper handle assembly 1200 may extend the instrument 4 in the direction towards the operational environment O. Alternatively, the instrument 4 may have a number of functionalities (e.g., cutting, grasping, gouging, and piercing) that may be actuated by the trigger or other portions of the grasper handle assembly 1200. Multiple instruments 4 and/or tools 7 may also be configured for use in the slave portion 70, examples of which will be explored in greater detail below. The operational environment O may be a surgical operating environment, an environment such as an assembly environment or another environment.

FIGS. 1C and 1D also show an adjustable stand 2 that may be used to fix the control portion 50, the slave portion 70 or both to a particular location or object. For example, the stand 2 may be fixed to a side of a table in an operating room. Alternatively, the stand 2 may be a self-standing apparatus for supporting the device 1 in any suitable location. As such, the stand 2 may also be fixed in other locations, such as in an environment where mechanical or electrical work is to be done. The stand 2 may include various components that allow different parts of the device 1000 to be adjustably positioned at various locations. For example, FIGS. 1C and 1D show a series of grip handles 2a and knobs 2b that may be used to alternatively fix and release various posts and beams 2c providing support to parts of the device 1000. In addition, the beams 2c, or other components, may be connected to each other or to other objects using vices, crimpers or clamps 2d. It is to be understood that the structure for the adjustable stand 2 shown in FIGS. 1C and 1D is merely representative. In fact, the structure of the stand 2 can be reconfigured, rebuilt and/or adjusted as needed.

Figure 2A:
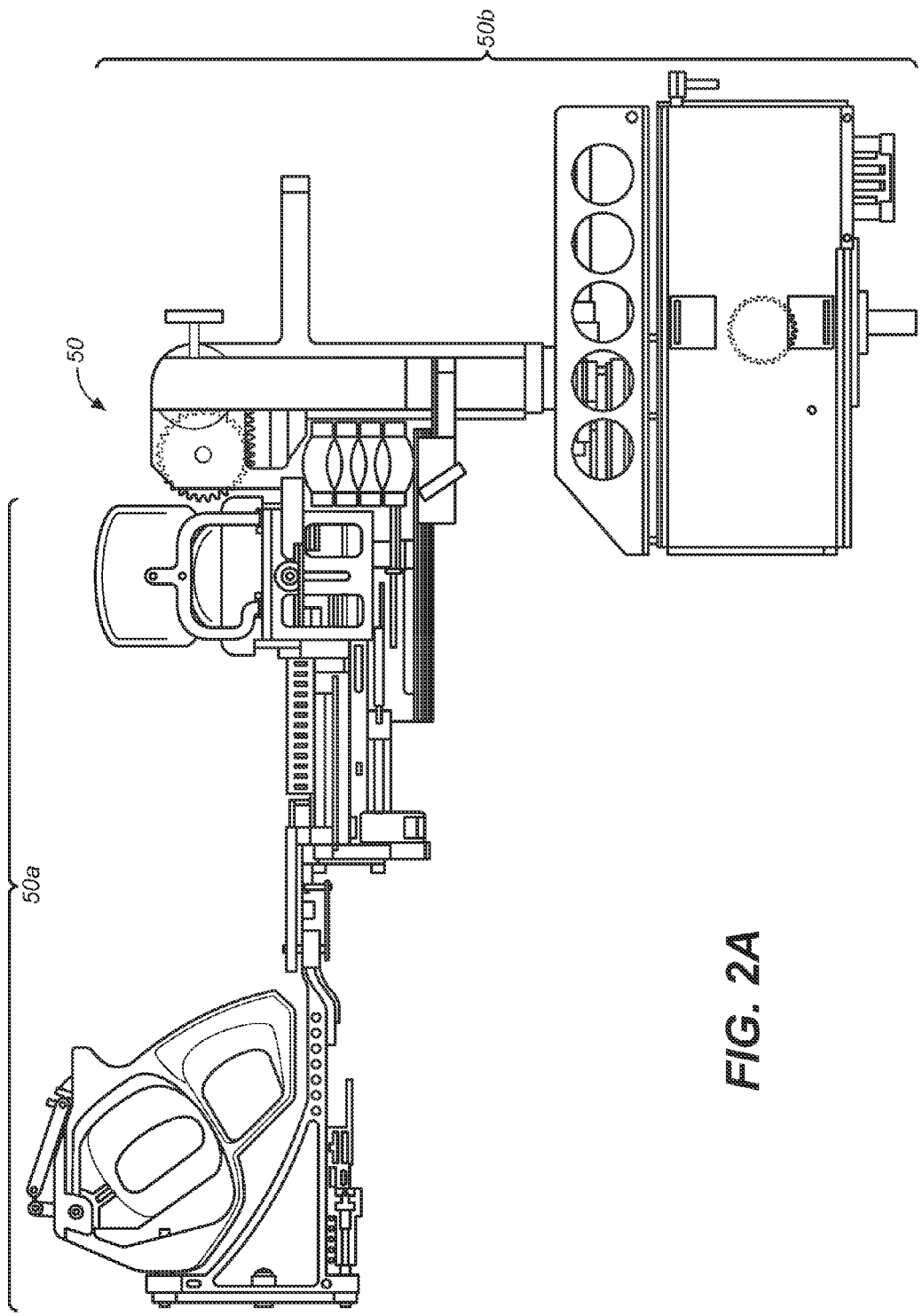
FIG. 2A is a detailed drawing of a side view of one variation of an example control portion that may be used in conjunction with embodiments of the present invention.
Figure 2B:
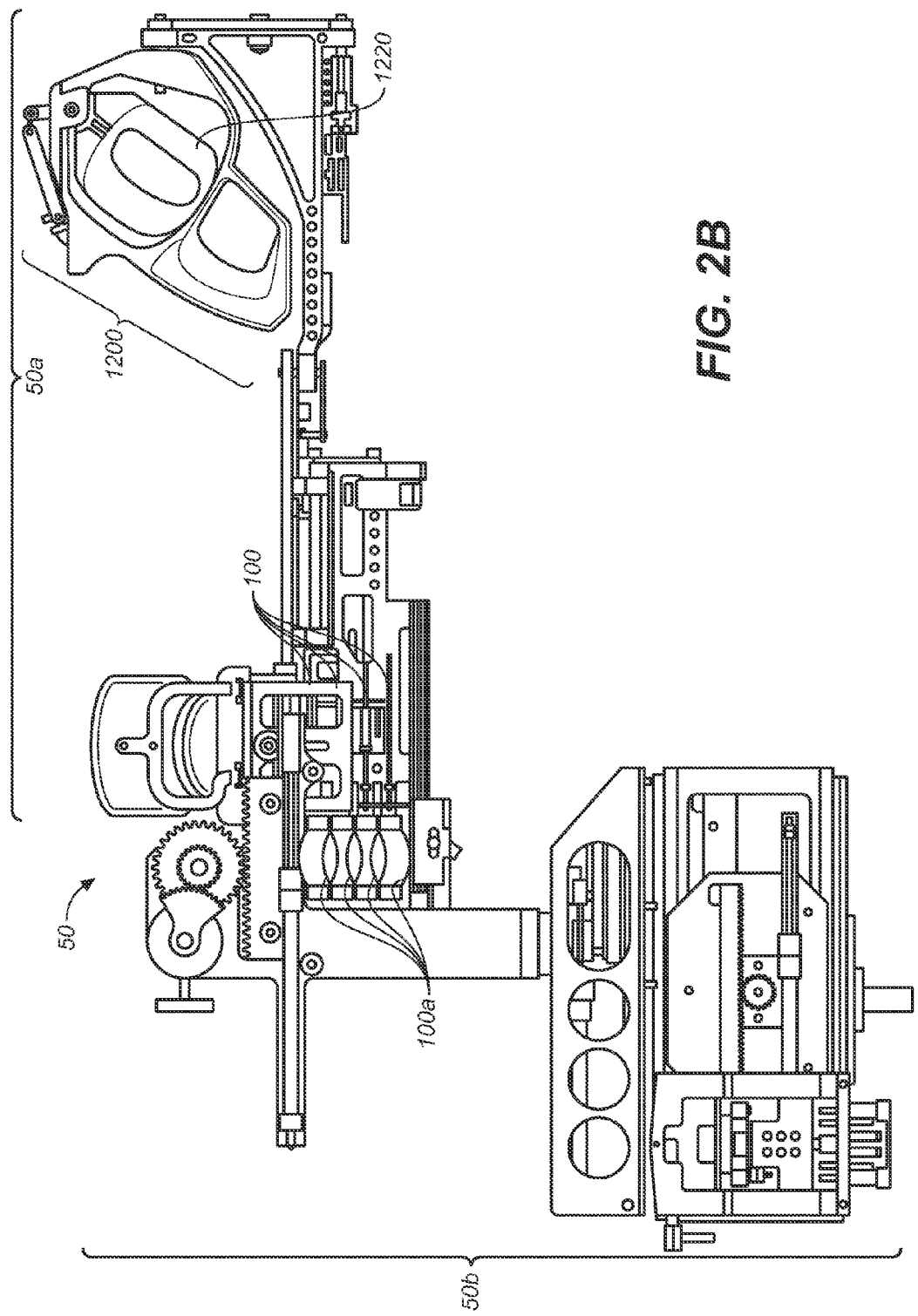
FIG. 2B is a detailed side view of an opposite side of the example control portion shown in FIG. 2A, in accordance with an embodiment.

FIG. 2A is a detailed drawing of a side view of one variation of an example control portion 50 that may be used in conjunction with embodiments of the present invention. FIG. 2B shows an opposite side of the example control portion shown in FIG. 2A. The example control portion 50 is similar to the control portion 50 shown in FIGS. 1B and 1D and may be operated in the manner shown in those Figures, or in ways that are not explicitly represented in the Figures. The topmost portion of the control portion 50 contains micro controls 50a. The specifics of the micro controls 50a will be described in detail below, but in general the micro controls 50a may control the micro or relatively-finer motion of aspects of the slave portion 70. For example, the micro controls 50a may control movements of instruments 4 and/or tools 7 coupled with the slave portion 70 and which can be located or utilized within the operational environment O. In contrast, the macro controls 50b shown in the lower portion of the device 1000 in FIGS. 2A and 2B may be used to control macro or relatively coarser motions of the slave portion 70. For example, the macro controls 50b may be used to bring the instrument 4 and/or tools 7 coupled with the slave portion 70 in proximity to the operational environment O from another position (e.g., a position outside of where contact between the instrument and/or tools and an object upon which work is to be performed, or a position where the instrument and/or tools are being serviced). However, as noted above, these definitions are not literal, specific or rigorous and merely serve to give a broad understanding of how various aspects relate to one another.

The control portion 50 shown in FIG. 2B may have other aspects that give it additional degrees of freedom in the motions that may be transmitted from the user to the slave portion 70 of the device. These additional aspects will be discussed in more detail below. Generally, each degree of freedom corresponds to its own control cylinder 100, as shown in FIG. 2B. For example, the user may grasp the grasper handle assembly 1200 and squeeze the trigger 1220, as well as move grasper handle assembly 1200 in various directions. These and similar motions define an input force or input motion 3 (FIG. 1A) that generally effect a mechanical response in the control cylinders 100, which transmit the mechanical response to the slave portion 70 of the device.

FIG. 3A highlights the micro controls 50a of the example control portion shown 50 in FIGS. 2A, 2B. FIG. 3B shows the micro controls 50a of FIG. 3A in use. FIG. 3A shows several example features of the micro controls 50a, including a grasper handle assembly 1200, and a trigger 1220 for interacting with the user. Generally, the user may grasp the grasper handle assembly 1200, as shown in FIG. 3B, and squeeze the trigger 1220. This motion and similar motions generally affect a mechanical response in one or more of the control cylinders 100, also shown in FIG. 3A, which transmit the mechanical response to the slave portion 70 of the device (FIG. 1C).

FIG. 3A also shows a closer view of example spool valves 100a attached to each of the control cylinders 100 for, among other things, keeping the hydraulic lines filled with fluid. As shown in FIG. 3A, the spool valves 100a are generally connected to each of the control cylinders 100 on one end and contain a portion of the control fluid communicating between the control cylinder 100 and the slave portion 70 of the device. Although the fluid connections are not explicitly shown in FIG. 3A, they may be made by any suitable connection. Generally, one connects a hydraulic line at the inlets in the spool valves 100a and connects the other end of the hydraulic line to a corresponding control cylinder on the slave portion 70 of the device. In this configuration, each degree of freedom typically has one control cylinder in the control portion and one corresponding control cylinder in the slave portion 70. These respective control cylinders may be connected using the spool valves 100a described in U.S. Provisional Patent Application No. 61/297,630, titled "HYDRAULIC DEVICE INCLUDING A SPOOL VALVE" filed on Jan. 22, 2010, and U.S. Provisional Patent Application No. 61/297,784 titled "OVERFORCE MECHANISM" filed on Jan. 27, 2010 which are both hereby incorporated herein by reference in their entirety. As described in more detail in U.S. Provisional Patent Application No. 61/297,630 another purpose of the spool valve of embodiments of the instant invention, among others, is to control fluid communication between the control cylinder 100 and the slave portion 70 of the device. Although spool valves 100a may not be shown in conjunction with each control cylinder 100 shown herein, it is to be understood that a spool valve 100a may be used with any of the control cylinders 100 discussed herein. Note that the control portion 50 as shown in FIGS. 2A, 2B and 3A, and each of its components, is a non-limiting example of one of the types of control portions that may be used in conjunction with embodiments of the present invention. It is to be understood that aspects of various embodiments of the present invention can be used in conjunction with a variety of other devices, including other control portions.

Figure 4A:
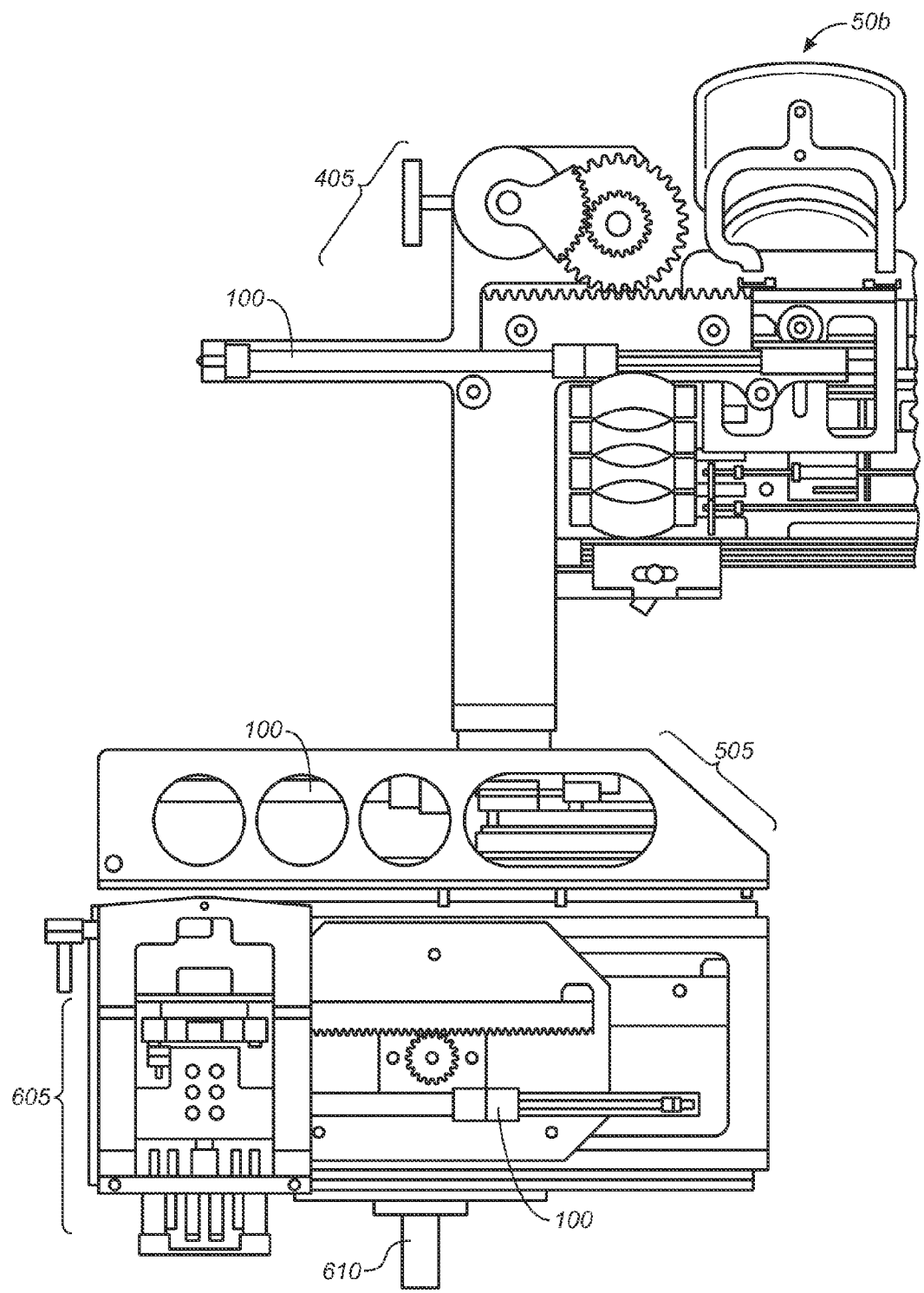
FIG. 4A is a side view of the macro controls of the example control portion shown in FIG. 2A, in accordance with an embodiment.
Figure 4B:
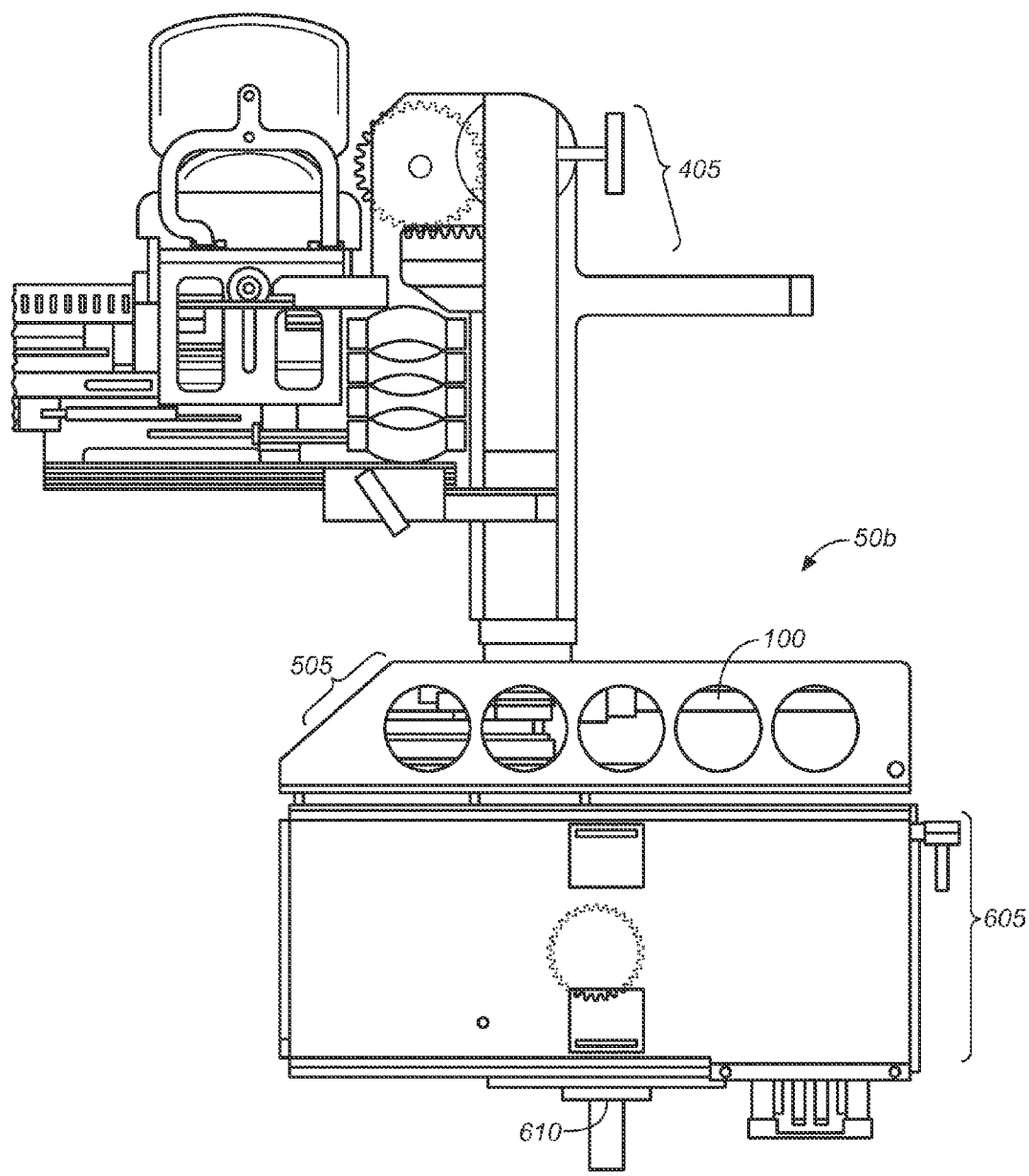
FIG. 4B is a side view of an opposite side of the macro controls of the example control portion shown in FIG. 4A, in accordance with an embodiment.

FIGS. 4A and 4B highlight the macro controls 50b of the example control portion shown in FIG. 2A. As shown in FIG. 4A, in one embodiment, the macro controls 50b may include three control cylinders 100. The control cylinders 100 may actuate different degrees of freedom in the device 1000. Example degrees of freedom will be discussed in more detail below. Each of the control cylinders 100 has an associated transmission assembly 405, 505 and 605, respectively, for example, including gear assemblies thereof. Generally, the transmission assemblies of the macro controls 50b serve to translate user motion to the control cylinders 100, which then translate that motion into the displacement of hydraulic fluid in communication with corresponding control cylinders in the slave portion 70 of device 1. As will be described herein, such a displacement of hydraulic fluid constitutes one example of a type of control signal that can be generated by control portion 50. Although specific transmission assemblies 405, 505 and 605 will be shown in the context of device 1000, it is to be understood that they may be replaced by any suitable transmission or gear assembly (or other actuating assembly) that serves to translate user motion to the control cylinders 100. It is to be further understood that the number of control cylinders and gear assemblies shown in FIGS. 4A and 4B is merely an example of the number that may be utilized. Additional degrees of freedom may be added by adding new control cylinders 100. Alternatively, not all of the control cylinders 100 shown in FIGS. 4A and 4B need be present or operational in the macro controls 50b.

Generally speaking, the macro controls 50b actuate macro motions in the slave portion 70 of the device. Such macro motions may include, but are not limited to, positioning instrument 4 and/or tool 7 appropriately so that it may perform operations on a specific area of the operating environment O. FIGS. 4A and 4B also show an anchor 610 that may serve to anchor the control portion 50 to a fixed object or another portion of the device 1000. For example, the anchor 610 may simply be a peg (as shown in FIGS. 4A and 4B) for anchoring the control portion 50 to a stand, desk, table or bedside by fitting into a peg receptacle on one of these objects. Alternatively, the anchor 610 may include a clamp, screws or fasteners for anchoring the control portion 50 to an object. In some aspects, anchor 610 may allow fixed relative movement between control portion 50 and the object to which it is anchored. For example, the anchor 610 may allow relative rotational movement between different fixed positions between the control portion 50 and the object to which it is anchored in order to fix. For example, such relative movement may be desired for user comfort in positioning device 1 or portions thereof relative to the user's body. In other aspects, anchor 610 may fixedly position the control portion 50 to the object to which it is anchored.

FIGS. 4C and 4D show the macro controls in FIGS. 4A and 4B in use by a user U. As shown in FIGS. 4C and 4D, the user may grip the grasper handle assembly 1200 and rest his/her elbow in arm holder assembly 1100. The user U may generally actuate the macro controls 50b using the forearm and the elbow in conjunction with the arm holder assembly 1100, or other portions of his/her body. The details of the interaction will be discussed below. It is noted that the macro controls 50b and micro controls 50a shown herein are merely examples. For example, the macro controls 50b and micro controls 50a may include additional levers, triggers, screws, buttons, latches switches, paddles, moveable pins, pedals (e.g., a foot pedal), and touchless sensors. The macro controls 50b and micro controls 50a may also include additional aspects that make the user more comfortable (e.g., cushions, padding, fans, cooling devices). Additionally, one or more function control mechanisms 50c (see e.g., FIG. 12B for one example implementation and FIG. 13A for another example implementation), which may take many forms, may be included in some embodiments. Function control mechanism 50c, when included, allows a user to control a function associated with device 1. The function controlled is in addition to the movements in the degrees of freedom that are controlled by macro controls 50b and micro controls 50a.

Interaction of Control Portion with Control Cylinders

It should be noted that a number of different mechanisms for actuating control cylinders are disclosed herein. While certain variations of actuation mechanisms may be more appropriate for certain applications, it is to be understood that most of the actuation mechanisms discussed here are, to some extent, interchangeable. That is, it would be possible to apply a particular actuation mechanism (including various components for manipulating mechanical motion including gears; levers, screw members, linkages, pistons or other components) for another suitable purpose. Many of the actuation mechanisms discussed in the context of a particular degree of freedom may also be employed to actuate different degrees of freedom discussed herein and different degrees of freedom that are not discussed herein. It is to be understood that such variations fall within the scope of embodiments of the present invention.

FIGS. 5A and 5B illustrate an example mechanism for controlling actuation of force or motion, in the form of a control cylinder 100. As shown in FIGS. 5A and 5B, the control cylinder 100 includes an outer cylinder 101 which, can include a control cylinder shaft 101a inside an inner cylinder 102. Upon application of an input 3 of a force or motion to micro controls 50a and/or macro controls 50b, a corresponding control cylinder 100 may be actuated, for example, through one or more levers and/or gears, from the retracted position shown in FIG. 5A to the extended position shown in FIGS. 5A and 5B. It should be understood, however, that control cylinder 100 is one of a plurality of possible actuation mechanisms that may be used to perform the functions described herein. For example, other actuation mechanisms may include one or any combination of mechanical actuators, hydraulic actuators, magnetic actuators, or the like.

As noted above, an example control cylinder 100 includes an outer cylinder 101 and an inner cylinder 102. The inner cylinder 102 is free to move within the outer cylinder 101, while the outer cylinder 101 is connected to a shaft 101a, where the shaft 101a is in mechanical communication with a corresponding feature of micro controls 50a or macro controls 50b of the control portion 50. The movements of the control portion 50, described above, cause the outer cylinder 101 to move longitudinally with respect to the stationary inner cylinder 102.

A piston 101b, attached to a shaft 101a, moves within the inner cylinder 102. The distal end of the shaft 101a is configured to be capable of attachment to the piston 101b, while the proximal end of the shaft 101a is configured to be capable of attachment to the outer cylinder 101. A fluid 20, such as air, saline, water, oil, etc., is located in the inner cylinder 102 in front of the piston 101b. When the control portion 50 is moved as described above, the outer cylinder 101 moves forward, thereby moving the shaft 101a and the piston 101b. Fluid 20 exits the inner cylinder 102 through an outlet, creating a displacement of hydraulic fluid at a point in the distal end of the device. Additional fluid 20, displaced from a slave control cylinder, enters to the back of the piston 101b through an inlet, thereby keeping the volume of the fluid 20 in the system constant. When the control portion 50 is moved to a first end position, the control cylinder 100 is in its retracted position, FIG. 5A. In this position, the piston 101b is at the distal end of the inner cylinder 102. The fluid 20 is in the back of the piston 101b.

Generally, the control cylinder 100 slides back and forth within the inner cylinder 102 as shown in FIGS. 5A and 5B. In this way, among others, the control portions use the control cylinder 100 to channel the mechanical force from the user to the instrument 4 and/or tool 7. Although broken out separately in FIG. 1A and describes separately herein, generally speaking, components actuated by a control cylinder 100 are referred to as the "slave" components of the device because they move under control of signals received from control portion 70 via one or more control cylinders 100. These slave components may include slave portion 70, instruments 4, and/or tools 7. Tools 7 include, but are not limited to tools such as: mechanical grippers, lever arms, cutting tools, grasping tools and any other suitable devices. The mechanical force can be used in any number of suitable ways by the slave portion 70 of the devices. For example, the control portions can be used to conduct surgical procedures, move objects or to mechanically provide force for any suitable number of applications. For example, the control portions may be coupled to various surgical apparatus (e.g., clamps, shears, needles, etc.) for performing a surgical operation.

In some aspects, control cylinders 100 may include clutch mechanisms (not shown) that shunt inadvertent over-forcing of the macro or micro controls away from the hydraulic systems in order to prevent damage to components. Example clutch mechanisms are described in Applicants' co-pending U.S. Provisional Patent Appl. No. 61/297,784 titled "OVER-FORCE MECHANISM" filed on Jan. 27, 2010.

Control cylinders 100, such as those shown in FIGS. 5A and 5B, can be used to drive complex mechanical systems in conjunction with other control cylinders. For example, one control cylinder may be actuated by the control portion 50 of FIG. 2B and communicate fluid, ultimately, with one or more other control cylinders in the slave portion 70 of the device. Coupling of the hydraulics between the control cylinders in the master and the slave portions of the device may be accomplished by a variety of means including by directly connecting hydraulic lines, by use of a number of suitable connectors, valves and other fixtures. However, it may be advantageous for the connection to contain a de-coupling mechanism so that the slave components and control portions can be hydraulically de-coupled from one another when not in use. Further, as many of the lines and connections used in surgical hydraulic systems and other similar hydraulic systems can allow evaporation of the hydraulic fluid, it is also advantageous for connectors to provide a mechanism of replenishing the hydraulic fluid. Example de-coupling mechanisms and fluid replenishment mechanisms are described in Applicants' co-pending U.S. Provisional Patent Application No. 61/297,630 titled "HYDRAULIC DEVICE INCLUDING A SPOOL VALVE" filed on Jan. 22, 2010.

In summary, in some aspects, some of the actuated mechanical devices, such as the one shown in FIGS. 1A, 2B and 2C, may contain control portions with a single control cylinder or control portions with multiple control cylinders. These control portions with a single control cylinder or control portions with multiple control cylinders may serve to allow a user, such a surgeon, to actuate mechanical operations in another portion of the device. For example, the control portions with a single control cylinder or control portions with multiple control cylinders may actuate and move various tools for the implementation of surgery. Generally speaking, the control portions control portions with a single control cylinder or control portions with multiple control cylinders) are part of the control portion of the device and the various instruments and/or tools are coupled with the slave portion 70 of the device. The connections between the control and slave portions are primarily hydraulic in nature to allow transmission of mechanical forces between the two portions. However, other connections (e.g., electrical, pneumatic, electromagnetic, and optical) may also be present in order to transmit various types of information between the two portions of the device.

Figure 6A:
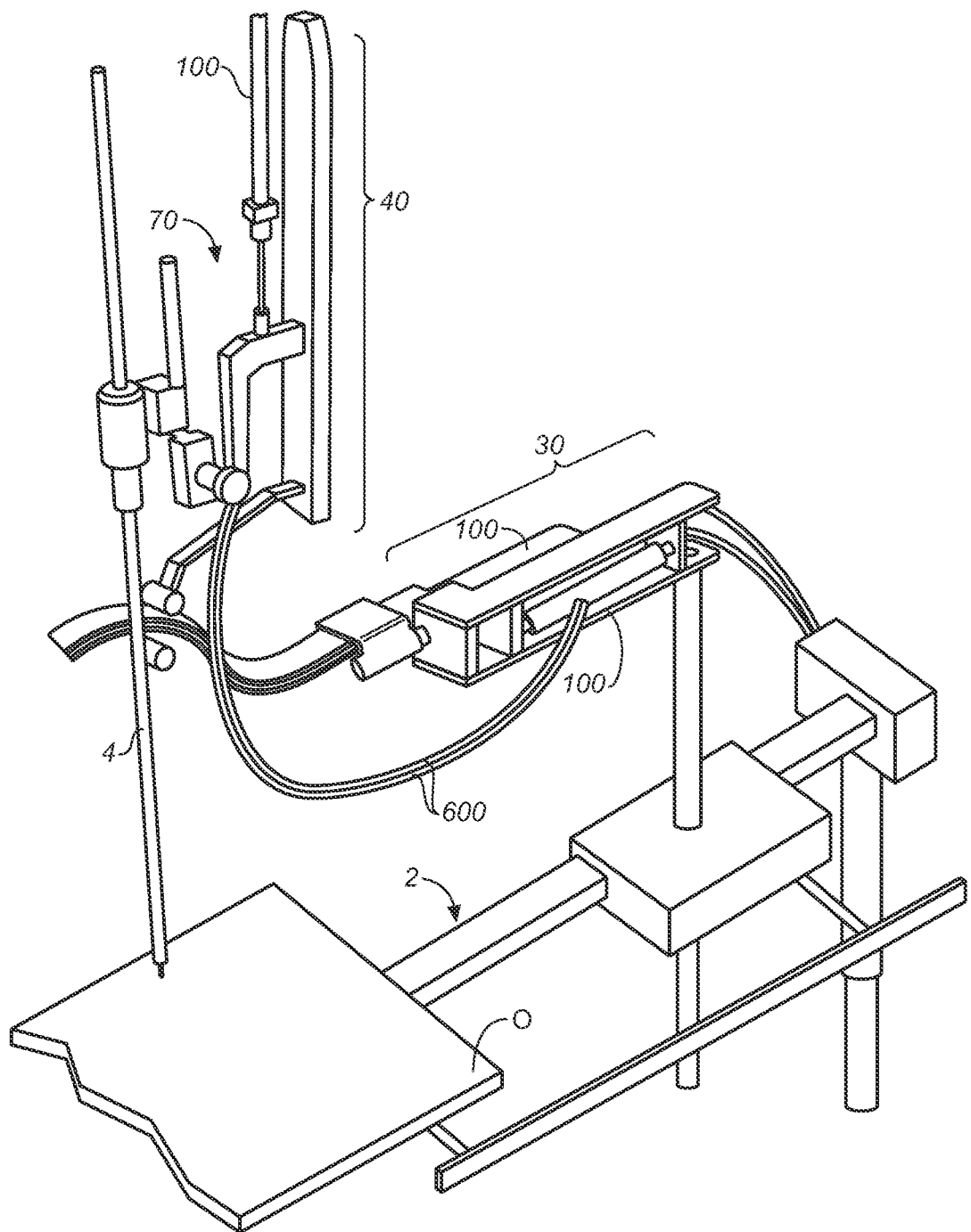
FIGS. 6A and 6B are side perspective views of aspects of the slave portion, in accordance with an embodiment of the present invention.
Figure 6B:
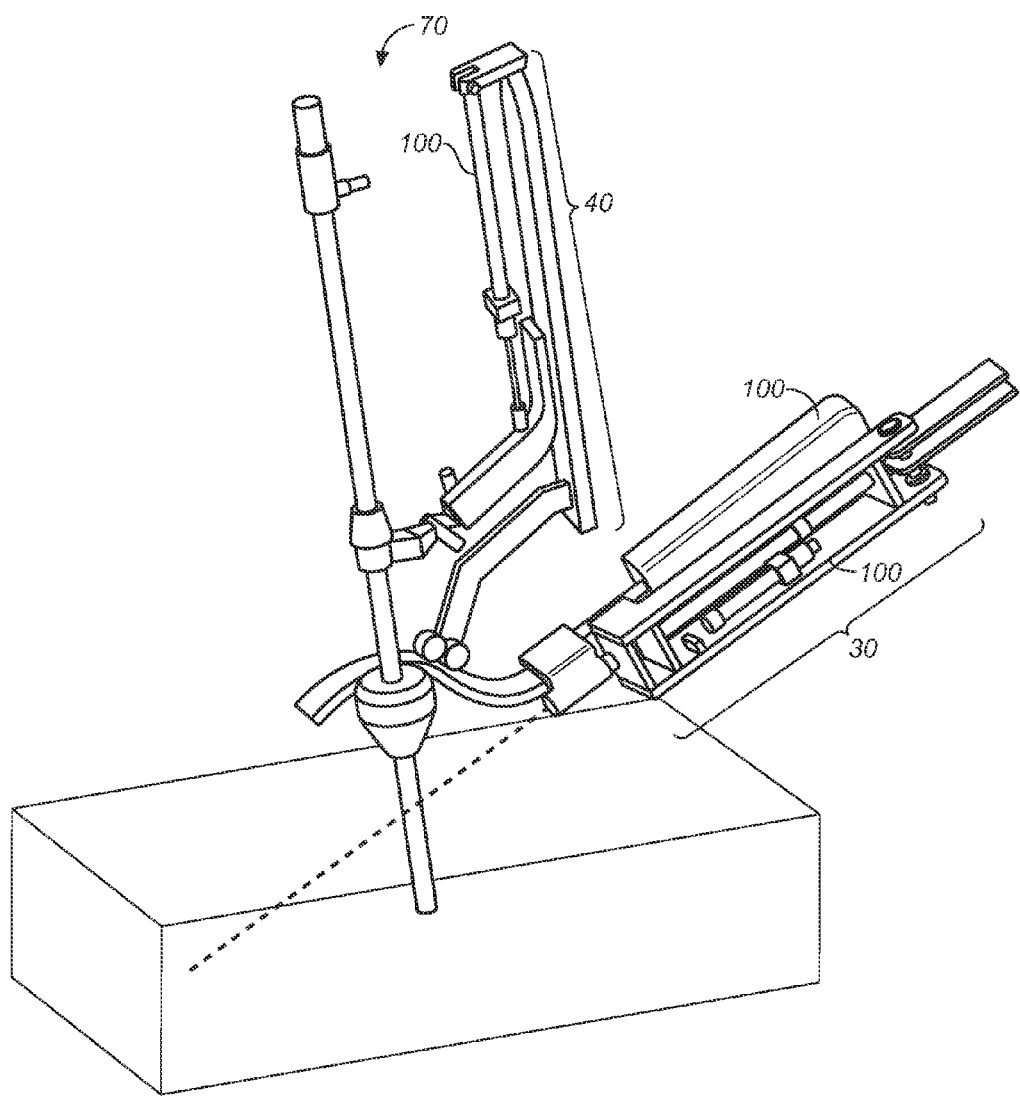
Figure 7:
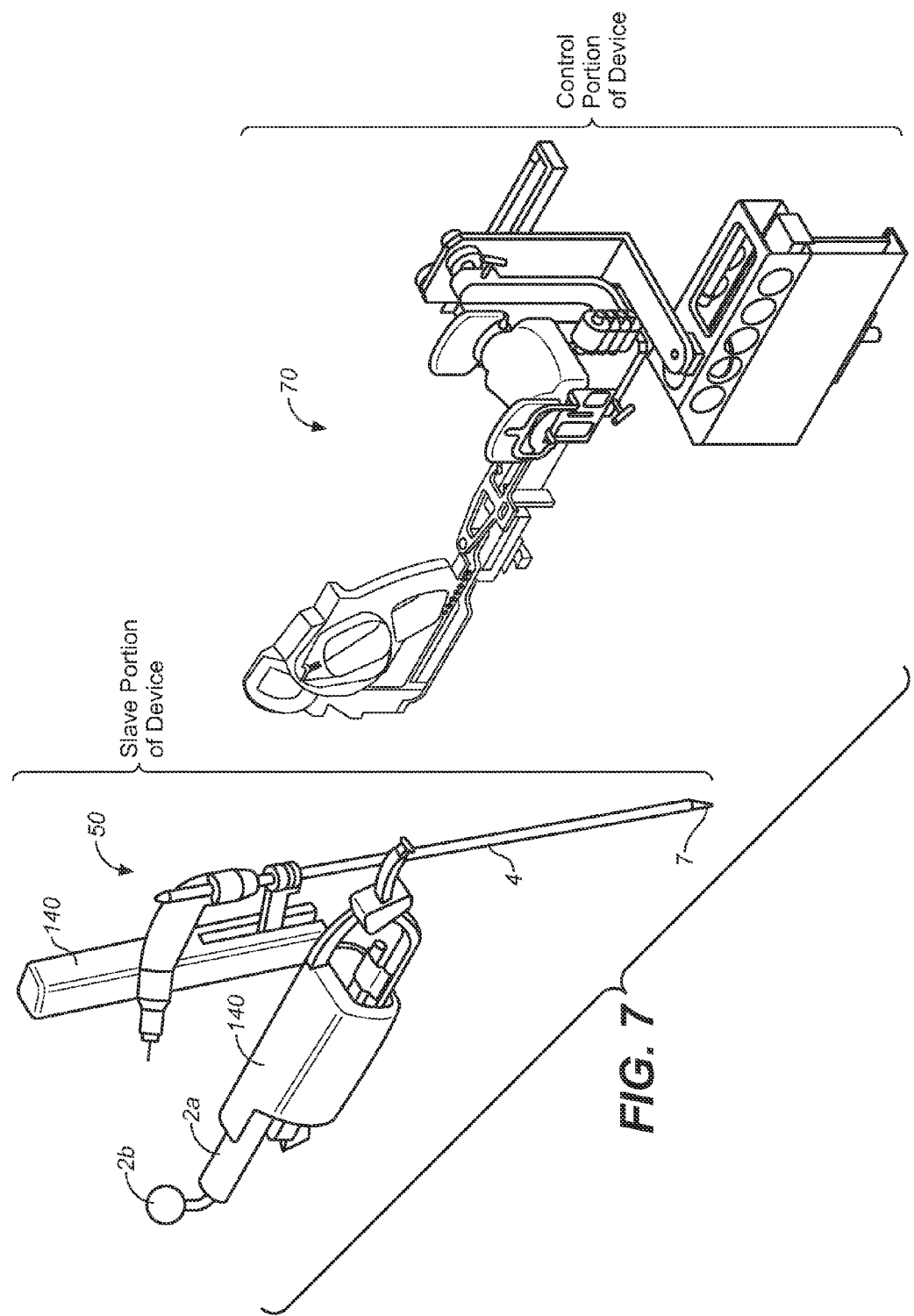
FIG. 7 is a perspective view of another aspect of the slave and control portions, in accordance with an embodiment of the present invention.
Figure 8:
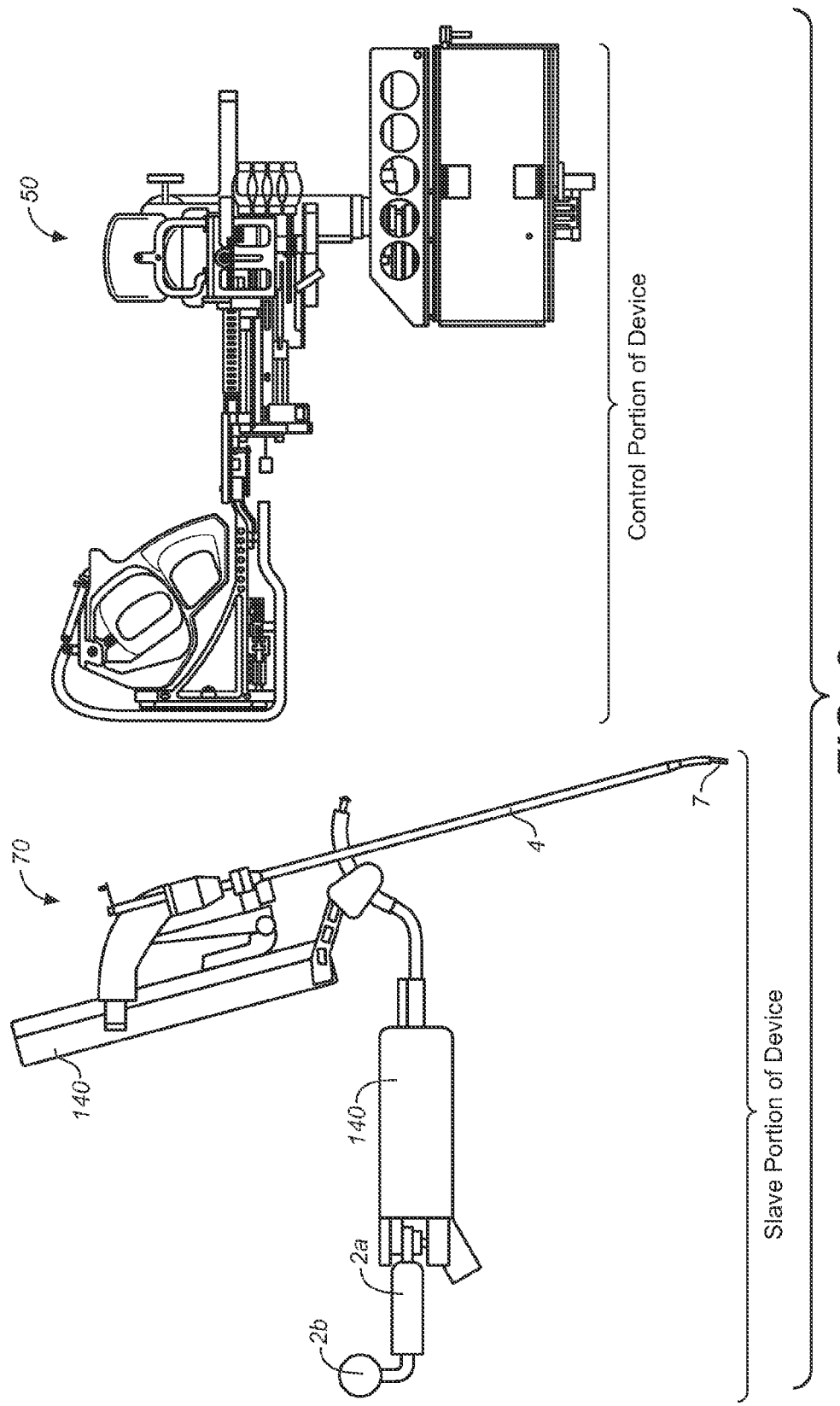
FIG. 8 is a side view of the device in FIG. 7, in accordance with an embodiment.
Figure 9:
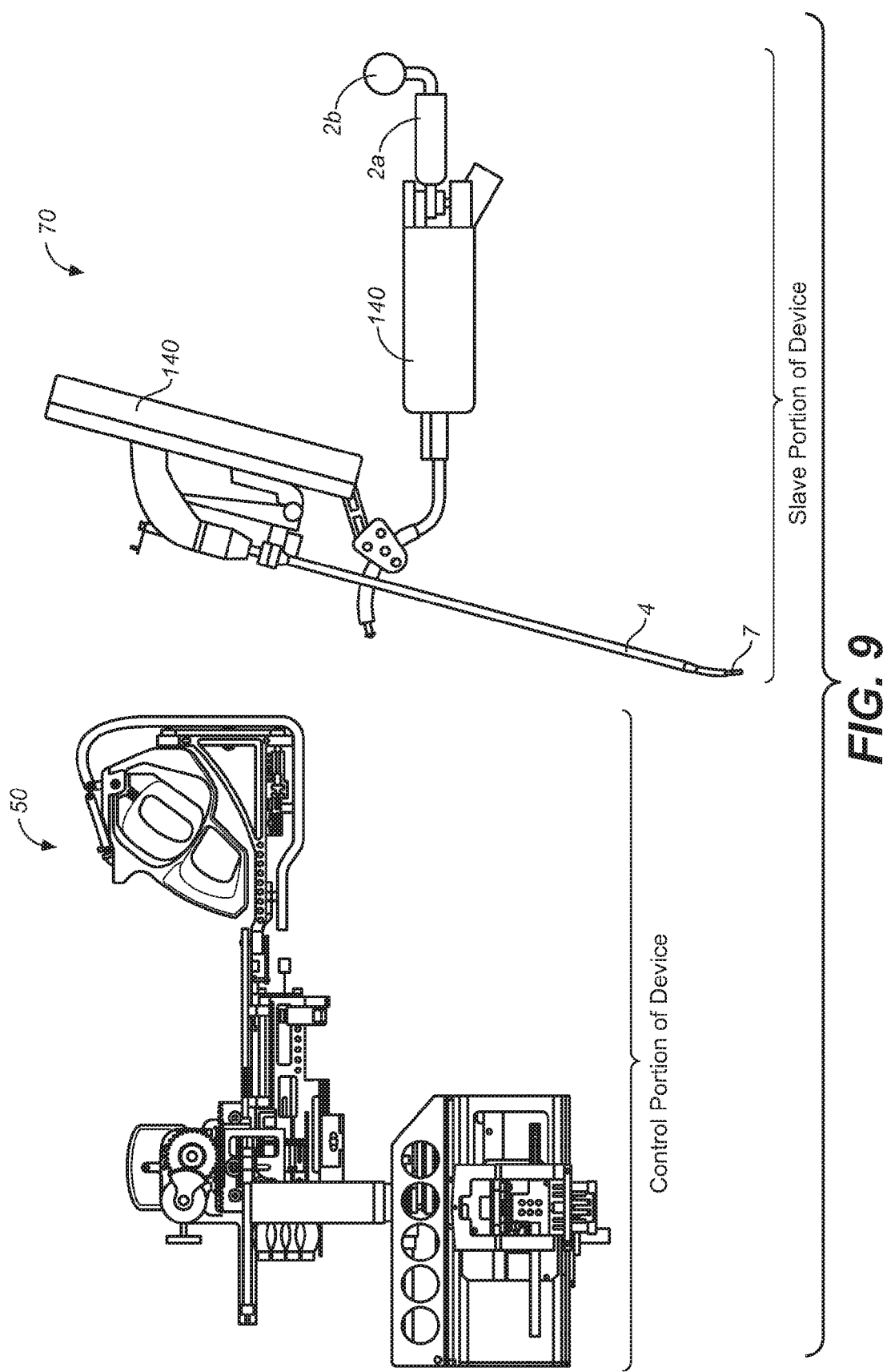
FIG. 9 is a side view from a side opposite from the view in FIG. 8, in accordance with an embodiment.
Figure 10:
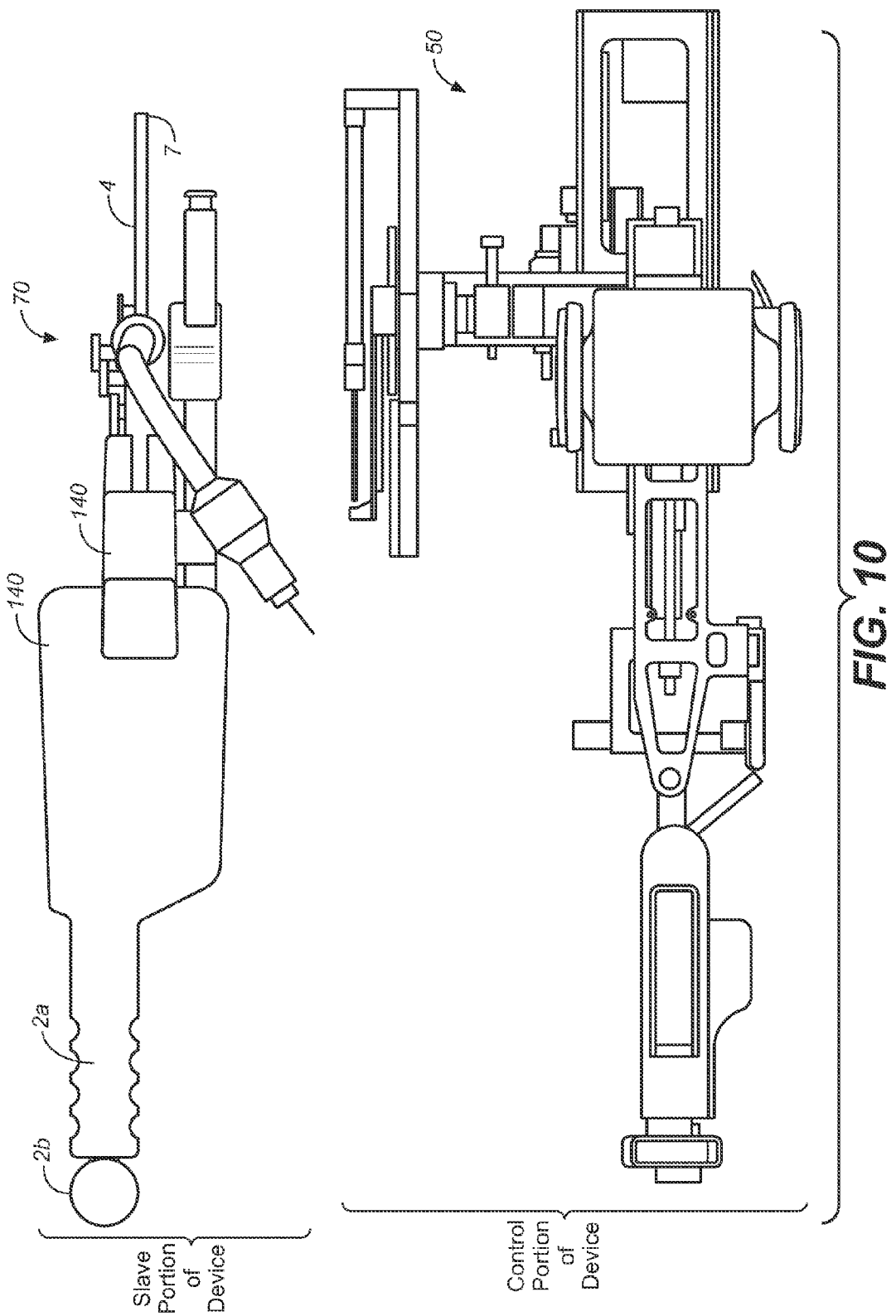
FIG. 10 is a top view of the slave and control portions of the device of FIG. 7, in accordance with an embodiment.
Figure 11:
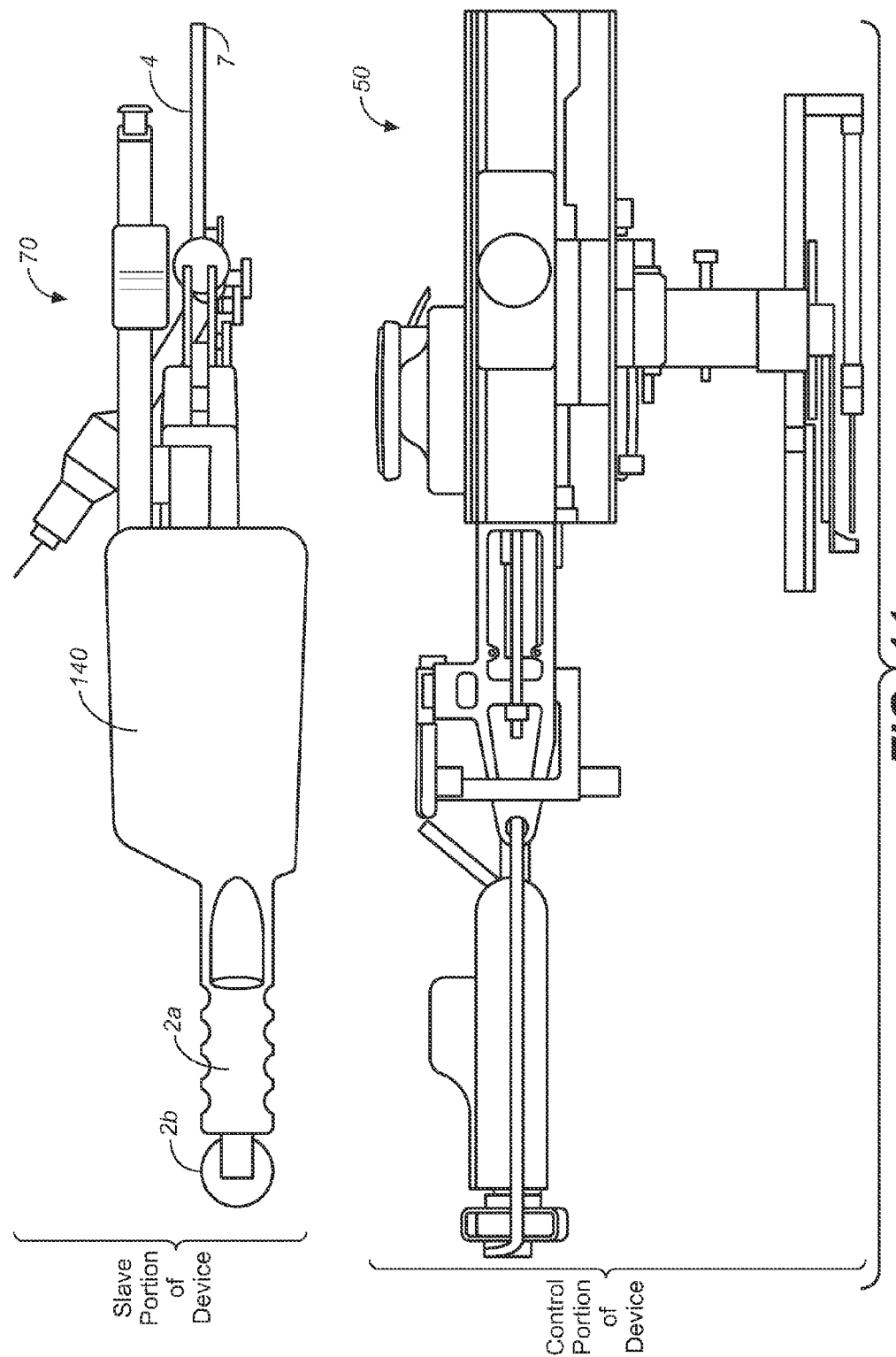
FIG. 11 is a bottom view of the slave and control portions of the device of FIG. 7, in accordance with an embodiment.

FIGS. 6A and 6B give an overview of example variations of the slave portion 70 of variations of embodiments of the present invention. As shown in FIGS. 6A and 6B, the slave portion 70 may include, among other components, an Extension/Retraction actuator portion 40 and a Pivoting/Swivel actuator portion 30 that may relate to the macro motions discussed in detail below. The instrument 4 and/or tool 7 that may be coupled with slave portion 70 may have a variety of components and functionalities. For example, the instrument and/or tool may include graspers, scalpels, scissors, tweezers and any other component suitable for the application. Further, the instrument 4 and/or tool 7 may include or correspond to any number of suitable control cylinders 100 appropriate for the application. The control cylinders 100 in the instrument 4 and/or tool 7 may be independently actuated or may work in tandem. Also, the instrument 4 and/or tool 7 may include multiple functions (controlled by one or more function control mechanisms 50c) and multiple instruments/tools. The instrument 4 and/or tool 7 may also be modular in nature and may allow the substitution or exchange of various components with various functionalities.

As shown in FIGS. 6A and 6B the slave portion 70 may include one or more control cylinders 100 depending on the number of desired motions and/or on the configuration of device 1. FIG. 6A shows the example slave portion 70 fixed to a stand 2 and FIG. 6B represents the example slave portion 70 without a stand 2. The configurations shown in FIGS. 6A and 6B are merely example. For example, there may be additional control cylinders 100 to those shown in the figures, wherein one or more control cylinders 100 correspond to one or more degrees of freedom in device 1 or a portion thereof. For example, in one aspect, each of the slave control cylinders 100 generally corresponds to at least one of the master control cylinders 100 of the control portion 50 of the device shown in FIGS. 2A and 2B. However, there need not be a one to one correspondence between control cylinders 100 in the slave and master or control portions. Each of the control cylinders 100 in the slave portion 70 is hydraulically coupled to some aspect of the master control portion 50, such as being hydraulically coupled to a corresponding master control cylinder 100.

FIG. 6A shows example hydraulic lines 600 that may connect aspects of the slave 70 and control portion 50 as described above and in other ways. Hydraulic lines 600 may be of any suitable material or have any suitable configuration. For example, hydraulic lines 600 may include plastic, rubber or other elastic material. Aspects of the hydraulic lines 600 may also include metal in any suitable form, including metal sheathing, weaving or metal reinforcement, for example, to control expansion of the lines under pressure, which thereby controls the transfer of motion or force from the master to the slave portion 70. Aspects of the hydraulic lines may also include other suitable materials including various polymeric materials as well as foils, glasses, or any other suitable material. Portions of the hydraulic lines 600 may be rigid and others may be suitably flexible, as needed. Portions of the hydraulic lines 600 may be transparent or opaque. Variations of embodiments of the invention disclosed herein may include any suitable number of hydraulic lines of any suitable construction or configuration. The hydraulic lines 600 (see, e.g., FIG. 1C) may also be made from a variety of materials, including plastics, rubbers and/or including various fibers or metal weavings. The hydraulic lines 600, corresponding control cylinders and spool valves may be of any suitable size and have any suitable inner and outer diameters for the particular applications. One type of hydraulic line may be used, or there may be a variety of types of hydraulic lines used in the same device 1000, for example, depending on the pressure of a given line. It is noted that drawings represented here of components relating to embodiments of the present invention are not necessarily to scale. In fact, the components and principles articulated here may operate on several different size scales alternatively or simultaneously.

The hydraulic fluid used with hydraulic lines 600 and with other example variations of embodiments of the present invention may be any suitable hydraulic fluid. This suitable hydraulic fluid may be, for example, any number of suitable oils, such as mineral oil. The hydraulic fluid may also be a fluid that is medically benign, such as saline or water. Any other suitable fluid may also be used, including fluids that are not medically benign.

Connections between the hydraulic lines may be obtained using spool valves, other valves, or other suitable hydraulic connections. These connections may include the use of O-rings or seal valves, for example. The connections may include other components (e.g., caps, pipes, sockets).

Although not depicted in FIGS. 6A and 6B, other lines besides hydraulic lines 600 (such as suction lines, irrigation lines, electrical lines, and fiber optic lines) that control movement of functions associated with slave portion 70, instrument 4, and/or tool 7, may similarly connect aspects of slave portion 70 and control portion 50. Additionally, one or more of these other lines may be further, routed to an instrument 4 and/or a tool 7 which is coupled with slave portion 70. A function control 50c may convey or control information or signals over one or more or these other lines to affect one or more functions associated with instrument 4 and/or tool 7.

FIGS. 7-11 show variations of the device 1000. Note that the device 1000 shown in FIGS. 7-11 includes several aspects not shown in FIGS. 1B-6B. For example, FIGS. 7-11 show a casing 140 covering certain aspects of the slave portion 70 of the device. It is to be understood that any of the gears, cylinders or other components shown herein may be covered by such a casing during operation or storage. The casing 140 may serve to protect the components from dust, wear or inadvertent contact with other objects, for example. The slave portion 70 of the device shown in FIGS. 7-11 also includes grip handles 2a and knobs 2b for fixing the slave portion 70 to some other object, including a stand 2. The grip handles 2a and knobs 2b may also be used to adjust the position of slave portion 70. Further, the slave portion 70 of FIGS. 7-11 is coupled with a single instrument 4 having a connected tool 7. It is to be understood that multiple instruments 4 and/or tools 7 may also be connected. In addition a single device may include multiple slave portions 70 and/or multiple control portions 50 as needed.

Macro Controls and Macro Motions

Overview

Figure 12A:
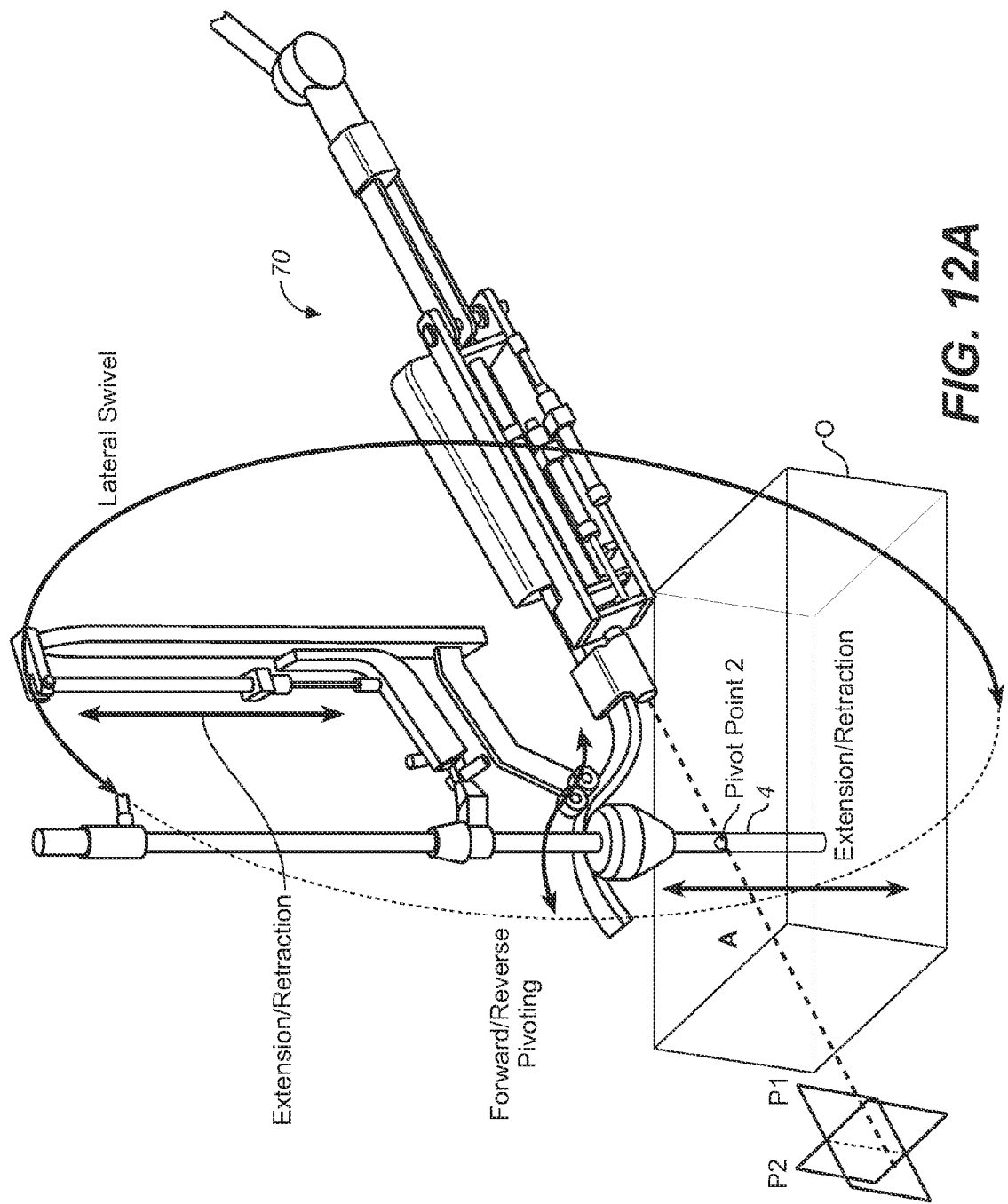
FIG. 12A is a perspective view of an aspect of the slave portion of the present system, illustrating an overview of three example macro degrees of freedom of the slave portion, in accordance with an embodiment.
Figure 12B:
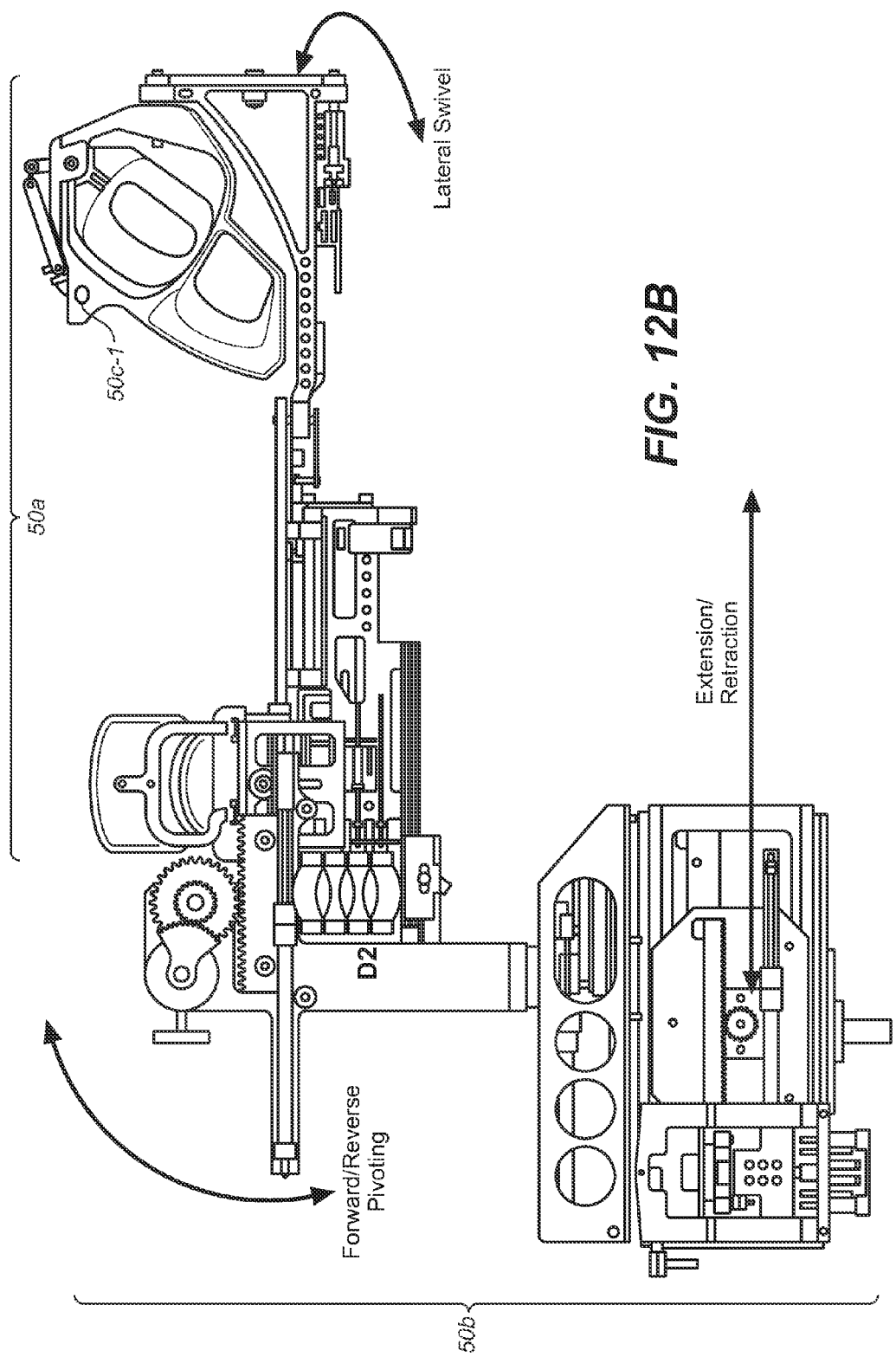
FIG. 12B is a side view of an aspect of the control portion of the system, illustrating an overview of how the three example macro degrees of freedom shown in FIG. 12A may be actuated in the control portion, in accordance with an embodiment.

FIG. 12A shows an overview of three example macro degrees of freedom in a variation of the slave portion 70 of the device in accordance with aspects and embodiments of the present invention. FIG. 12B shows an overview of how the three example macro degrees of freedom shown in FIG. 12A may be actuated in the control portion. These figures and discussion are meant as an introduction to the three example degrees of freedom which will be discussed in more detail with their associated controlling and actuating mechanisms in the following section. It should be noted that, while the example degrees of freedom are useful for certain applications, they are not meant to be exhaustive. Other degrees of freedom are within the scope of aspects and embodiments of the present invention. Indeed, it is possible to modify the existing apparatus as described to encompass either additional or fewer degrees of freedom, as needed. All such modifications should be considered within the scope of embodiments of the present invention.

In FIG. 12A, one of the example macro degrees of freedom shown is Forward/Reverse Pivoting of the instrument 4 and related components. Forward/Reverse Pivoting may allow instrument 4 to pivot about a central pivot point, such as Pivot Point 2 shown in FIG. 12A, in plane P1. This particular degree of freedom is useful for, among other things, positioning the instrument 4 about a particular area of interest in an operational environment O. For example, the Forward/Reverse Pivoting degree of freedom can be used to position a tool 7, such as a scalpel, on the end of the instrument 4 in a position appropriate for the making of an incision. Alternatively, Forward/Reverse Pivoting degree of freedom can be used to position tweezers on the end of the instrument 4 in a position appropriate for grasping a particular object (e.g., an organ or tissue). FIG. 12B shows how the Forward/Reverse Pivoting may be actuated, in particular by a swinging motion of the user's forearm in conjunction with the micro controls 50a.

In FIG. 12A, another of the example macro degrees of freedom shown is Lateral Swivel of the instrument 4 and related components. The Lateral Swivel may allow instrument 4 to swivel about axis A in plane P2. This particular degree of freedom is useful for, among other things, positioning the instrument 4 about a particular area of interest in an operational environment O. This particular degree of freedom may, for example, compliment the Forward/Reverse Pivoting motion such that the instrument 4 and related components are able to assume 180° of motion in the two orthogonal planes P1 and P2 that are perpendicular to axis A. The Lateral Swivel degree of freedom can be used, for example, to position a scalpel on the end of the instrument 4 in a position appropriate for the making of an incision. Alternatively, Forward/Reverse Pivoting degree of freedom can be used to position tweezers on the end of the instrument 4 in a position appropriate for grasping a particular object (e.g., an organ or tissue). FIG. 12B shows how the Forward/Reverse Pivoting may be actuated, in particular by a lateral sweeping motion of the user's forearm in conjunction with the micro controls 50a.

In FIG. 12A, another of the example macro degrees of freedom shown is Extension/Retraction of the instrument 4 and related components. Extension/Retraction may allow instrument 4 to be brought closer to or further away from the operational environment O. This particular degree of freedom may, for example, allow the instrument 4 to be retracted a safe distance from objects in the operating environment while it is repositioned using the Forward/Reverse Pivoting and Lateral Swivel motions. Once the instrument 4 has been repositioned, it may be brought back in contact or in close proximity with the operational environment O using the Extension/Retraction degree of freedom. FIG. 12B shows how Extension/Retraction may be actuated, in particular by a forward or backward motion of the micro control 5a assembly and corresponding motion of portions of the macro control assembly 50b.

FIG. 12B also illustrates one embodiment of a function control in the form of knob 50c-1, which a user may manipulate or adjust, such as by spinning with a thumb, in order to engage or control a function that is associated with instrument 4 and/or tool 7.

Details of the Macro Controls

FIGS. 13A-17E highlight details of the macro controls and their operation. In the example variation of the device 1000 shown in FIGS. 13A-17E there are three macro controls controlling three associated macro degrees of freedom. However, it is to be understood that this is merely example. There could be any suitable number of macro controls controlling any associated number of degrees of freedom. Further, although in the example variation each macro control has an associated control cylinder 100 and an associated single degree of freedom, it is to be understood that other combinations are possible within the scope embodiments of the present invention. For example, macro controls may act in combination on the same control cylinder or on the same combination of control cylinders. This may control one or more degrees of freedom simultaneously.

Clutch Mechanism

Figure 13A:
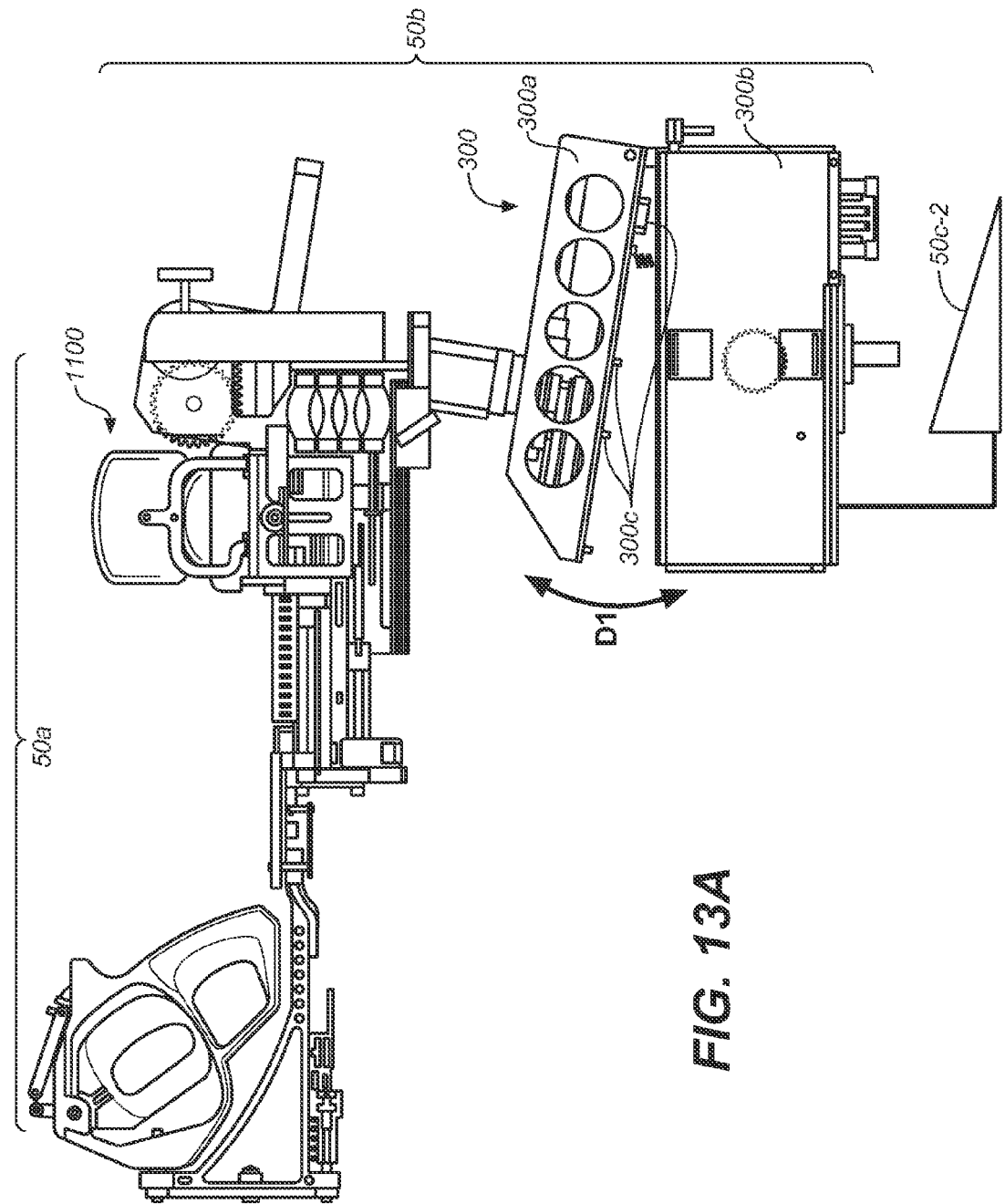
FIG. 13A is a side view of an aspect of the control portion of the system, including a clutch safety mechanism that may be part of the macro controls, in accordance with various embodiments of the invention.

FIG. 13A highlights an optional clutch safety mechanism 300 that prevents or enables operation of the macro controls 50b and FIG. 13B shows a close up of the clutch safety mechanism 300 from the opposite viewpoint. Generally, the clutch safety mechanism 300 includes two major components, an upper portion 300a and a lower portion 300b. Note that the control cylinder 100 belonging to the lower portion 300b is related to one of the three degrees of freedom of the macro controls 50b. This control cylinder is shown in a different position in FIGS. 13A and 13B. However, the relative position of the control cylinder 100 is not necessarily related to the operation of the clutch safety mechanism 300. The clutch safety mechanism 300 can temporarily disconnect the hydraulic systems between the macro controls 50b and their corresponding control cylinders 100 on the slave portion 70 of the device. Alternatively, the clutch safety mechanism 300 may be purely mechanical and disconnect the macro controls 50b from their corresponding control cylinders 100 on the slave portion 70 in a purely mechanical fashion.

Generally, in one embodiment, when the device 1000 is not in operation, the clutch safety mechanism 300 is in the upright position shown in FIG. 13A. The upright position may be displaced from horizontal by the arc D1. The arc D1 may be any suitable length. The upright position generally disengages the macro controls 50b from their corresponding control cylinders 100 on the slave portion 70. As shown in FIG. 13A, the upright position may be the default position taken by clutch safety mechanism 300 when not in use. The upright position may be assumed automatically, such as by a biasing mechanism, which may include one or more of a spring, a lever, a hinge and/or other suitable mechanisms for positioning the clutch to disconnect the hydraulic system when the user's arm is not present in arm holder assembly 1100 to press downwardly on the upper position 300a of the clutch safety mechanism 300. In the upright position, hydraulic lines between the macro controls 50b and their corresponding control cylinders 100 in the slave portion 70 may be disconnected, for example, by valves, plungers or other mechanics 300c that interrupt the fluid communication between the two portions. Disconnecting the macro controls 50b from their corresponding control cylinders 100 in the slave portion 70 can prevent inadvertent actuation of the degrees of freedom associated with the macro controls 50b when the device 1000 is not in use. This can prevent damage to the system by, for example, inadvertent actuation of one of the control cylinders 100 of the slave portion 70 bringing the instrument 4 which is coupled with slave portion 70 into contact with an object in the operational environment O, or a storage environment, that causes damage (e.g., from scraping, gouging or smashing contact). Disengaging the macro controls 50b in the upright position prevents such contact or inadvertent motion. It should be understood, however, that the clutch mechanism may be configured to disengage the hydraulic system at positions of the macro controls 50b other than the upwardly biased position.

In one embodiment of an upwardly biased clutch mechanism, when the user places his or her arm in the arm holder assembly 1100 and presses downwardly on the cradle, this downward force is transmitted to the upper portion 300a of the clutch safety mechanism 300. This force then brings the lower 300b and upper 300a portions of the clutch safety mechanism 300 into contact. This generally positions the valves, plungers or other mechanics 300c to allow either hydraulic or mechanical communication between the macro controls 50b and their corresponding cylinders 100 in the slave portion 70 of the device. The engaged position is shown, for example, in FIG. 14A. Typically, in the engaged position, the upper 300a and the lower 300b portions of the clutch safety mechanism 300 are in direct contact. However, other configurations are also within the scope embodiments of the present invention. For example, the clutch safety mechanism 300 may be adjustable so that the engaged position can be adjusted according to user preference and/or to maximize user comfort. Alternatively, the engaged position may be accessed by more complicated motions than simply pressing down on the arm holder assembly 1100. For example, the engaged position may be accessed by simultaneously pressing down on the arm holder assembly 1100 and moving the control portion in a given direction, such as laterally (not shown). More complicated motions to access the engaged position may also be possible.

FIG. 13A also illustrates one embodiment of a function control in the form of foot pedal 50c-2, which a user may manipulate or adjust, such as by depressing with a foot of the user, in order to engage or control a function that is associated with instrument 4 and/or tool 7.

First Example MACRO Degree of Freedom

Forward/Reverse Pivoting

Figure 14A:
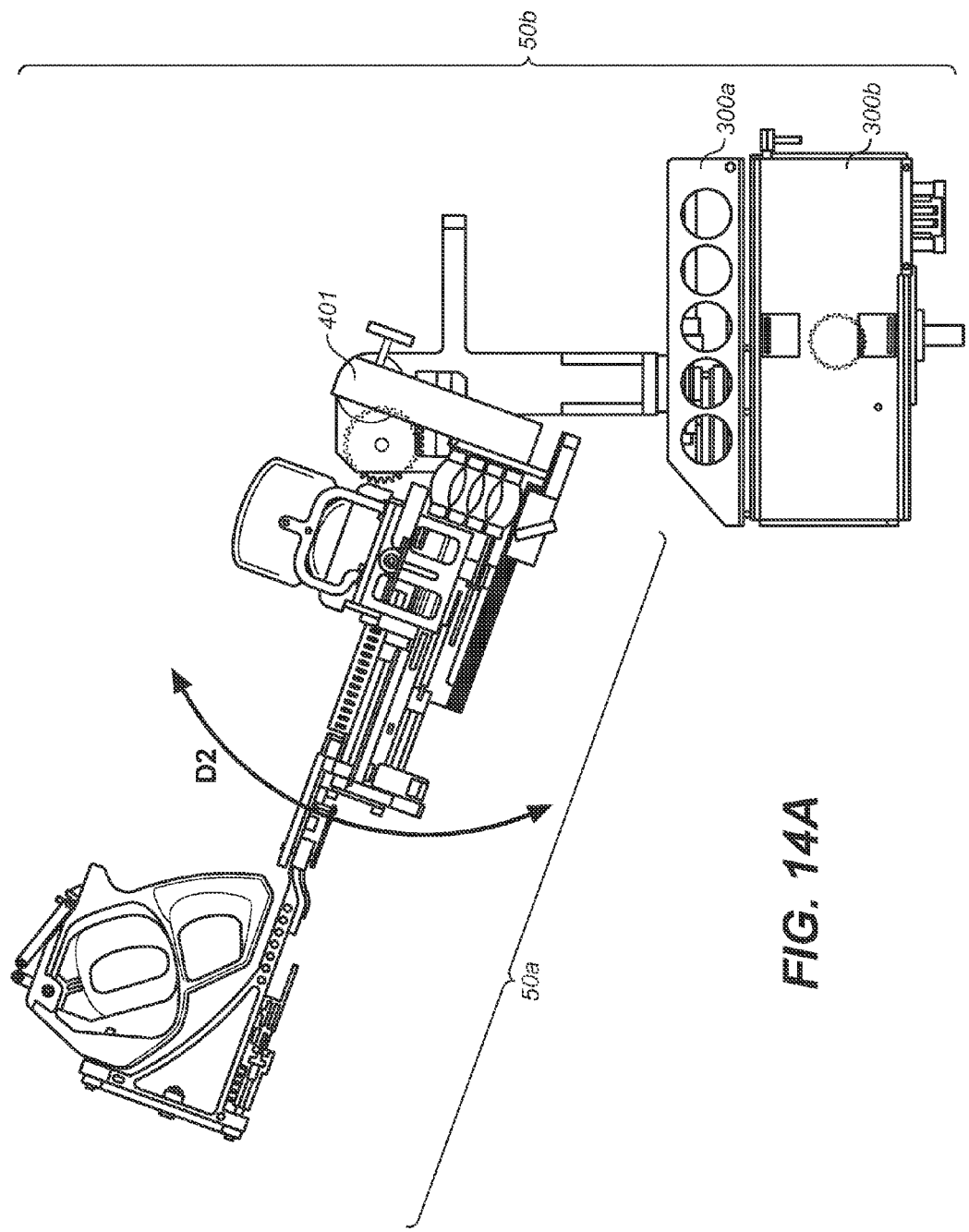
FIGS. 14A-14C are side views of the control portion of the system, illustrating how an example forward/reverse pivoting motion may be actuated by the macro controls, in accordance with an embodiment of the present invention.
Figure 14B:
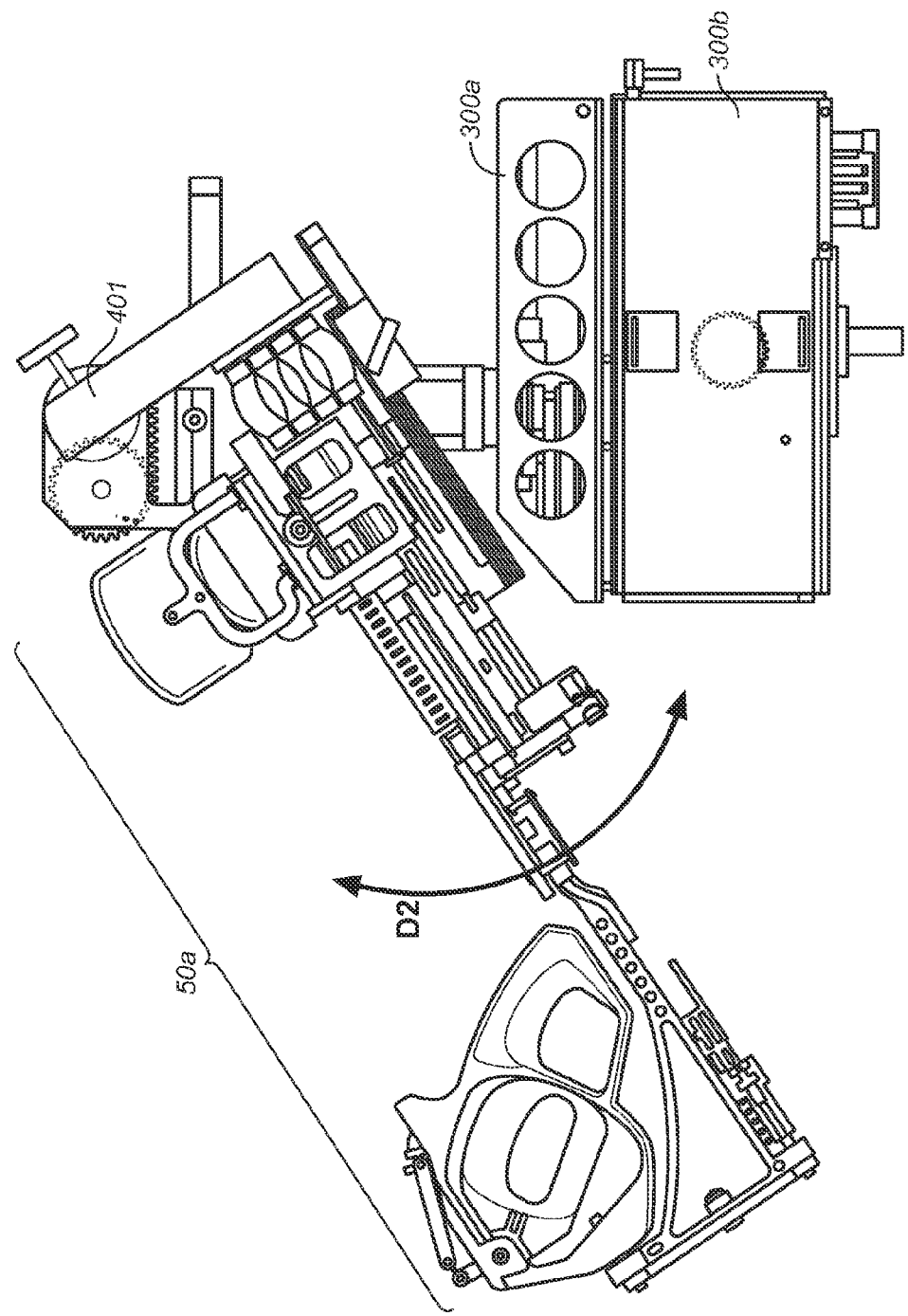
Figure 14C:
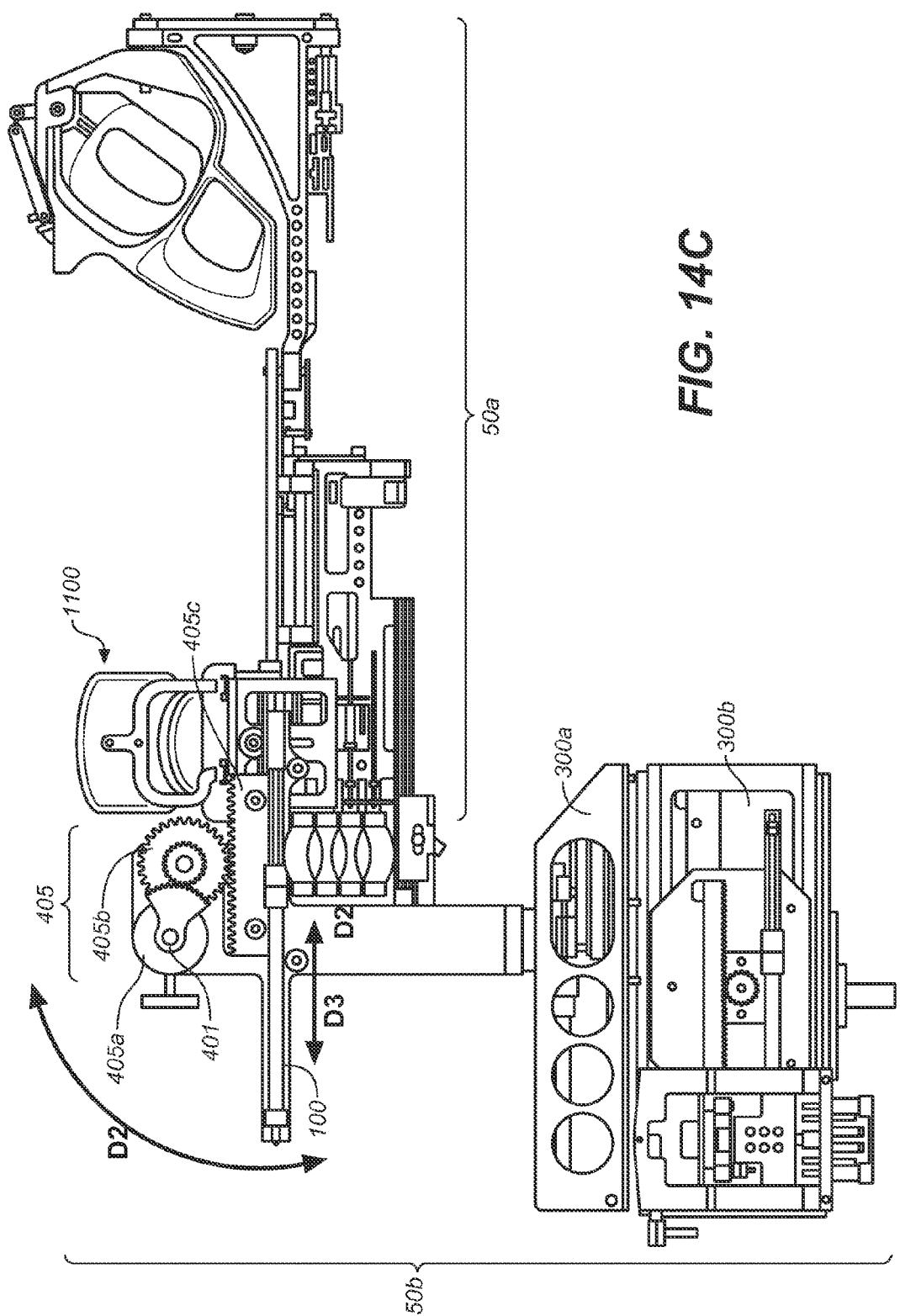
Figure 14D:
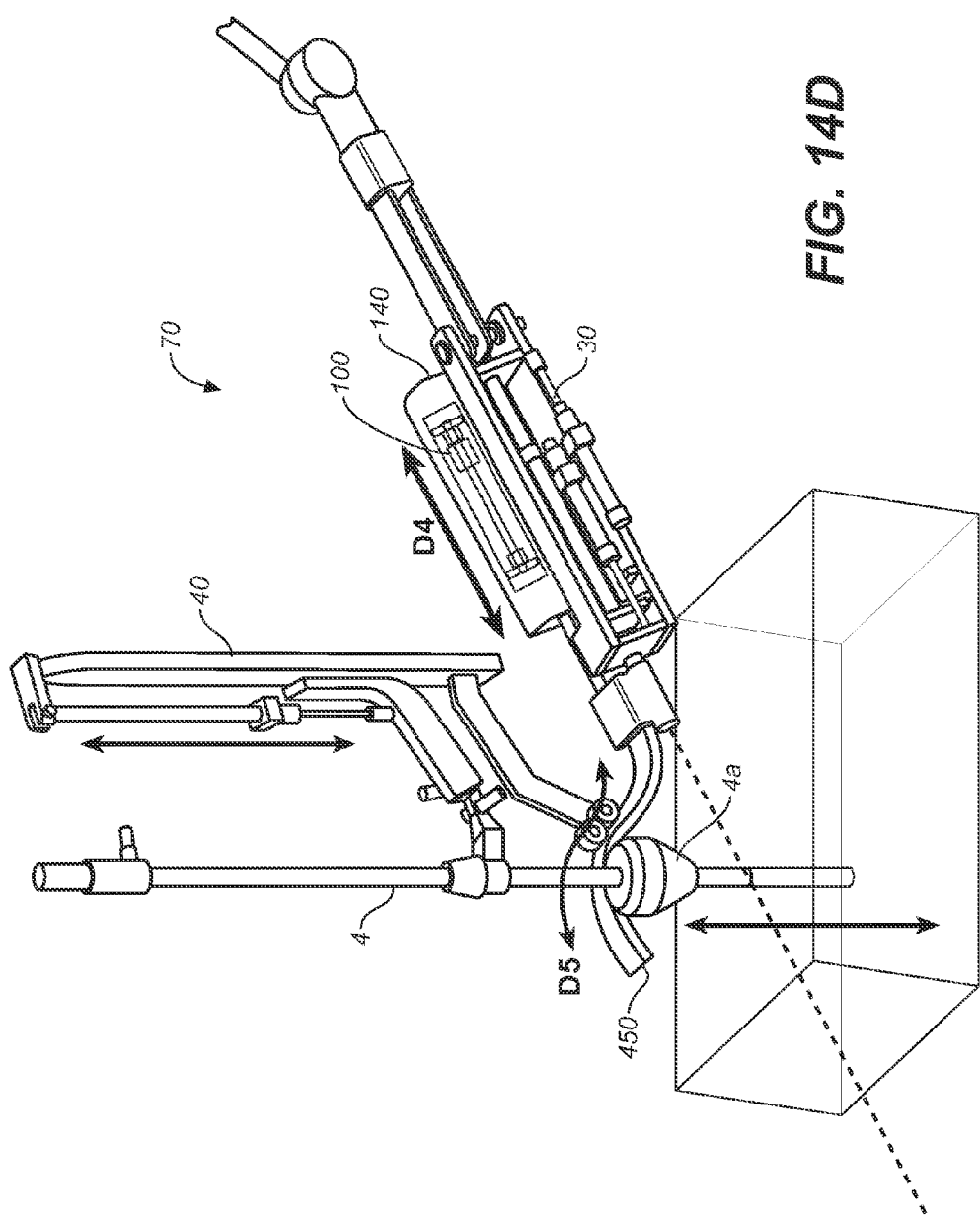
FIGS. 14D and 14E are perspective views of parts of the slave portion of the system, illustrating a resultant example forward/reverse pivoting motion in the slave portion that may be actuated by the motion shown in FIGS. 14A-14C, in accordance with an embodiment.
Figure 14E:
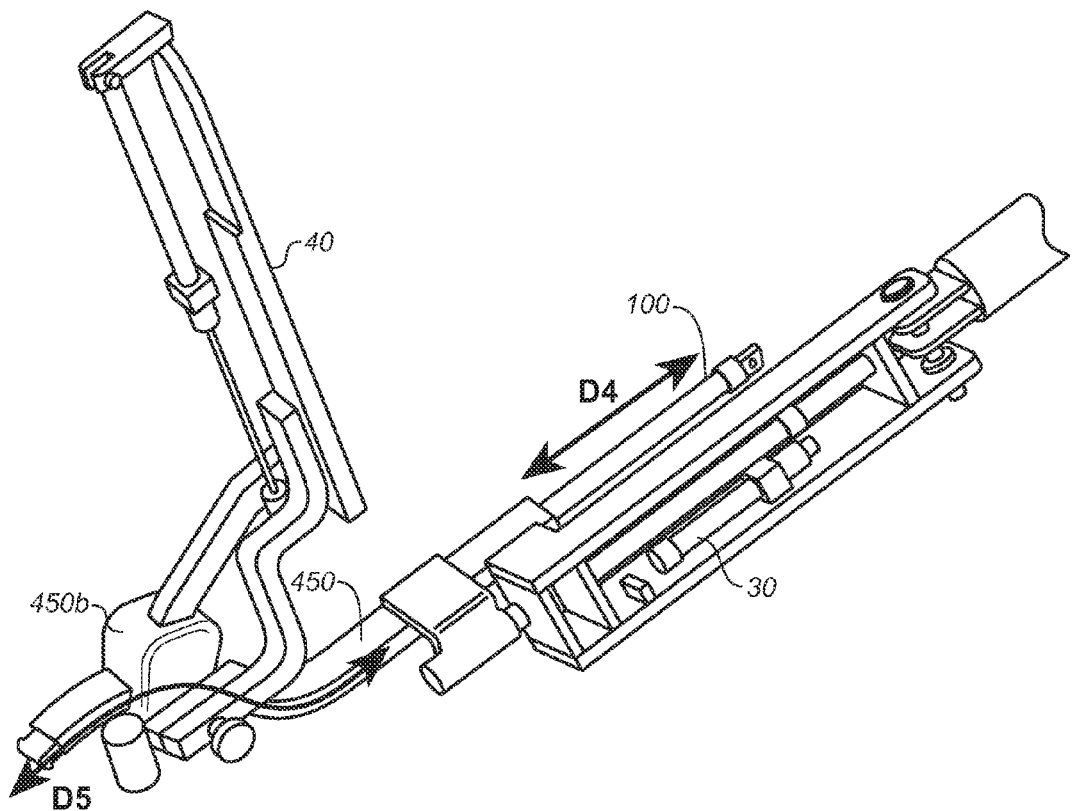

FIGS. 14A-14E highlight a first example degree of freedom of the macro controls associated with a forward translation of the slave portion 70. FIGS. 14A-14C show how the motion may be actuated in the macro controls 50b and FIGS. 14D and 14E show an example resultant motion in the slave portion 70 and FIG. 14F highlights that motion along the curved track of the slave portion 70. FIGS. 15A and 15B show the resultant forward/reverse pivoting motion of the instrument 4 which is coupled with the slave portion 70.

As shown in FIGS. 14A-14C, the user may actuate a forward translation of the slave portion 70 by swiveling the entire micro controls 50a throughout arc D2. As shown in FIGS. 14A-14C, the micro controls 50a may swivel about pivot point 401. FIG. 14C shows an example gear setup of transmission assembly 405 that may be used to translate this swiveling motion of the micro controls 50a about the arc D2 to a linear motion of a control cylinder 100. For example, swiveling the micro controls 50a about pivot point 401 may cause gear 405a to turn and engage gear 405b. Gear 405b may then engage linear gear 405c which can be fixed to the control cylinder 100, as shown in FIG. 14C. This gear motion, in either direction, then may cause the piston of the control cylinder show in FIG. 14C to move in the lateral direction D3, pumping hydraulic fluid to a corresponding control cylinder 100 on the slave portion 70 of the device (as shown and discussed in the context of FIGS. 5A and 5B).

The control cylinder 100, the micro controls 50a and the gear setup of transmission assembly 405 may be configured such that any suitable combination of motions is possible. For example, moving the micro controls 50a in a clockwise direction D2 about pivot point 401 may ultimately cause hydraulic fluid to be pumped to the slave portion 70 of the device. In this case, moving the micro controls 50a in a counter clockwise direction D2 about pivot point 401 may ultimately cause hydraulic fluid to be pumped to the control portion of the device. Alternatively, moving the micro controls 50a in a clockwise direction D2 about pivot point 401 may ultimately cause hydraulic fluid to be pumped to the control portion of the device. In this case, moving the micro controls 50a in a counter clockwise direction D2 about pivot point 401 may ultimately cause hydraulic fluid to be pumped to the slave position of the device.

FIGS. 14D and 14E show how the motion of the micro controls 50a described in FIGS. 14A-4C may be translated into motion of the slave portion 70 of the device. Hydraulic fluid is either pumped in or out of the control cylinder 100 in FIGS. 14D and 14E on the slave portion 70 of the device according to motion of the micro controls 50a discussed above with reference to FIGS. 14A-14C.

In FIG. 14D, the control cylinder 100 receiving or expelling hydraulic fluid associated with the first example degree of freedom is shown in an inset. Typically, the control cylinder 100 will be housed in a casing 140, which is also shown in FIG. 14D. FIG. 14E shows the setup in FIG. 14D without the casing 140 and without the instrument 4. As shown in FIGS. 14D and 14E, the control cylinder 100 may be mechanically coupled to a track 450 in which a chain 450a may translate. The chain 450a and the track 450 are shown in more detail with respect to the casing 140 in FIG. 14F.

Generally, the chain 450a may be coupled on one end to an instrument holder 4a. An example coupling 450b is shown in more detail in FIG. 14E. The coupling 450b may have any suitable form for connecting the instrument holder 4a to the chain 450a such that, for example, the instrument holder 4a moves as the chain 450a slides along the track. For example, coupling 450b may include a carriage having wheels that ride along track 450. In some embodiments, track 450 may include a groove or a rail to guide the carriage and/or wheels. In turn, the other end of the chain 450a may be coupled to the control cylinder 100 shown in FIG. 14E such that motion of the control cylinder 100 (see FIG. 5A) pushes or pulls the chain 450a along the track 450.

Figure 14F:
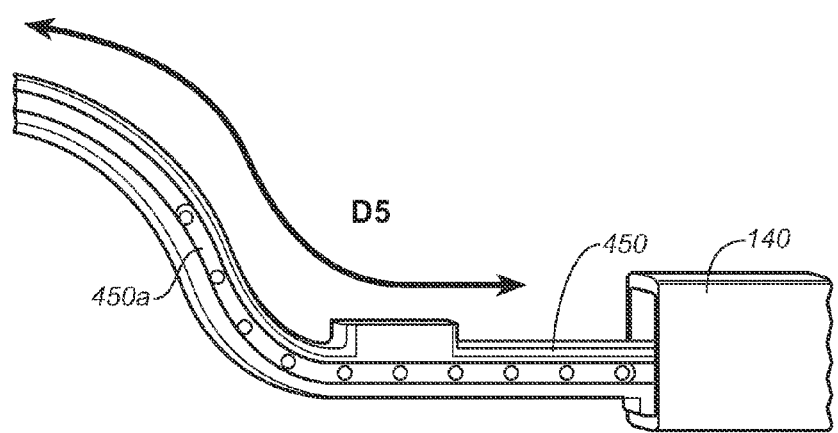
FIG. 14F is a close-up side view of a curved track part of the slave portion of the system, illustrating the example forward/reverse pivoting motion along the curved track of the slave portion shown in FIGS. 14D and 14E, in accordance with an embodiment.
Figure 15A:
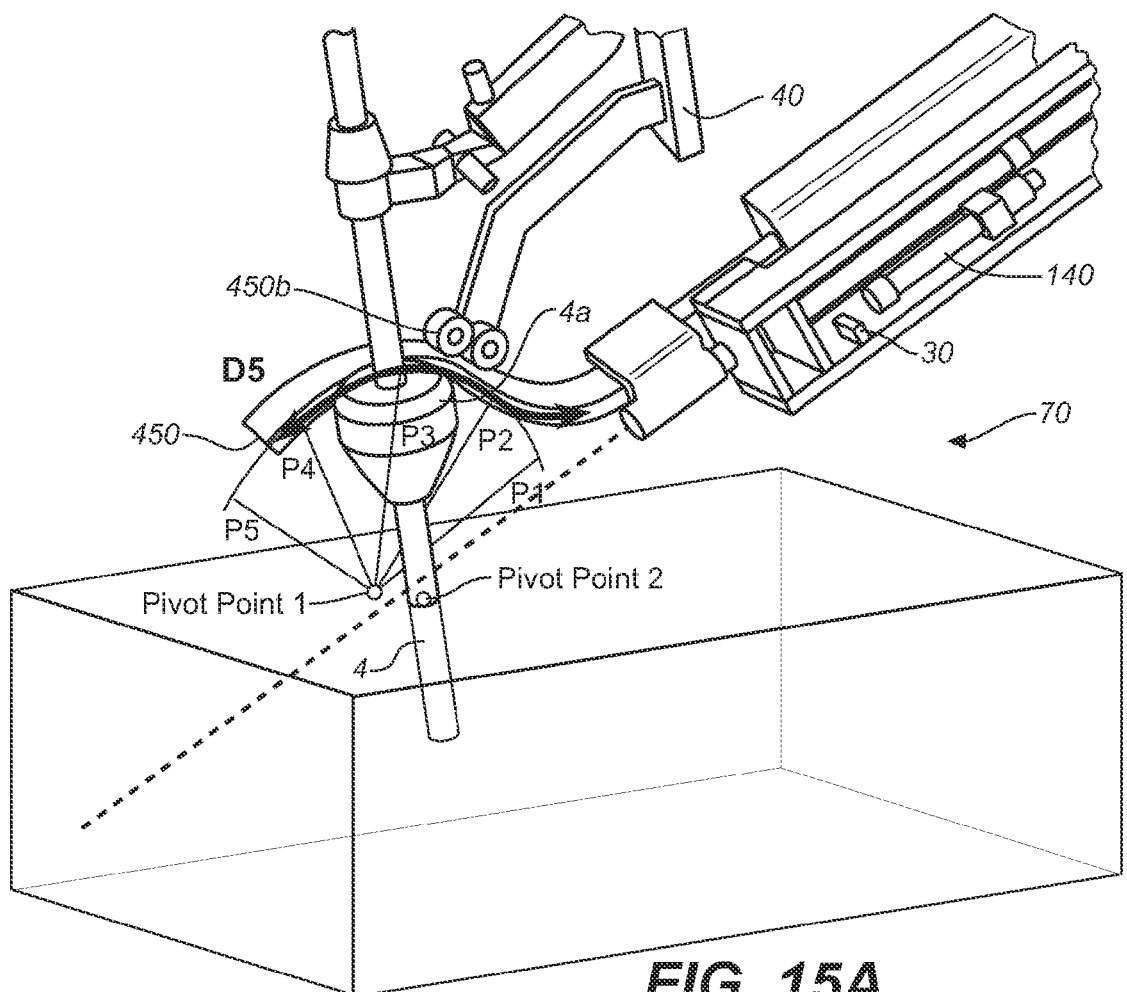
FIGS. 15A and 15B are partial perspective views of the slave portion of the system, illustrating the example forward/reverse pivoting motion of the tool of the slave portion that may be actuated by the motion shown in FIGS. 14A-14C, in accordance with an embodiment.
Figure 15B:
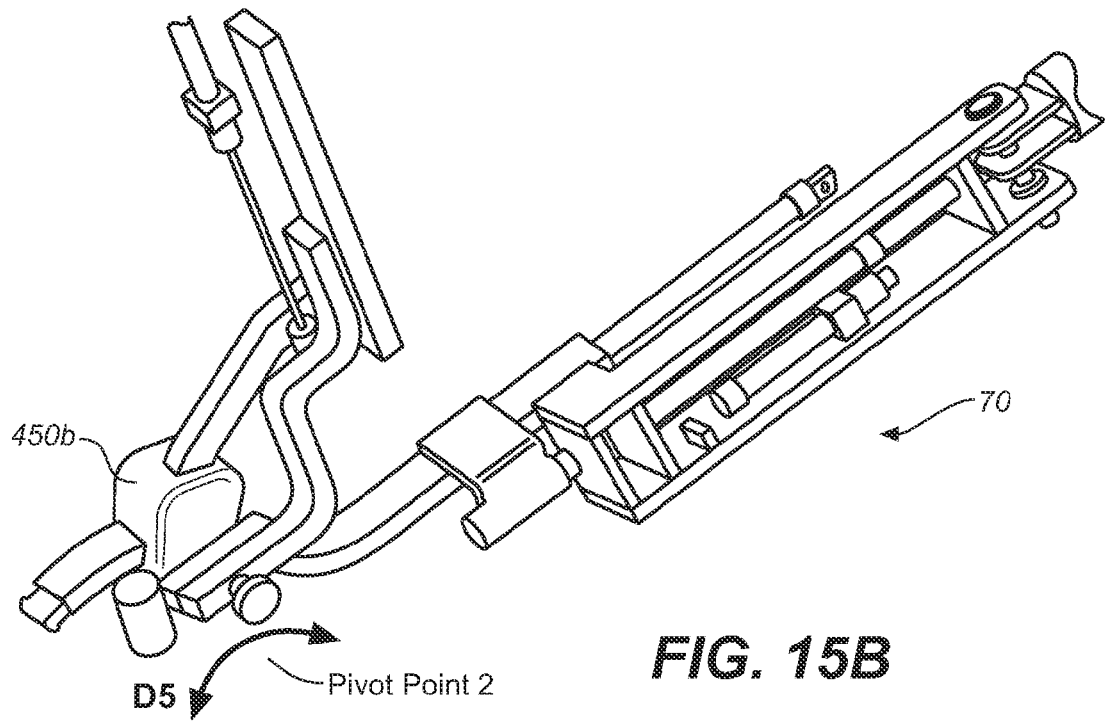

In general, a piston head and shaft of the control cylinder may move along the direction D4 shown in FIGS. 14D and 14E, causing the chain 450a to slide along direction D5 shown in FIGS. 14D-14F. FIG. 15A shows an example resultant motion of the instrument 4 and the instrument holder 4a in response to actuation by the motion of the control cylinder 100 along direction D4. FIG. 15B highlights the pivoting motion of the coupling 450b along direction D5. As shown in FIGS. 15A and 15B, the structure of the curved shape of the track 450 causes coupling 450b and, therefore, the instrument 4, to pivot about an effective Pivot Point. For example, as the chain 450a moves away from the casing 140 along direction D5, the mechanical coupling 450b sweeps through a series of positions P1-P5 about the Pivot Point 1. This causes the instrument 4 and the instrument holder 4a to sweep through the series of positions about Pivot Point 2. Since the chain may be positioned such that the mechanical coupling 450b adopts any of the positions P1-P5, or any other suitable position along D5, the instrument 4 may effectively adopt any position about the Pivot Point 2. This may allow the instrument 4 and the user U to operate on any portion of the operational environment O that may be accessed with such motion.

Second Example MACRO Degree of Freedom

Lateral Swivel

Figure 16B:
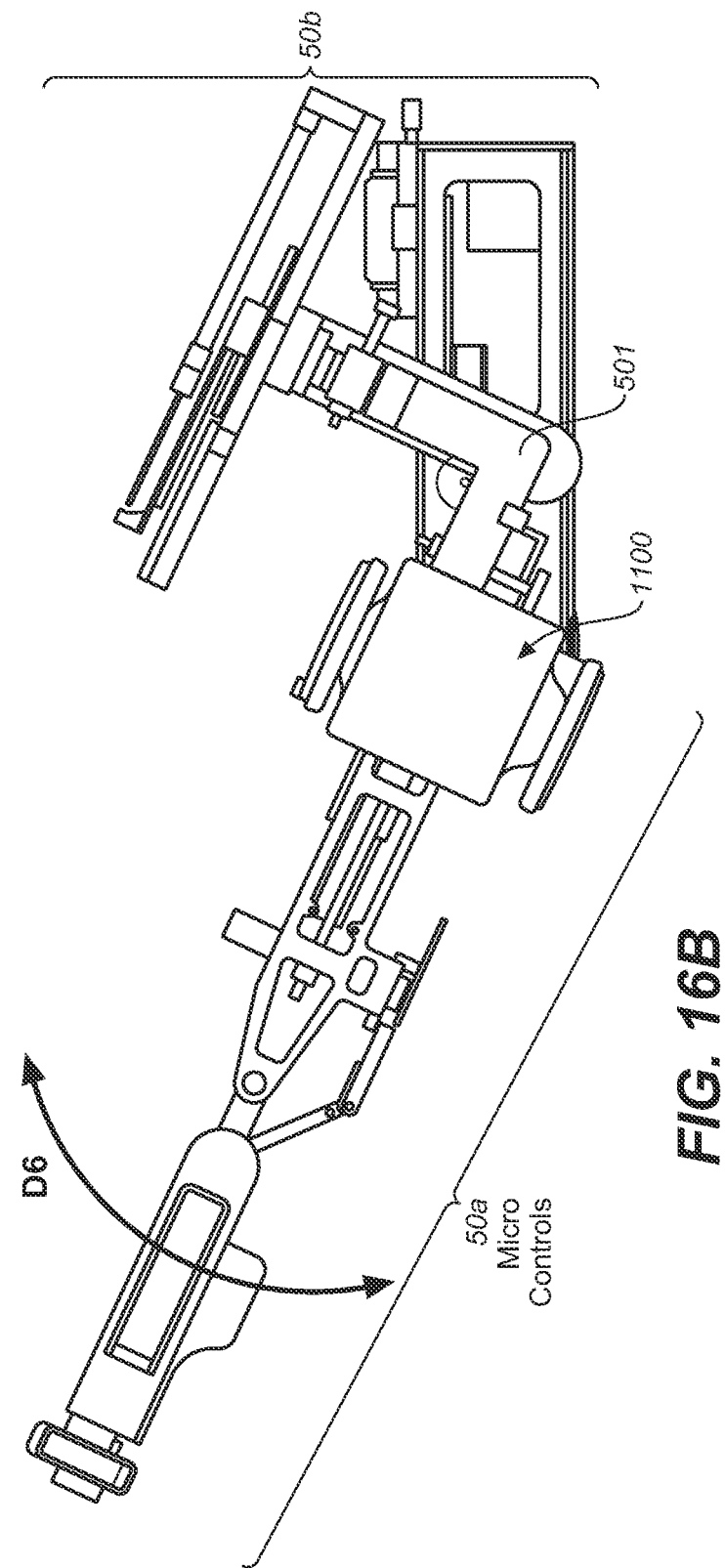
Figure 16C:
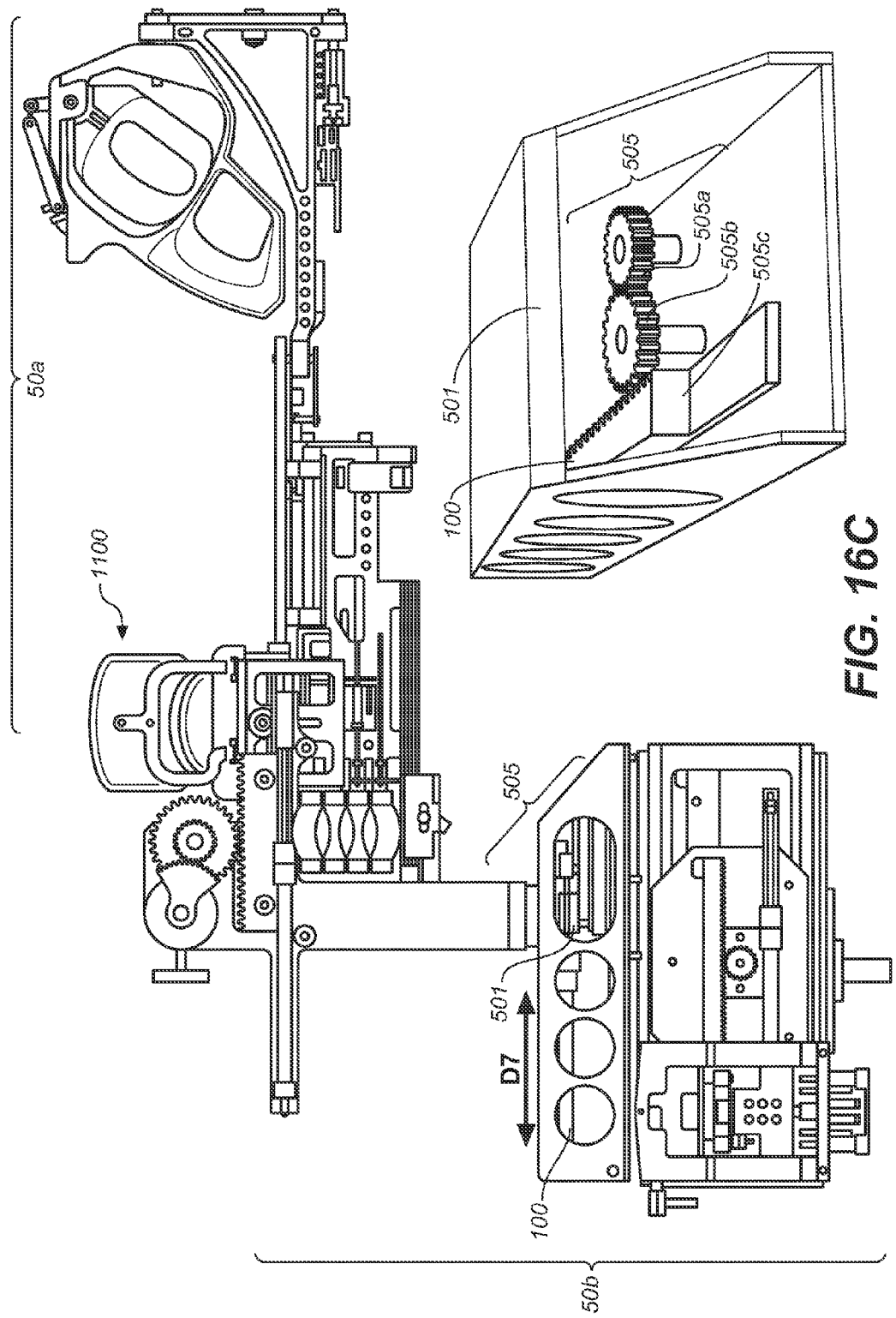
Figure 16D:
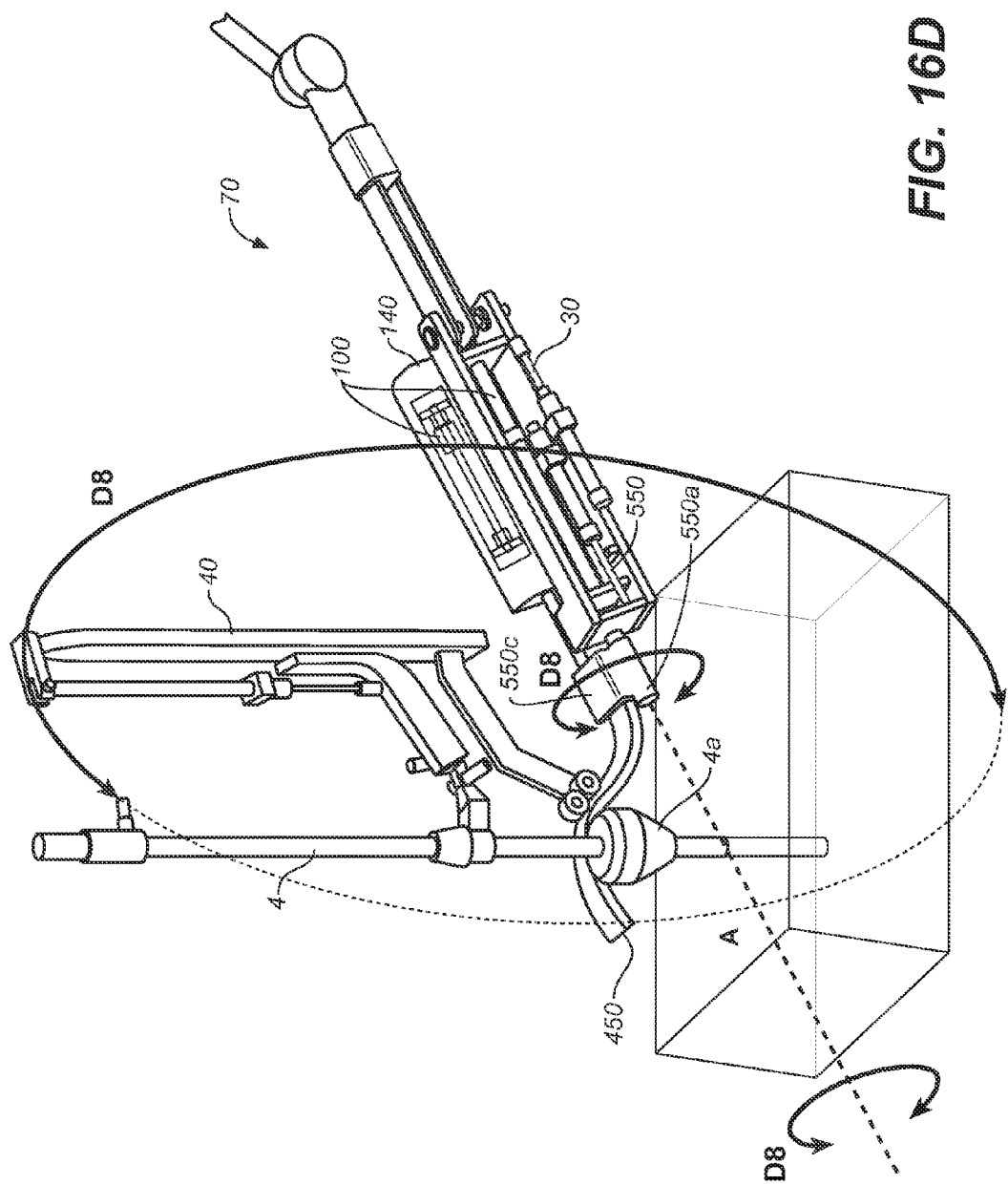
FIGS. 16D and 16E are perspective views of the slave portion illustrating a resultant example lateral swivel motion in the slave portion that may be actuated by the motion shown in FIGS. 16A-16C, in accordance with an embodiment.
Figure 16E:
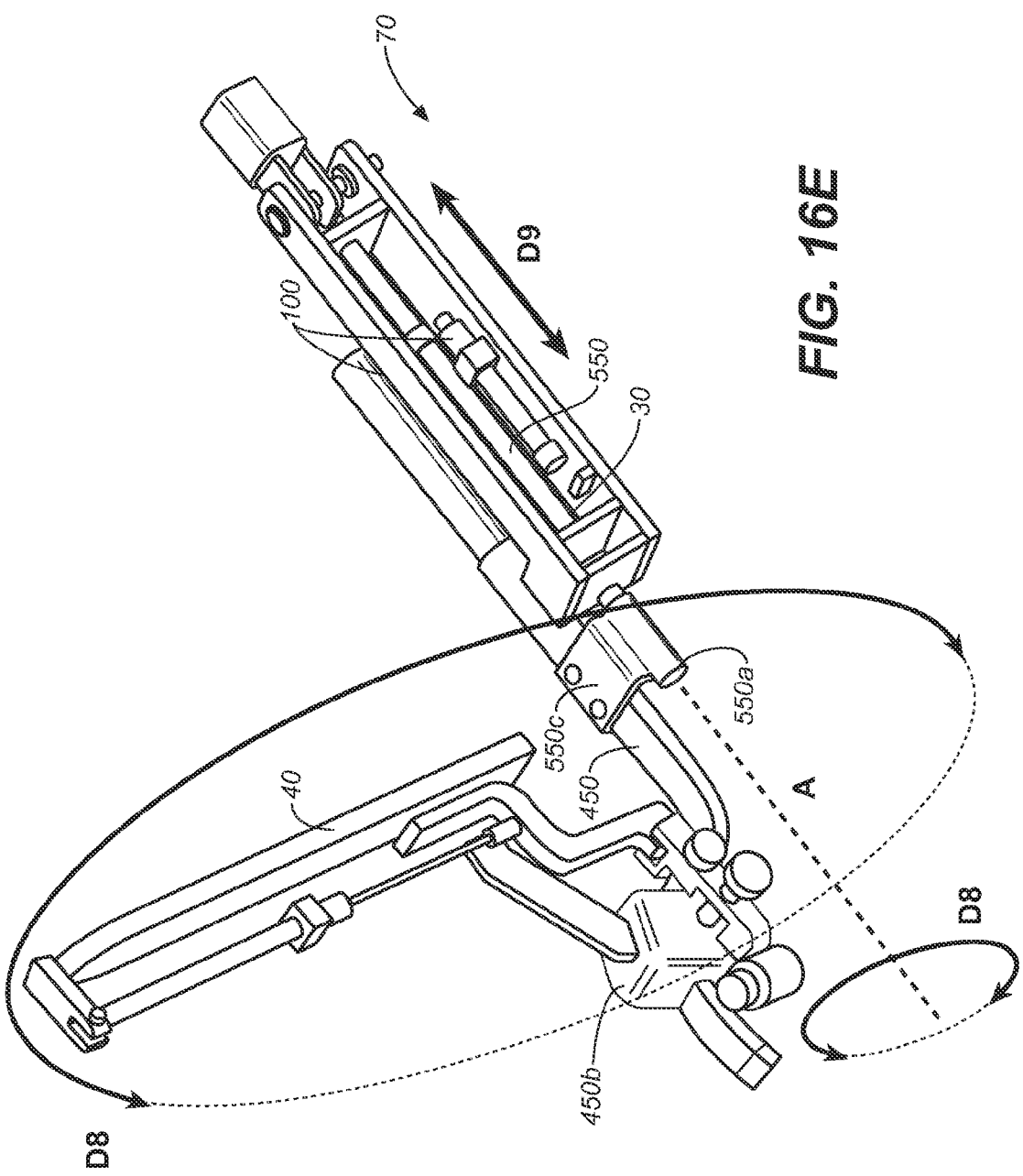

FIG. 16A-16F highlight a second example degree of freedom of the macro controls associated with a lateral swivel of the slave portion 70. FIGS. 16A-16C show how the motion may be actuated in the macro controls 50b and FIGS. 16D and 16E show an example resultant motion in the slave portion 70. FIG. 16F highlights an example screw mechanism that may actuate the example lateral swivel motion.

As shown in FIGS. 16A-16F, the user may actuate a lateral swivel, e.g., a rotation in a plane substantially perpendicular to axis A (see FIGS. 16D and 16E) of the slave portion 70 by swiveling the entire micro controls 50a throughout arc D6 about pivot point 501. FIG. 16C shows an example gear setup of transmission assembly 505 that may be used to translate this swiveling motion of the micro controls 50a about the arc D6 to a horizontal motion of a control cylinder 100. The INSET in FIG. 16C shows another view of example gears in the gear setup of transmission assembly 505. For example, swiveling the micro controls 50a may swivel gear 505a shown in the INSET. Gear 505a may then engage gear 505b, which in turn can engage linear gear 505c, which can be fixed to the control cylinder 100. This series of gear motion, in either direction, then may cause the piston of the control cylinder 100 to move in the lateral direction D7, pumping hydraulic fluid to a corresponding control cylinder 100 on the slave portion 70 of the device (as shown and discussed in the context of FIGS. 5A and 5B).

The control cylinder 100, the micro controls 50a and the gear setup of transmission assembly 505 may be configured such that any suitable combination of motions is possible. For example, moving the micro controls 50a in a clockwise direction along arc D6 about pivot point 501 may ultimately cause hydraulic fluid to be pumped to the slave portion 70 of the device. In this case, moving the micro controls 50a in a counter clockwise direction along arc D6 about pivot point 501 may ultimately cause hydraulic fluid to be pumped to the control portion of the device. Alternatively, moving the micro controls 50a in a clockwise direction along arc D6 about pivot point 501 may ultimately cause hydraulic fluid to be pumped to the control portion of the device. In this case, moving the micro controls 50a in a counter clockwise direction along arc D6 about pivot point 501 may ultimately cause hydraulic fluid to be pumped to the slave portion 70 of the device.

FIGS. 16D and 16E show how the macro motion described in FIGS. 16A-C may be translated into motion of the slave portion 70 of the device. In an embodiment, an example setup in FIG. 16D includes two control cylinders 100 (one is shown in the inset because it would otherwise be obscured by other components, and the other is visible). In this embodiment, in between the control cylinders is a screw member 550 that is attached to a shaft 550a. Hydraulic fluid is either pumped in or out of the control cylinders 100 in FIGS. 16D and 16E on the slave portion 70 of the device according to macro motions discussed above with reference to FIGS. 16A-16C.

More specifically, in FIG. 16D, the control cylinders 100 receiving or expelling hydraulic fluid associated with the second example degree of freedom are shown. FIG. 16E shows the setup in FIG. 16D without the casing 140 and without the instrument 4. As shown in FIGS. 16D and 16E, the control cylinders 100 may be coupled to a screw member 550, itself coupled to a shaft 550a. Axis A is the axis of rotation for the shaft 550a. The shaft 550a may additionally be coupled to a track 450 via coupling 550c, such as a link. Coupling 550c between the shaft 550a and the track 450 allows motion in the screw to ultimately be translated to the instrument 4 because the instrument 4 is coupled to the instrument holder 4a, which is movably connected to the track 450.

The coupling 550c may have any suitable forth for connecting shaft 550a to track 450 such that, for example, rotating the shaft 550a in the direction D8 about axis A ultimately rotates the track 450 in the same direction. Since the instrument 4 and holder 4a are coupled to the track 450, this motion ultimately turns the instrument 4 and holder 4a in the direction D8 as well.

FIG. 16F shows a more detailed view of the screw member and its coupling to the control cylinders 100. In addition to being coupled to the shaft 550a, the screw member 550 may have threads 550d that mate with opposing threads in a screw receiving member 552. Generally, though not exclusively, the screw receiving member 552 is coupled to the two control cylinders 100 such that when the two control cylinders 100 are moved in response to the flow of hydraulic fluid from actuation of the control portion of the device, the screw receiving member 552 moves with the control cylinders 100. In general, the control cylinders 100 may move along the direction D9 (FIG. 16E) causing the screw member 550 to rotate in direction D8, which ultimately correspondingly rotates instrument 4.

The shaft 550a may be rotated such that the instrument 4 is positioned at any angle in the 360 degrees of rotation along D8 about axis A. This may allow the instrument 4 and the user U to operate on any portion of the operational environment O that may be accessed with such motion.

Third Example MACRO Degree of Freedom

Extension/Retraction

Figure 17B:
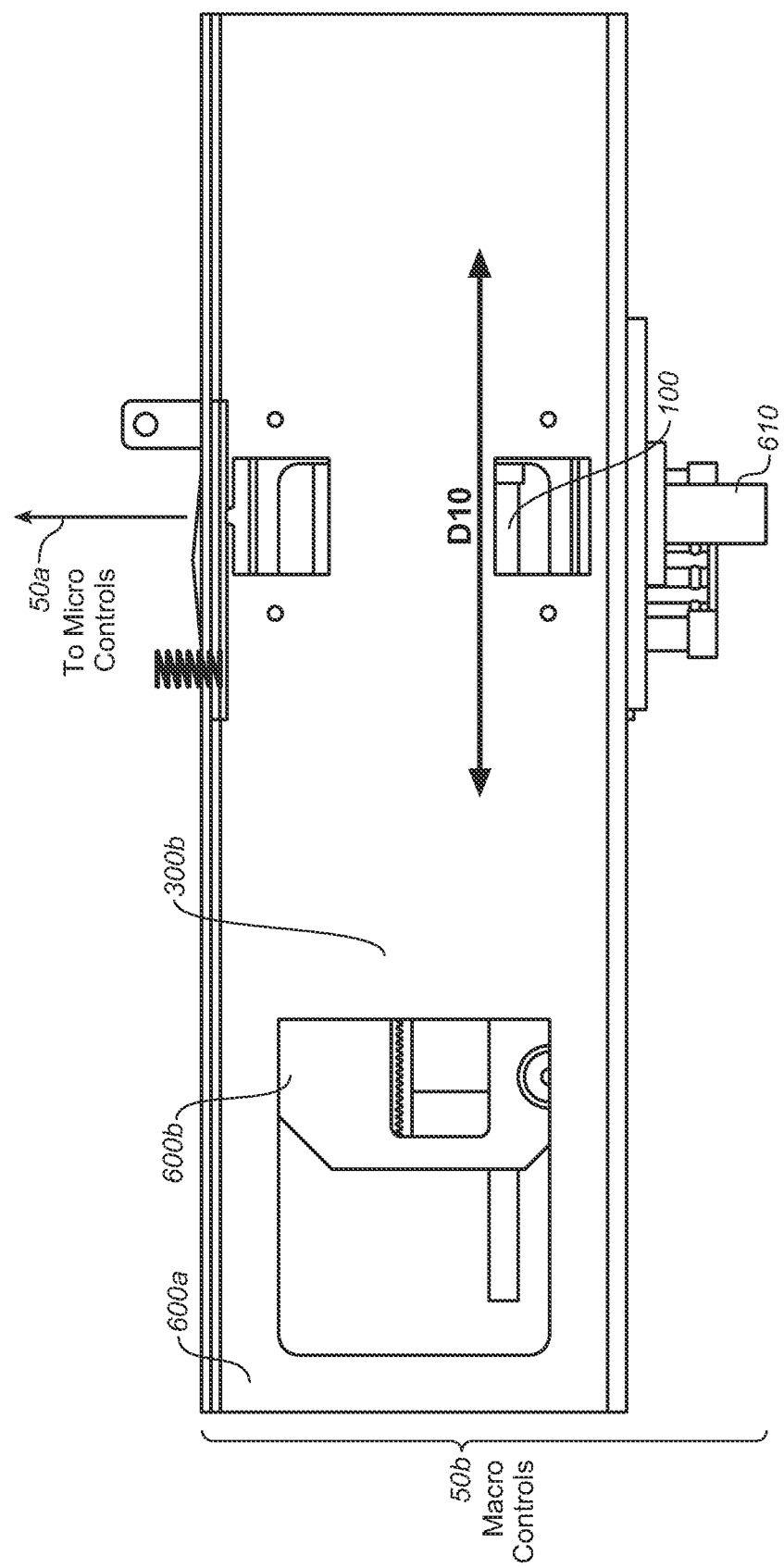
Figure 17C:
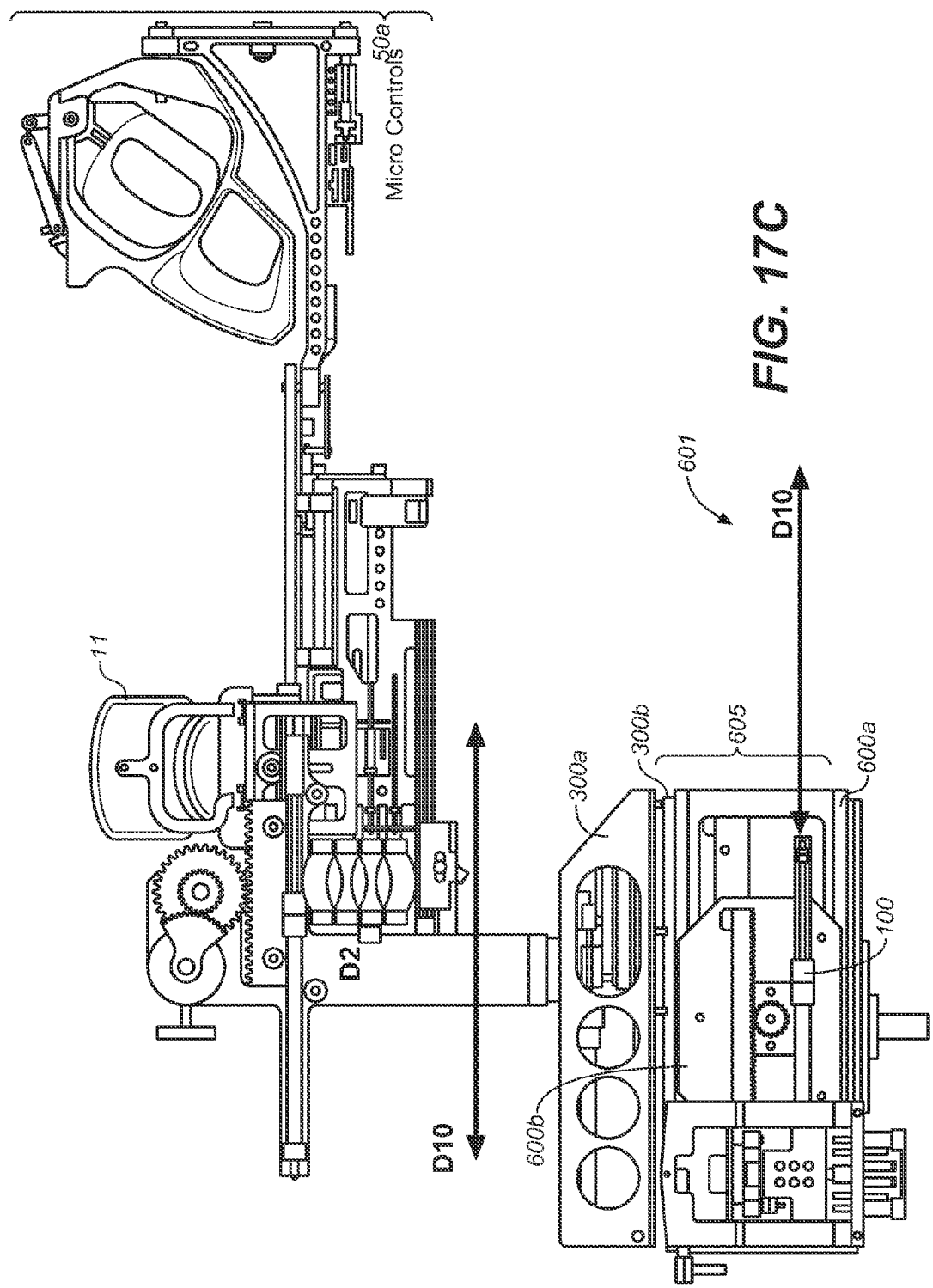
Figure 17E:
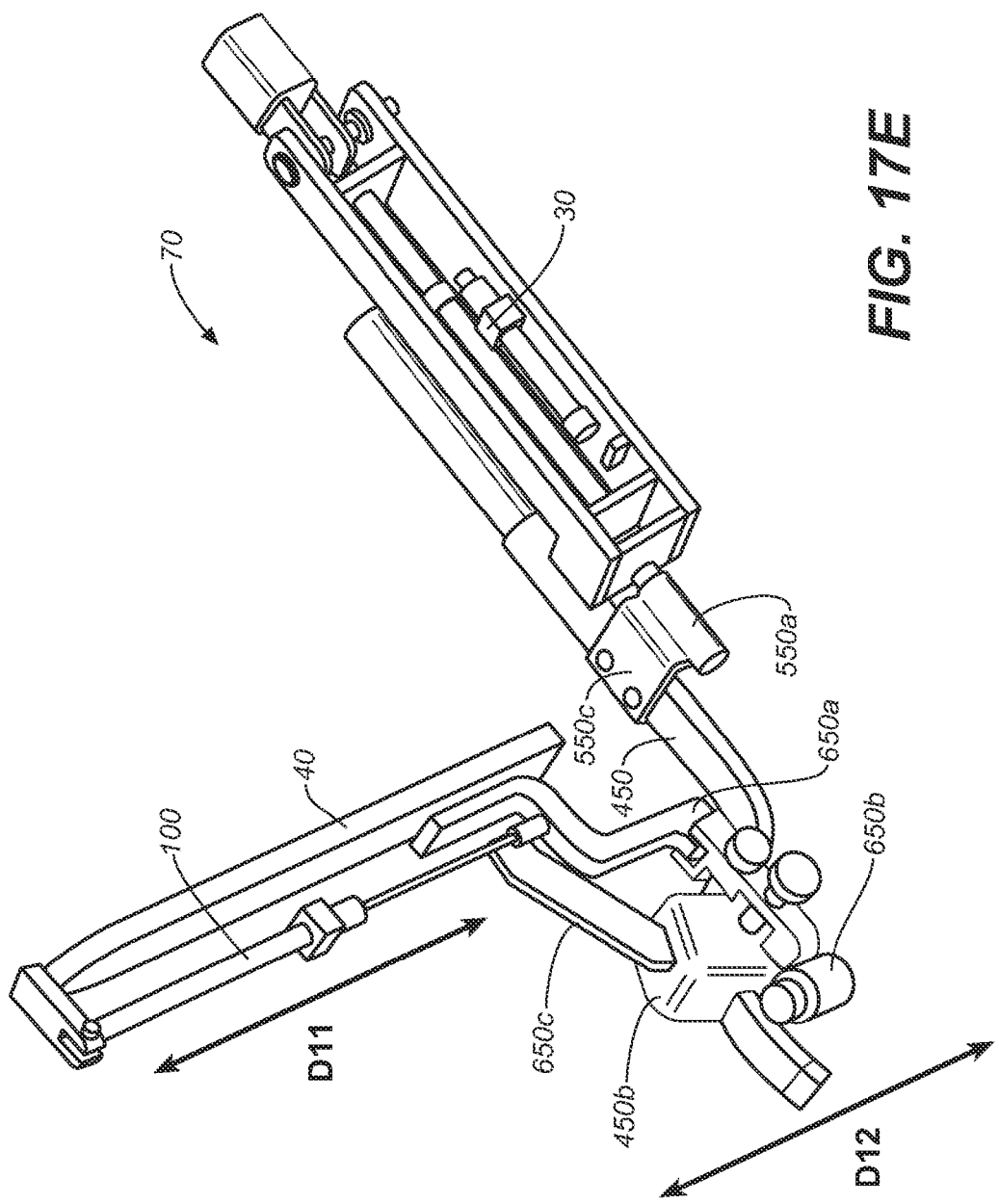

FIG. 17A-17E highlight a third example degree of freedom of the macro controls associated with an extension/retraction of the part of the slave portion 70. FIGS. 17A-17C show how the motion may be actuated in the macro controls 50b and FIGS. 17D and 17E show an example resultant motion in the slave portion 70.

As shown in FIGS. 17A-17E, the user may actuate an extension or retraction of the slave portion 70 by translating the macro controls 50b along direction D10. As shown in FIGS. 17A-17C, the macro controls 50b can include two sub-sub-portions 600a and 600b that may move relative to each other, and relative to static portion 300b, as shown in FIG. 17A. FIG. 17C shows an example gear setup of transmission assembly 605 that may be used to translate the macro controls 50b along the direction D10 to actuate control cylinder 100.

For example, translating the macro control sub-portions 600a and 600b as shown in FIGS. 17A and 17B along direction D10 may cause gears in the gear setup of transmission assembly 605 to turn. In the example variation shown in FIGS. 17A-17C, static portion 300b is held stationary with respect to anchor 610, while both macro control sub-portions and 600b are allowed to move with respect to anchor 610. However, it is to be understood that other configurations are also possible. Anchor 610 may be fixed to another portion of the device, to a stand or to another immobile or mobile object. On the other hand, macro control sub-portion 600a may be fixed to the micro controls 50a, as shown in FIG. 17C. Generally, the control cylinder 100 may have one end fixed to macro control portion 300b and the other fixed to macro control sub-portion 600a such that relative motion of these two components causes either compression or expansion of the control cylinder (e.g., as shown in FIGS. 5A and 5B). When the micro controls 50a are moved along direction D10 (FIG. 17C), the macro control sub-portion 600a may be moved along the same direction causing a relative translation of sub-portion 600a with respect to macro control sub-portion 600b. This, in turn, may compress or open, the control cylinder 100 thereby expelling or drawing in hydraulic fluid to the control portion and having the opposite effect on the corresponding control cylinder in fluid communication in the slave portion 70.

The control cylinder 100, portion 300b, sub-portion 600a, sub-portion 600b and the gear setup of transmission assembly 605 may be configured such that any suitable combination of motions is possible. For example, moving sub-portions 600a and 600b away from one another along direction D10 may ultimately cause fluid to be pumped to the slave portion 70 of the device. In this case, moving sub-portions 600a and 600b in an opposite direction, e.g., towards one another along direction D10, may ultimately cause fluid to be pumped to the control portion of the device. Alternatively, moving sub-portions 600a and 600b toward one another along direction D10 may ultimately cause hydraulic fluid to be pumped to the slave portion 70 of the device. In this case, moving sub-portions 600a and 600b in an opposite sense, e.g., away from one another along direction D8, may ultimately cause hydraulic fluid to be pumped to the control portion of the device.

FIGS. 17D and 17E show how the motion of portion 300b, sub-portion 600a, sub-portion 600b and the gear setup of transmission assembly 605 described in FIGS. 17A-C may be translated into motion of the slave portion 70 of the device. In the example setup shown in FIG. 17D there is one control cylinder 100 connected to the Extension/Retraction actuator portion 40. Fluid is either pumped in or out of the control cylinder 100 in FIGS. 17D and 17E on the slave portion 70 of the device according to motion of portion 300b, sub-portion 600a, sub-portion 600b and the gear setup of transmission assembly 605 discussed above with reference to FIGS. 17A-17C.

In FIG. 17D, the control cylinder 100 in the Extension/Retraction actuator portion 40 receives or expels fluid associated with the third example degree of freedom. FIG. 17E shows the setup in FIG. 17D without the instrument 4 or the instrument holder 4a. As shown in FIG. 17D, the instrument 4 and the instrument holder 4a may be coupled to control cylinder 100 in the Extension/Retraction actuator portion 40 via coupling 650a, such as a linkage. Coupling 650a may connect the control cylinder 100 in the Extension/Retraction actuator portion 40 and the instrument holder 4a in a manner that allows motion in the control cylinder 100 in the Extension/Retraction actuator portion 40 to be translated to the instrument 4 because the instrument 4 is coupled to the instrument holder 4a.

For example, in one embodiment, instrument holder 4a may include coupling 650a fixedly connected to instrument 4 at a first position, and a coupling 650b movably connected to instrument 4 at a second position. Coupling 650b may be fixed to a base 40a of Extension/Retraction actuator portion 40 via a linkage 650c and coupling 450a, such as a wheeled carriage. As such, based on actuation of Extension/Retraction actuator portion 40, coupling 650a translates such actuation to extend or retract instrument 4 relative to coupling 650b. Thus, the connections between Extension/Retraction actuator portion 40 and instrument 4 may be configured to allow extension/retraction of instrument 4 at a fixed position controlled by the position of coupling 650b.

For example, instrument holder 4a and/or the couplings 650a, 650b, and 650c may have any suitable form for connecting the instrument 4 to the control cylinder 100 in the Extension/Retraction actuator portion 40 such that, for example, moving the control cylinder 100 in the direction D11 moves the instrument 4 in direction D12, which may be the same direction as D11. In this embodiment, direction D12 corresponds to a longitudinal axis of instrument 4, and such movement is referred to as an extension or retraction of instrument 4, e.g., relative to an operational environment O (see FIG. 1A). Thus, in one embodiment, the control cylinder 100 in the Extension/Retraction actuator portion 40 may move along the direction D11 shown in FIGS. 17D and 17E causing the instrument 4 to move along direction D12, as shown in FIGS. 17D-17E. This may allow the instrument 4 and the user U to operate on any portion of the operational environment O that may be accessed with such motion.

Micro Controls and Micro Motions

Overview

In this section, the micro controls and associated micro motions will be discussed in brief. The details of micro controls and associated micro motions will be discussed more thoroughly with respect to their actuating mechanisms in the section that follows. Although the control cylinders of the micro controls are numbered differently than the control cylinders 100 associated with the macro controls, it is to be understood that aspects of all control cylinders discussed herein are, in principle, interchangeable. Therefore, each feature and related mechanism discussed in the context of control cylinders 100 may apply equally well to the control cylinders of the micro controls and the instrument and/or tool discussed below. Similarly, each feature and related mechanism discussed in the context of the control cylinders of the micro controls and the tool discussed below may apply equally well to the control cylinders 100. Similarly, any of the hydraulic components discussed herein are, in principle, interchangeable. All such changes, substitutions and modifications are to be considered within the scope embodiments of the present invention.

Figure 18B:
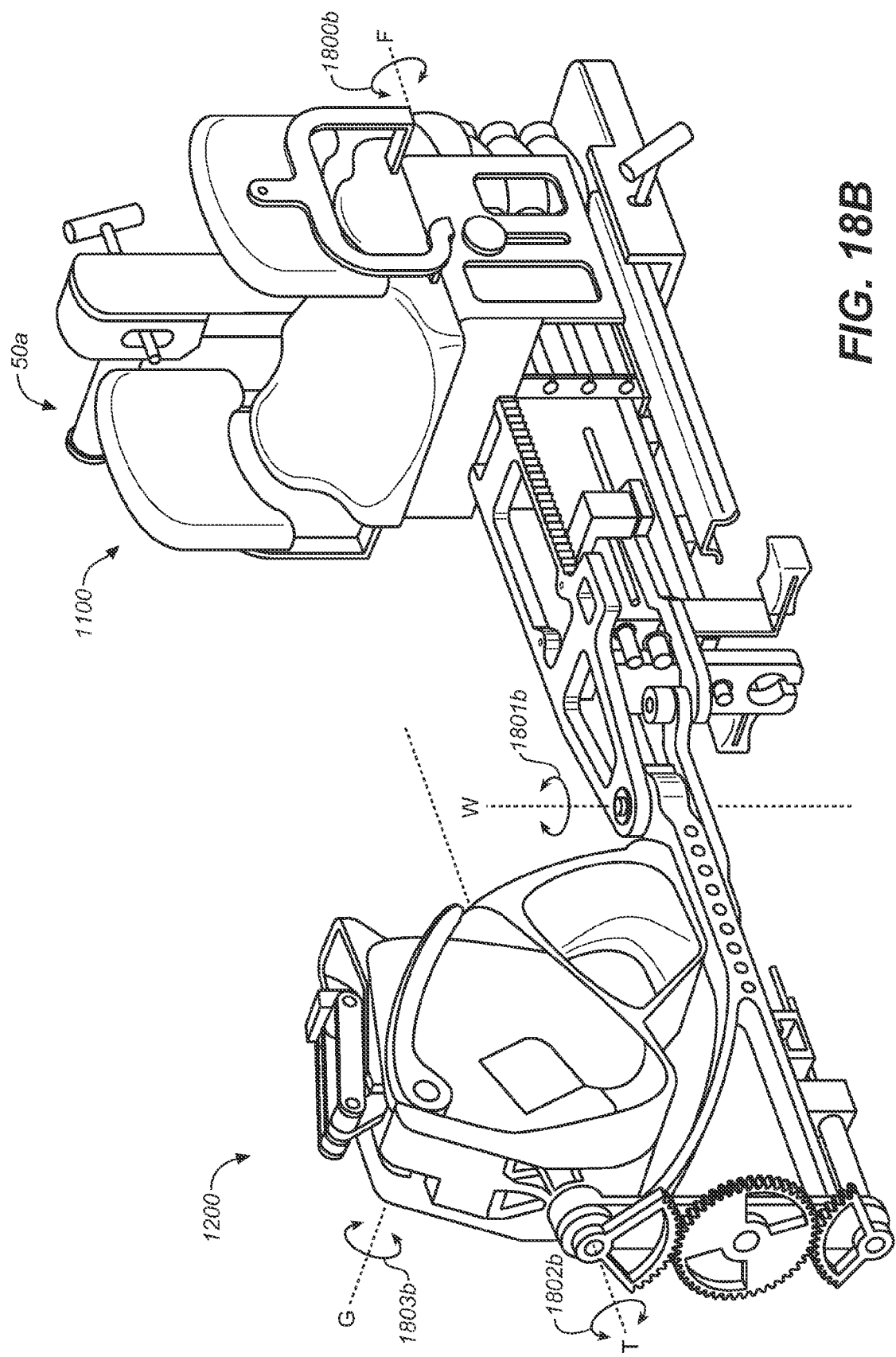
FIG. 18B is a perspective side view of an example micro control to illustrate various articulated motions, in accordance with various embodiments of the present invention.

FIG. 18A shows an overview of four example micro degrees of freedom in an instrument 4 and/or tool 7 which may be coupled with the slave portion 70 of the device in accordance with embodiments of the present invention. FIG. 18B shows an overview of how the four example micro degrees of freedom shown in FIG. 18A may be actuated in the control portion. The four example degrees of freedom will be discussed in more detail below. Note that FIG. 18A shows several example slave control cylinders (1410', 1420', 1430' and 1440') that may be used with the example degrees of freedom discussed herein as well as with additional example degrees of freedom. It should be noted that, while the example degrees of freedom are useful for certain applications, they are not meant to be exhaustive. Other degrees of freedom are within the scope of embodiments of the present invention. Indeed, it is possible to modify the existing apparatus as described to encompass either additional or fewer degrees of freedom, as needed. Additionally, although slave control cylinders are illustrated as being located within instrument 4, one or more of these slave control cylinders can be located external to instrument 4 and then coupled to internal portions of instrument 4 such as via a pushrod, screw, shaft, or the like. Further, mappings that are described between control cylinders in control portion 50 and cylinders within or coupled with instrument 4/tool 7 are provided by way of example, and may be altered from what is shown. Likewise, mappings that are described herein between control cylinders in control portion 50 and cylinders in slave portion 70 are provided by way of example, and may be altered from what is shown. Moreover, in some embodiments, control signals generate by macro control portion 50B may be mapped to control micro motions of instrument 7/tool 4. In a similar fashion, in some embodiments, control signals generated by micro control portion 50A may be mapped to control micro motions of slave portion 7. All such modifications should be considered within the scope of embodiments of the present invention.

In FIG. 18A, one of the example micro degrees of freedom shown is the forearm rotation 1800a of the instrument 4 and related components. Forearm rotation 1800a may allow instrument 4 to rotate about a primary axis 1901 of the instrument 4. This particular degree of freedom is useful for, among other things, positioning the instrument 4 about a particular area of interest in an operational environment O. For example, the forearm rotation 1800a degree of freedom can be used to position a tool 7, such as scalpel, on the end of the instrument 4 in a position appropriate for the making of an incision. Additionally, for example, the forearm rotation 1800a degree of freedom can be used to sweep a cutting motion with the scalpel on the end of the instrument 4. In another example, the forearm rotation 1800a degree of freedom can be used to position a tool 7, such as tweezers, on the end of the instrument 4 in a position appropriate for grasping a particular object (e.g., an organ or tissue). FIG. 18B shows how the forearm rotation 1800a degree of freedom may be actuated, in particular by a rotating motion 1800b of the user's forearm in conjunction with the micro controls 50a about forearm rotate axis F.

Also in FIG. 18A, another one of the example micro degrees of freedom shown is the wrist bend 1801a of the instrument 4 and related components. Wrist bend 1801a may allow instrument 4 to bend with respect to the primary axis of instrument 4. This particular degree of freedom is useful for, among other things, positioning a portion of the instrument 4 and/or a tool 7 about a particular area of interest in an operational environment O. For example, the wrist bend 1801a degree of freedom can be used to position a scalpel on the end of the instrument 4 in a position appropriate for the making of an incision. For instance, the wrist bend 1801a degree of freedom can be used to sweep a cutting motion with scalpel on the end of the instrument 4. In another example, the wrist bend 1801a degree of freedom can be used to position tweezers on the end of the instrument 4 in a position appropriate for grasping a particular object (e.g., an organ or tissue). FIG. 18B shows how the wrist bend 1801a degree of freedom may be actuated, in particular by a bending motion of the user's wrist in conjunction with the micro controls 50a to rotate 1801b a portion of micro controls 50a about wrist bend axis W.

Further, in FIG. 18A, two additional example micro degrees of freedom shown are tip rotation 1802a and tip grasp 1803a of the instrument 4 and related components. Tip rotation 1802a may allow instrument 4 and/or tool 7 to rotate about primary axis 1901, or to rotate about a secondary axis 1902 formed after bending a portion of instrument 4 relative to primary axis 1901. Tip grasp 1803a may allow instrument 4 and/or tool 7 to bend with respect to the primary axis 1901 of the instrument 4, or to bend about a secondary axis 1902 formed after bending a portion of instrument 4 relative to primary axis 1901. Further, for example, tip grasp 1803a may allow a relative bending or pivoting of two corresponding instrument or tool portions, e.g., pincher arms, to grasp or release an item. These particular degrees of freedom are useful for, among other things, positioning the instrument 4 and/or tool 7 about a particular area of interest in an operational environment O. For example, the tip rotation 1802a and tip grasp 1803a degrees of freedom can be used to position a scalpel on the end of the instrument 4 in a position appropriate for the making of an incision. Additionally, for example, the tip rotation 1802a and tip grasp 1803a degrees of freedom can be used to sweep a cutting motion with scalpel on the end of the instrument 4. In another example, the tip rotation 1802a and tip grasp 1803a degrees of freedom can be used to position tweezers on the end of the instrument 4 in a position appropriate for grasping or releasing a particular object (e.g., an organ or tissue). FIG. 18B shows how the tip grasp 1803a degree of freedom may be actuated by rotating 1803b about grasp axis G, in particular by gripping certain aspects of the micro controls 50a that will be described in more detail below. FIG. 18B shows how the tip rotation 1802a degree of freedom may be actuated, in particular by rotating 1802b certain aspects of the micro controls 50a, that will be described in more detail below, about tip rotate axis T.

Micro Controls

Figure 19:
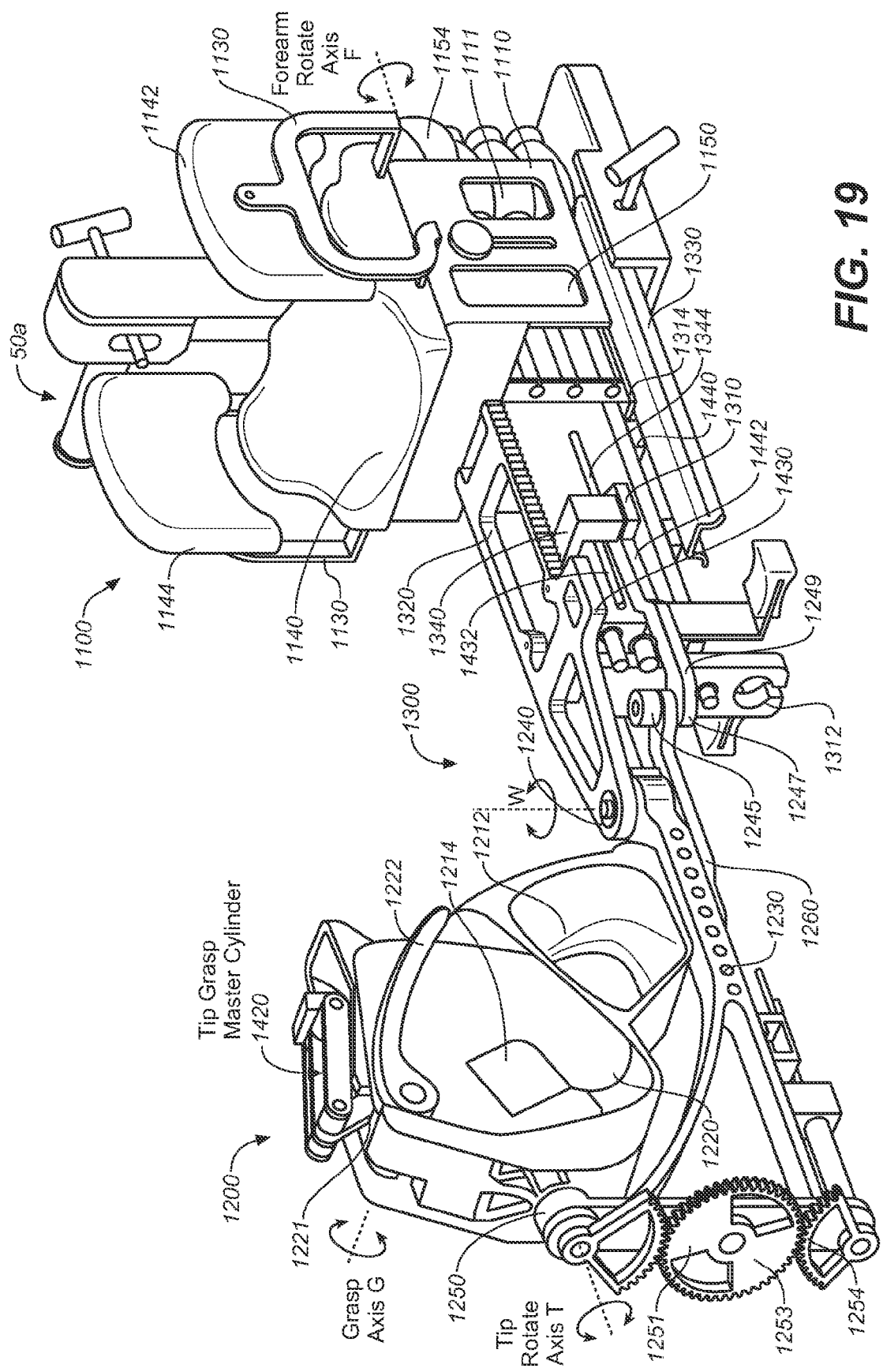
FIG. 19 is a perspective view of an example micro controls for use with a hand articulated control system, in accordance with an embodiment of the present invention.

FIG. 19 shows example micro controls 50a in accordance with embodiments of the present invention. The micro controls 50a may include an arm holder assembly 1100 and a grasper handle assembly 1200 connected by a central frame assembly 1300. The arm holder assembly 1100, grasper handle assembly 1200 and central frame assembly 1300 may be configured to allow various inputs 3 (FIG. 1A), such as linear and/or rotational movements, to generate corresponding outputs 11 (FIG. 1A) that result in the above-described micro motions.

In one variation of an embodiment of the present invention, the micro controls 50a control four degrees of freedom, including a forearm rotate 1800a, a wrist bend 1801a, a tip rotation 1802a, and a tip grasp 1803a (see FIG. 18A). The user places an arm into the arm holder assembly 1100 and inserting index and middle fingers through finger loops 1212 and 1214 provided on a grasper handle 1210, which is supported at the distal end of the micro controls 50a. A user may generally actuate the degrees of freedom of the system by moving one or more aspects of the micro controls 50a, including the arm holder assembly 1100 and components of the grasper handle assembly 1200. As shown in FIG. 18B, the user may rotate 1800b the entire micro controls 50a to actuate the forearm rotation 1800a degree of freedom. As also shown in FIG. 18B, the user may rotate 1801b an aspect of the grasper handle assembly 1200 to actuate the wrist bend 1801a degree of freedom and rotate 1802b another aspect of the grasper handle assembly 1200 to actuate the tip rotation 1802a degree of freedom. Further, FIG. 18B also shows that the user may trigger or squeeze other aspects of the grasper handle assembly 1200 in order to actuate the tip grasp 1803a degree of freedom by rotating a portion of micro controls 50a about tip grasp axis G. These motions will be discussed in more detail below.

The micro controls 50a are attached to a lower control assembly, which controls the other three degrees of freedom, namely the larger macro motions of extending the instrument 4 in and out of the patient and the two tilt axes, forward/backward and left/right (not shown).

Movements of the micro controls 50a are translated into hydraulic motion by controls that include one or more cylinders, such as a set of master cylinders, a tip rotate master cylinder 1410, a grasp axis master cylinder 1420, a wrist bend master cylinder 1430 and a forearm rotation master cylinder 1440. The master cylinders 1410, 1420, 1430 and 1440 are hydraulically connected to a set of slave control cylinders (1410', 1420', 1430', and 1440') to translate the forearm, wrist and finger motions of the user into mechanical controlling motions of a surgical instrument 4. The master cylinders 1410, 1420, 1430 and 1440 use various methods of translation, such as link arrangements and screw pistons, for example, to convert rotational and/or linear movement into a displacement of hydraulic fluid applied to the slave control cylinders. Moreover, the master cylinders 1410, 1420, 1430 and 1440 may be provided with a clutch mechanism (not shown) to disengage the translation of motion when such motion reaches a threshold, e.g., to prevent aggressive or overreaching movements of the micro controls 50a. In particular, the clutch mechanism automatically disengages function of the master cylinders 1410, 1420, 1430 and 1440 in the event an excessive pressure is generated, preventing damage to the hydraulics of the device 1000 and possible detrimental impact on the operational environment a (FIG. 1B-C), such as on a patient.

First Example MICRO Degree of Freedom: Forearm Rotation

In an embodiment, arm holder assembly 1100 is connected to central frame assembly 1300 to provide relative rotation 1800b about a forearm rotation axis F. For example, the central frame assembly 1300 may include a primary support plate 1310, a forward center axle support 1312, a rear center axle support 1314, an upper rack beam 1320, and a lower center beam 1330. A center axle 1340 is rotatably supported by the forward and rear center axle supports, 1312 and 1314, respectively, which are both fixed on one side to the primary support plate 1310. Forward and rear hinge brackets, 1342 and 1344, respectively, are fixed to a lower surface of the upper rack beam 1320. The center axle 1340 extends through the hinge brackets 1342, 1344, which are connected to the center axle 1340 so that the upper rack beam 1320 rotates 1800b the center axle 1340 about a forearm axis of rotation F when the forearm of a user (not shown) rotates.

As shown in FIG. 19, the forearm rotation master cylinder 1440 is situated substantially below the arm holder assembly 1100 and supported on the lower center beam by a bracket 1442. Rotation 1800b of the forearm is translated into rotation of the center axle 1340 about the forearm rotation axis F which, in turn, may drive a pendulum gear 1445 fit to the distal end of the center axle 1340 extending forward of the forward center axle support 1312. The pendulum gear 1445 may drive a turn gear 1447 to drive a forearm screw piston 1249, for example, into or out of the forearm rotation master cylinder 1440, depending on the direction of rotation indicated by the forearm. The screw piston 1249 may be provided with a sealed nut (not shown) on an end internal to the Forearm rotation master cylinder 1440, for example, the linear movement of which is caused by rotation of the screw piston 1249. The rotational motion of the forearm is thus translated by the screw piston 1249 into a linear piston motion which may compress or decompress a hydraulic fluid provided in the Forearm rotation master cylinder 1440. Pressure (or release thereof) is transferred from the forearm rotation master cylinder 1440 to a corresponding slave control cylinder 1440' (see FIGS. 5A, 5B, and 18A) via displacement of hydraulic fluid to drive a rotation of the surgical instrument 4 (see FIG. 18A) through a hydraulic line (not shown), for example. The hydraulic line may comprise flexible tubing. Although flexible, the tubing may be manufactured from a hard plastic, or with expansion resisting components such as metal fibers, to avoid extensive expansion of the tubing due to pressure and extended use. Furthermore, in some embodiments, the tubing may be supported with a metal-reinforced sleeve, for example, to prevent rupture of the thin wall while maintaining a degree of flexibility for increased modularity and mobility of the device 1000.

The hydraulic fluid is preferably sterilized distilled water, however, a saline solution, a perfluorinated hydrocarbon liquid, air or any other physiologically compatible fluid could also be used. A "physiologically compatible fluid" is a fluid that once exposed to tissues and organs, does not exacerbate a reaction, such as a rash or immune response, in the patient, and does not adversely interfere with the normal physiological function of the tissues or organs to which it is exposed. In addition, a physiologically compatible fluid can remain in a patient's body or in contact with a tissue or an organ without the need to remove the fluid.

Although movements of the micro controls 50a are described herein as being hydraulically actuated to control associated movements of a slave apparatus, the movements may generate electrical signals that are sent through wires to control the slave portion(s) 70 of the device 1000. The electrical signal, for example, may actuate a motor in the corresponding slave module to actuate the motion desired. In addition, motors may be used to enhance a hydraulically actuated movement, thus assisting a user in achieving the designated motion with less user applied force, which may be of benefit to the increased endurance of a user, for example, during long procedures.

Second Example MICRO Degree of Freedom: Wrist Bend

Figure 20:
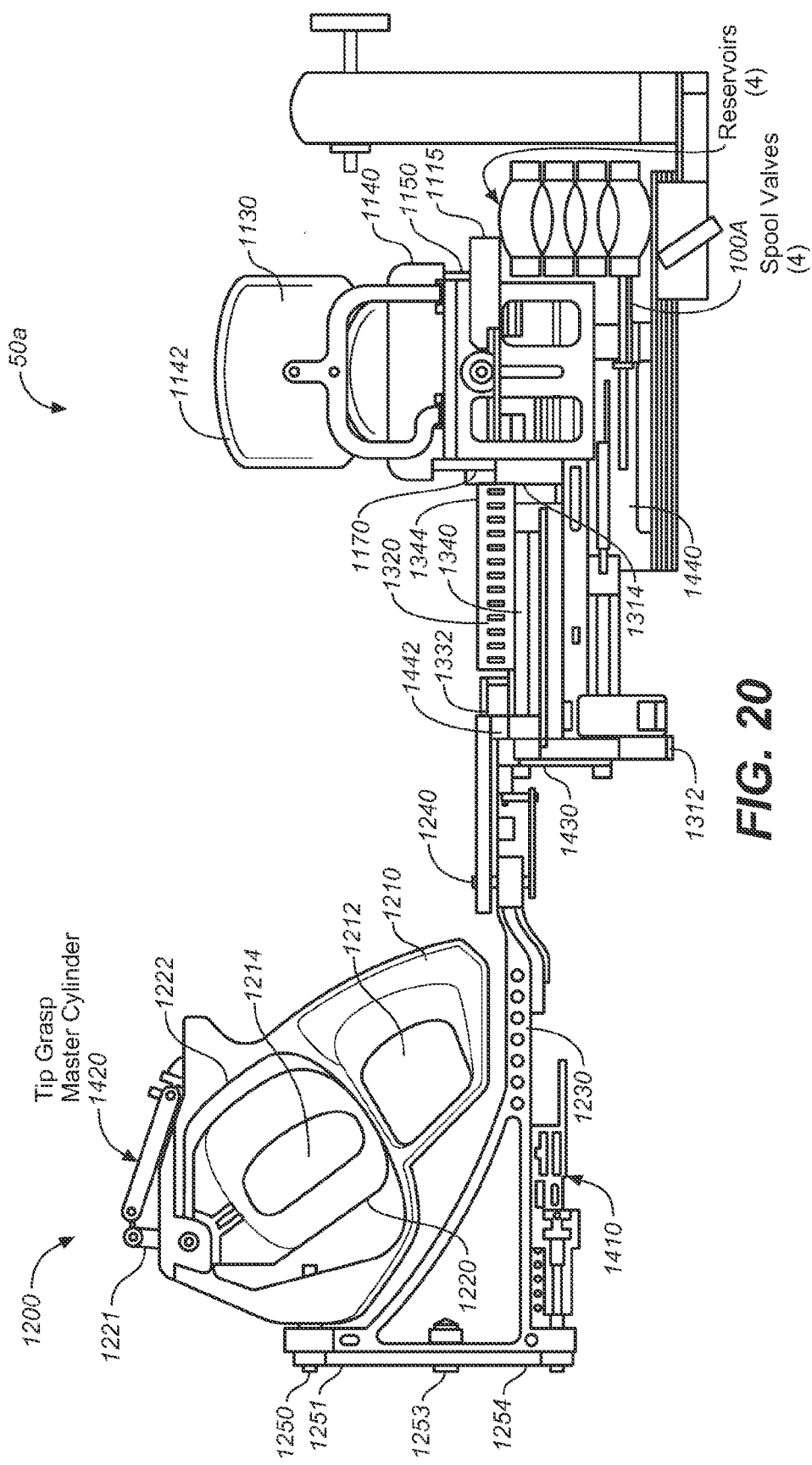
FIG. 20 is a side view of the example micro controls for use with a hand articulated control system, in accordance with an embodiment of the present invention.
Figure 21:
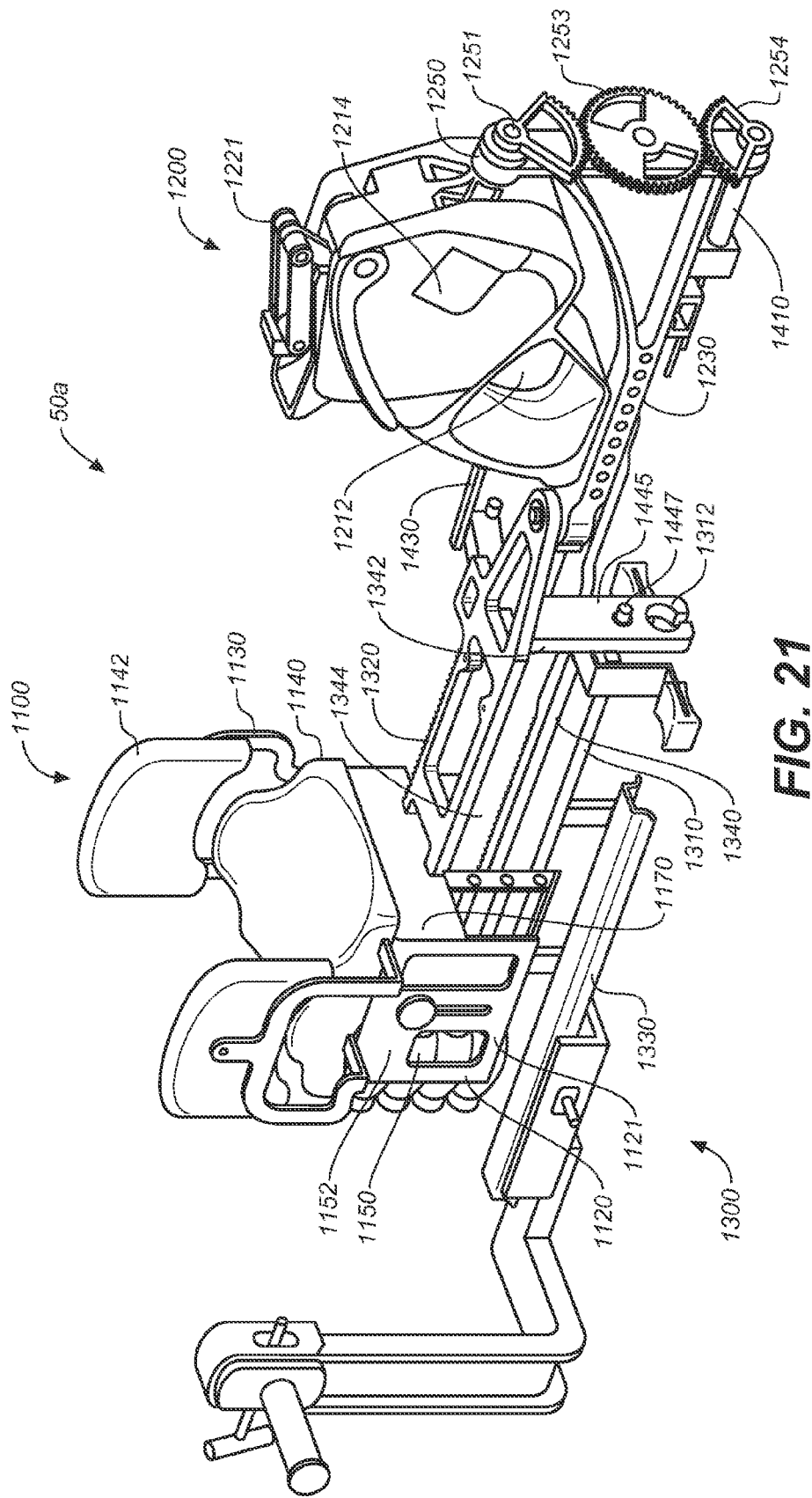
FIG. 21 is a side perspective view of the example micro controls for use with a hand articulated control system, in accordance with an embodiment of the present invention.
Figure 22:
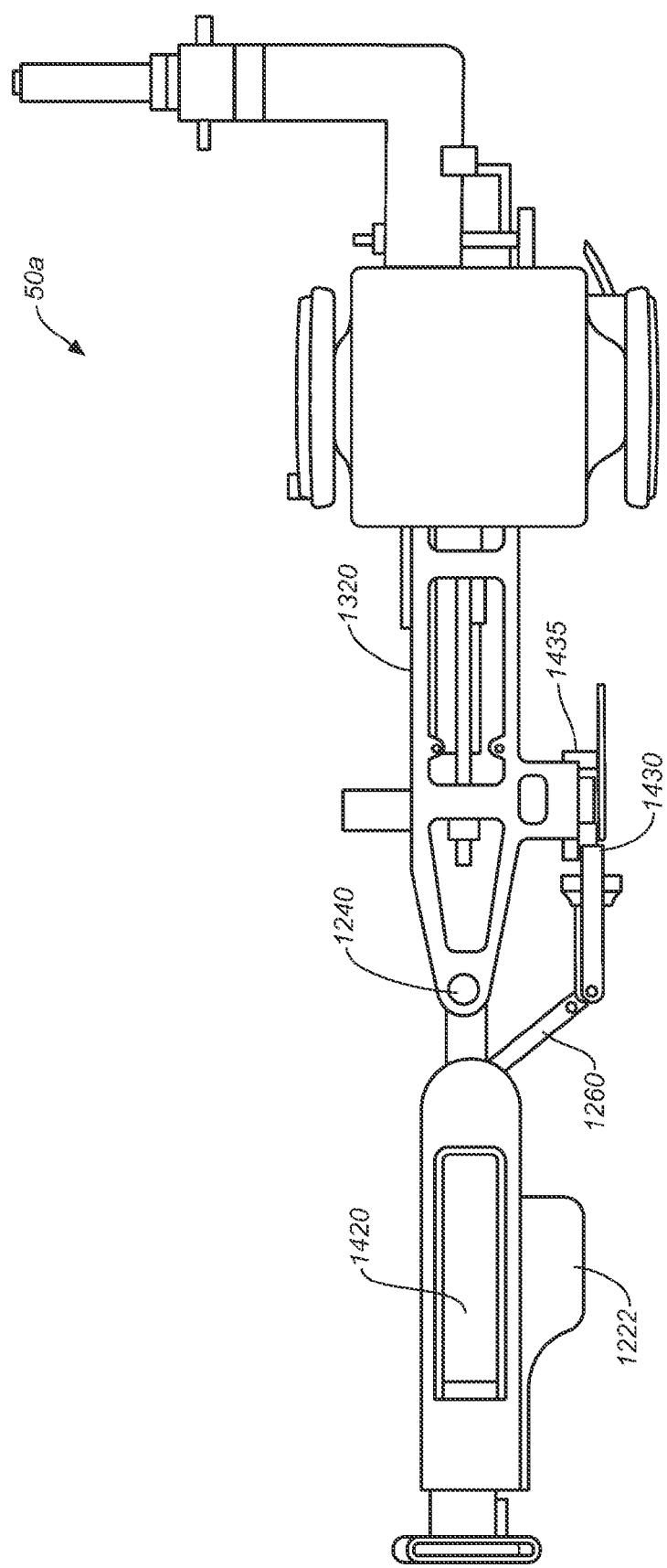
FIG. 22 shows is a top view of the example micro controls for use with a hand articulated control system, in accordance with an embodiment of the present invention.

In accordance with an embodiment of the present invention, the wrist bend 1801a motion of the surgical instrument 4 (see FIG. 18A) may be controlled by the wrist bend master cylinder 1430. As shown in FIGS. 19-21, the grasper handle assembly 1200 includes a grasper frame 1230. One end of the grasper frame 1230 is connected to the upper rack beam 1320 at a wrist bend pivot point 1240 and at the other end to the grasper handle 1210 at a tip rotation pivot point 1250. A wrist bend link member 1260 is provided between the grasper frame 1230 and the wrist bend master cylinder 1430. The user may actuate a wrist bend 1801a motion in the surgical instrument 4 (see FIG. 18A) by pivoting 1801b the grasper frame 1230 around a wrist bend axis W of the wrist bend pivot point 1240. The pivoting of the grasper frame 1230 may push or pull the wrist bend link member 1260, which, in turn, may linearly push or pull a piston in the wrist bend master cylinder 1430. The corresponding displacement of hydraulic fluid in the wrist bend master cylinder 1430 is transferred to a slave control cylinder 1430' for actuating the wrist bend 1801a motion in the surgical instrument 4. As shown in FIG. 22, the wrist bend master cylinder 1430 is secured to the upper rack beam 1320 by a bracket 1435.

Third and Fourth Example Micro Degrees of Freedom

Rotational and Grasp Control of Tip

Various embodiments of the present invention may provide rotational and grasp control of the tip of the instrument 4 (see FIG. 18A). As shown in FIGS. 19-21, the user may insert one or more fingers through each of finger loops 1212 and 1214 which are provided on grasper handle 1210. To actuate an articulation motion of instrument 4, such as tip grasp 1803a motion, the user may squeeze or push trigger 1220, causing the trigger to rotate 1803b about the tip grasp axis G in a counterclockwise or clockwise motion, toward or away from the user. Thus, trigger 1220 is capable of bi-directional user imitated movement. The trigger 1220 may be formed with an extension 1221 connected to the grasp axis master cylinder 1420, so that pivoting 1803b of trigger 1220 around grasp axis G may push or pull extension 1221, which in turn, may linearly push or pull a piston in the grasp axis master cylinder 1420. The corresponding displacement of hydraulic fluid in the grasp axis master cylinder 1420 forms a control signal that is transferred to a slave control cylinder 1420' for actuating a motion, such as a grasp motion (e.g., tip grasp 1803a motion as shown in FIG. 18A), in surgical instrument 4.

To assist the user in pushing the trigger 1220, trigger 1220 may be provided with a flange 1222 that extends away from the main body of trigger 1220. The flange 1222 provides a mechanism by which the user may, for example use a thumb to apply pressure against flange 1222 to force trigger 1220 to rotate away from the user, creating the reverse motion from the motion that is created by squeezing trigger 1220 with one or more fingers that are engaging finger loop 1214. It is appreciated that finger loop 1214 is a portion of trigger 1220, and thus moves when trigger 1220 is moved in either of its two opposing directions of movement. Conversely finger loop 1212, which is also a part of grasper handle 1210, remains immobile in response to movement of trigger 1220 and finger loop 1214 through user motion inputs such as squeezing or pushing. As discussed above movement of trigger 1220 creates a control signal. In one embodiment, squeezing (pulling) trigger 1220 may cause tip graspers 1730 on surgical instrument 4 to close in vice-like fashion (see FIG. 18A). Conversely, pushing trigger 1220 by applying pressure to flange 1222 may cause tip graspers 1730 to open. Accordingly, a user may control the speed and degree of the tip grasping motion by applying more or less force to trigger 1220 and setting the relative position of trigger 1220 in relation to being either fully open or fully closed.

As shown in FIG. 19, the grasper handle 1210 may be free to rotate 1802b around the tip rotate axis T to provide rotational control 1802a of the tip of the instrument 4 (see FIG. 18A). The grasper handle 1210 may be pivotally mounted onto the grasper frame at the tip rotate pivot point 1250. A sector gear 1251 may be coupled to the grasper handle 1210 so that rotation 1802b of the grasper handle 1210 about the tip rotate pivot point 1250 causes the sector gear 1251 to rotate counterclockwise or clockwise. The sector gear 1251 may work in tandem with a multiplier gear 1253 and a second sector gear 1254 attached to the tip rotate master cylinder 1410 to translate the rotational movement of the grasper handle 1210 into linear motion of a screw piston, for example, in the tip rotate master cylinder 1410. As shown in FIG. 20, the tip rotate master cylinder 1410 may mount onto the grasper frame 1230 and the grasper frame 1230 may provide rotatable support to the gears 1253 and 1254. Accordingly, the pivoting of the grasper handle 1210 about the tip rotation pivot point 1250 may linearly push or pull the screw piston, for example, in the tip rotate master cylinder 1410. The corresponding displacement of hydraulic fluid in the tip rotate master cylinder 1410 is transferred to a slave control cylinder 1410' for actuating the tip rotate motion 1802a in the instrument 4 (see FIG. 18A).

Support Structure and Adjustability of the Micro Controls

The arm holder assembly 1100 has a support structure that includes left and right mounting plates, 1110 and 1120, respectively, supporting an arm bracket 1130. A horizontal arm rest 1140, a vertical left arm support 1142 and a vertical right arm support 1144 are mounted to the arm bracket 1130 to effectively cradle and support the arm of the user during a procedure. The horizontal arm rest 1140 may be formed to be adjustable left or right by sliding along the arm bracket 1130.

The arm holder assembly 1100 may be adjusted both horizontally and vertically. The left and right mounting plates 1110, 1120 are provided with vertical slots 1111, 1121. A lateral support 1150, e.g., a bolt, may be provided that extends through the vertical slots 1111 and 1121 on the left and right mounting plates 1110, 1120 and may include a locking nut 1152 (see FIG. 21) and a handle clamp 1154: By releasing the handle clamp 1154, the arm holder assembly 1100 may be raised or lowered. By locking the handle clamp 1154, the arm holder assembly 1100 may be locked into a set position. As shown in FIGS. 19-21, the left and/or right mounting plates 1110, 1120 may be provided with a scale 1115 or similar markings to indicate the relative adjusted height of the arm holder assembly 1100. In this manner, the user may note the height indication for quick and easy vertical adjustment of the arm holder assembly 1100, each time using the device 1000. As shown in FIG. 21, the lateral support 1150 connects the arm holder assembly 1100 to the horizontal upper rack beam 1320 through a brace mechanism 1170. The brace mechanism 1170 engages and surrounds the upper rack beam 1320 while permitting linear movement of the brace mechanism 1170 along the upper rack beam 1320. By sliding the arm holder assembly 1100 longitudinally along the upper rack beam 1320, a horizontal distance between the arm holder assembly 1100 and the grasper handle 1210 may be adjusted. Similar markings may be provided on the upper rack beam 1320, for example, to allow quick and easy horizontal adjustment of the arm holder assembly 1100. The arm holder assembly 1100 may thus be adjusted both vertically and horizontally to provide a comfortable and customizable arrangement for supporting the user's arm during the length of a procedure.

Figure 23:
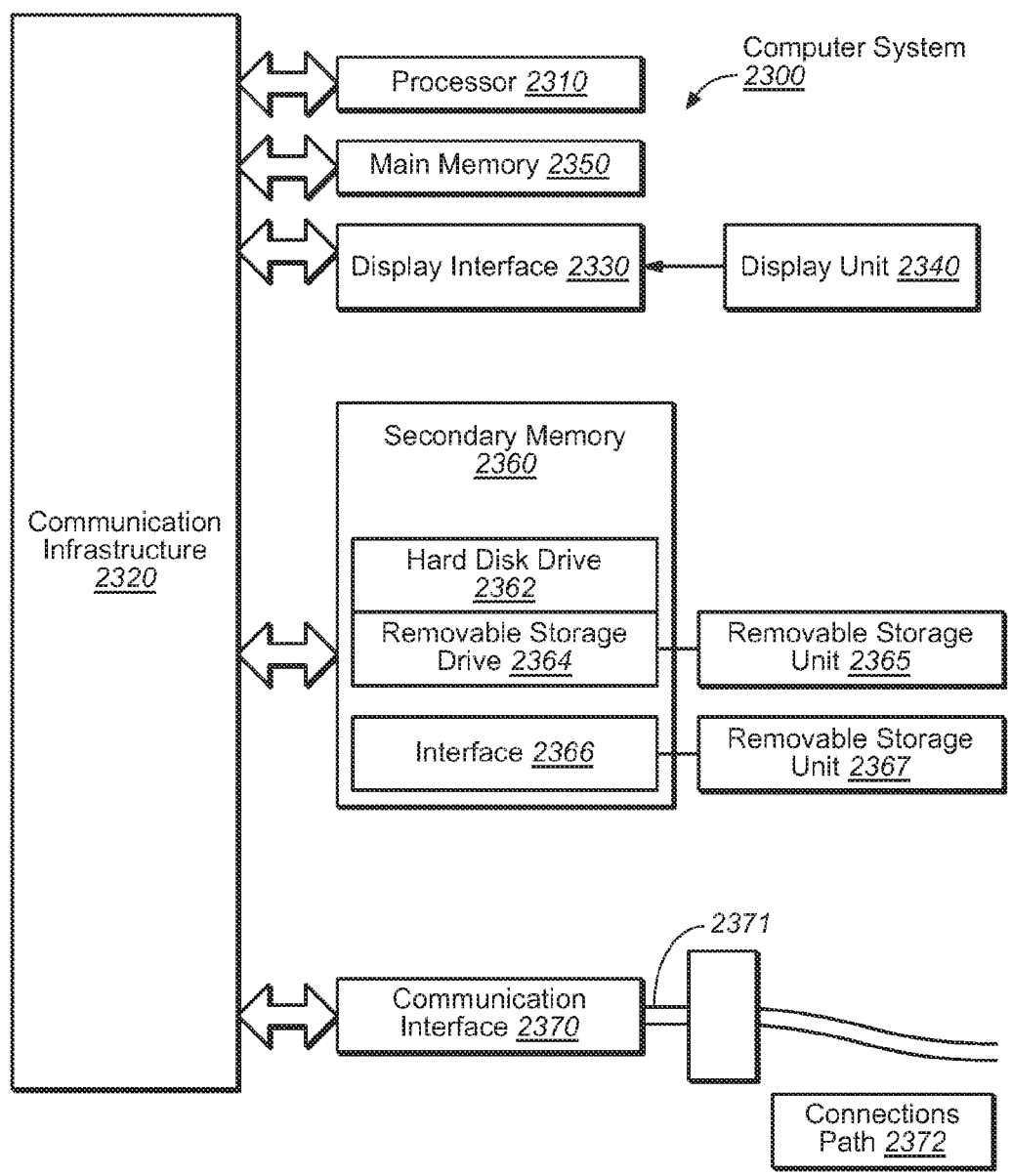
FIG. 23 shows an example computer system that may be used, in conjunction with various embodiments of the present invention.

Although embodiments of the invention have been shown primarily as being manually and/or hydraulically actuated, it is to be understood that one or more embodiments of the invention may alternatively or additionally be electrically actuated or actuated via computer interface. Embodiments of the present invention may be implemented using hardware, software or a combination thereof and may be implemented in one or more computer systems or other processing systems. In one variation, embodiments of the present invention are directed toward one or more computer systems capable of carrying out the functionality described herein. An example of such a computer system 2300 is shown in FIG. 23. For example, computer system 2300 may receive input 3 (FIG. 1A) and generate output 11 using electrical control signals to control motors to perform the above-described movements.

Example Computer System

Computer system 2300 is an example computer system which may be utilized in conjunction with some embodiments of device 1. Computer system 2300 includes one or more processors, such as processor 2310. The processor 2310 is connected to a communication infrastructure 2320 (e.g., a communications bus, cross-over bar, or network). Various software embodiments are described in terms of this example computer system. After reading this description, it will become apparent to a person skilled in the relevant art(s) how to implement various aspects and embodiments of the present invention using other computer systems and/or architectures.

Computer system 2300 can include a display interface 2330 that forwards graphics, text, and other data from the communication infrastructure 2320 (or from a frame buffer not shown) for display on the display unit 2340. Computer system 2300 also includes a main memory 2350, preferably random access memory (RAM), and may also include a secondary memory 2360. The secondary memory 2360 may include, for example, a hard disk drive 2362 and/or a removable storage drive 2364, representing a floppy disk drive, a magnetic tape drive, an optical disk drive, etc. The removable storage drive 2364 reads from and/or writes to a removable storage unit 2365 in a well-known manner. Removable storage unit 2365, represents a floppy disk, magnetic tape, optical disk, etc., which is read by and written to removable storage drive 2364. As will be appreciated, the removable storage unit 2365 includes a computer usable storage medium having stored therein computer software (computer readable instructions for control of processor 2310) and/or data.

In alternative variations, secondary memory 2360 may include other similar devices for allowing computer programs or other instructions to be loaded into computer system 2300. Such devices may include, for example, a removable storage unit 2367 and an interface 2366. Examples of such may include a program cartridge and cartridge interface (such as that found in video game devices), a removable memory chip (such as an erasable programmable read only memory (EPROM), or programmable read only memory (PROM)) and associated socket, and other removable storage units 2367 and interfaces 2366, which allow software/instructions and data to be transferred from the removable storage unit 2367 to computer system 2300.

Computer system 2300 may also include a communications interface 2370. Communications interface 2370 allows software and data to be transferred between computer system 2300 and external devices. Examples of communications interface 2370 may include a modem, a network interface (such as an Ethernet card), a communications port, a Personal Computer Memory Card International Association (PCMCIA) slot and card, etc. Software/instructions and data transferred via communications interface 2370 may be in the form of signals 2371, which may be electronic, electromagnetic, optical or other signals capable of being received by communications interface 2370. These signals 2371 are provided to communications interface 2370 via a communications path (e.g., channel) 2372. This path 2372 carries signals 2371 and may be implemented using wire or cable, fiber optics, a telephone line, a cellular link, a radio frequency (RF) link and/or other communications channels. In this document, the terms "computer program medium" and "computer usable/readable medium" are used to refer generally to tangible storage media such as a removable storage drive 2364/removable storage unit 2365, and a hard disk installed in hard disk drive 2362. These computer program products provide software or other forms of instruction to processor 2310 and/or other portions of computer system 2300, which can instruct computer system 2300 to carry out certain actions and/or processes.

Computer programs (also referred to as computer control logic or instructions) are stored in main memory 2350 and/or secondary memory 2360. Computer programs may also be received via communications interface 2370. Such computer programs, when executed by processor 2310 and/or other portions of computer system 2300, enable the computer system 2300 to perform the features in accordance with various embodiments of the present invention, as discussed herein. In particular, the computer programs, when executed, enable the processor 2310 to perform the features of certain aspects of embodiments of the present invention. Accordingly, such computer programs represent controllers of the computer system 2300.

In one variation where aspects of the present invention are implemented using software, the software may be stored in a computer program product (e.g., a computer readable storage media/medium) and loaded into computer system 2300 using removable storage drive 2364 and/or hard drive 2362. The control logic/instructions, when executed by the processor 2310, cause the processor 2310 to perform the functions in accordance with one or more embodiments of the present invention, as described herein. In another variation, one or more aspects of the present invention are implemented primarily in hardware using, for example, hardware components, such as application specific integrated circuits (ASICs). For example, implementation of a hardware state machine so as to perform one or more of the functions described herein will be apparent to persons skilled in the relevant art(s).

Additional Embodiments

Figure 24A:
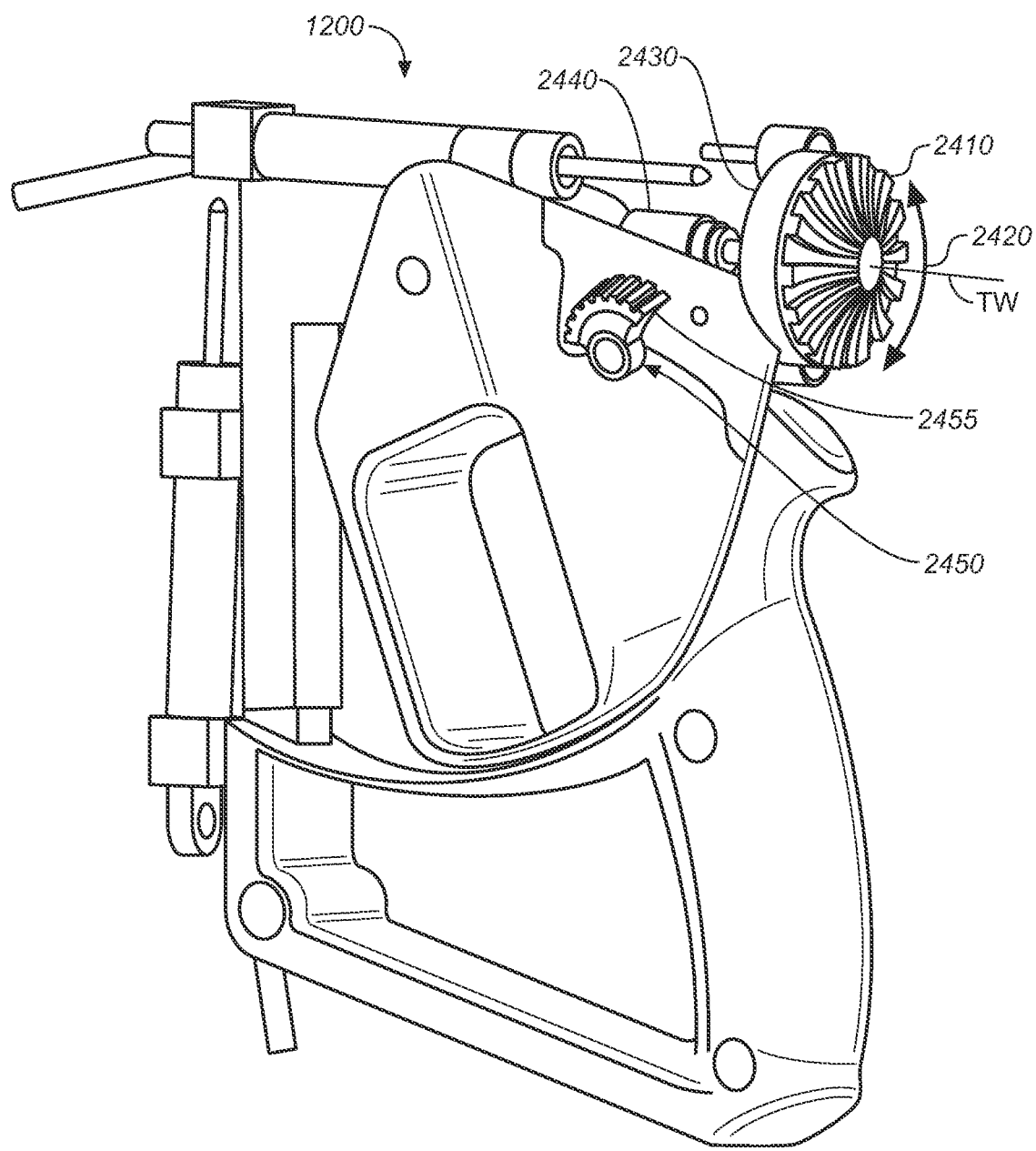
FIG. 24A is a side view of an example grasper handle which includes a thumbwheel and a surgical assistant ratchet for use with a hand articulated control system, in accordance with an embodiment of the present invention.

FIG. 24A is a side view of an example grasper handle 1200 which includes a thumbwheel and a surgical assistant ratchet for use with a hand articulated control system, in accordance with an embodiment of the present invention. FIG. 24A illustrates features such as thumbwheel 2410 and surgical assistant ratchet 2450, either or both of which may be included in some embodiments of micro control assembly 50A.

In an embodiment, thumbwheel 2410 is connected to grasper handle at a location which allows a user thumb to provide relative rotational motion in either of the two directions, illustrated by arrows 2420, about axis TW. Such rotational movement is spins a gear 2430 which interacts with other components such as a screw piston (not visible) to convert the rotational motion into linear motion which moves master cylinder 2440 in one of two linear directions depending on the direction of rotation direction of thumbwheel 2410. The linear movement of master cylinder 2440 displaces hydraulic fluid in response to rotation of thumbwheel 2410. This displacement of hydraulic fluid forms a control signal which in one embodiment may serve the same purpose as a control signal generated by rotation of a forearm. Similarly, in one embodiment, thumbwheel 2410 may be coupled with a gear such as a worm gear which is turned in response to rotation of thumbwheel 2410, and then translates rotation of thumbwheel 2410 into linear motion coupled to a shaft of master cylinder 2440. Thus, with reference to FIGS. 18A and 18B, instead of the user may rotating 1800*b* the entire micro controls 50*a* to actuate the forearm rotation 1800*a* degree of freedom, a user may rotate thumbwheel 2410 about axis TW to actuate the forearm rotation 1800 a degree of freedom of instrument 4. Moreover, in some embodiments, the control signals generated by rotation of thumbwheel 2410 may be mapped (e.g., hydraulically coupled to one or more slave hydraulic cylinders) to effect other movements of instrument 4 and or tool 7 besides forearm rotation 1800 a.

Referring again to FIG. 24A, surgical assistant "ratchet" 2450 may be actuated by the same user thumb which is used to actuate thumbwheel 2410. Lever 2455 of ratchet 2450 can be rotated by the user to mechanically lock one of the seven degrees of freedom of control portion 50. For example, in one embodiment ratchet 2450 can be utilized o lock an axis of movement associated with a grasp/dissect motion input of tool 7. In this manner, ratchet 2450 is used to lock the jaws of an attached instrument 4 down on a piece of tissue, needle, artery, vessel, etc. to allow the surgeon to loosen her grip on finger loop 1214 of trigger 1220. This reduces fatigue for the surgeon and facilitates a more controlled grip on the tissue or matter between the jaws than if the surgeon had to maintain constant pressure on finger loop 1214. In one embodiment, ratchet 2450 can be set into one of three positions which are selected by the surgeon via rotation of lever 2455. Although not depicted as such, in some embodiments, lever 2455 of ratchet 2450 may be incorporated into thumb flange 1222.

Figure 24B:
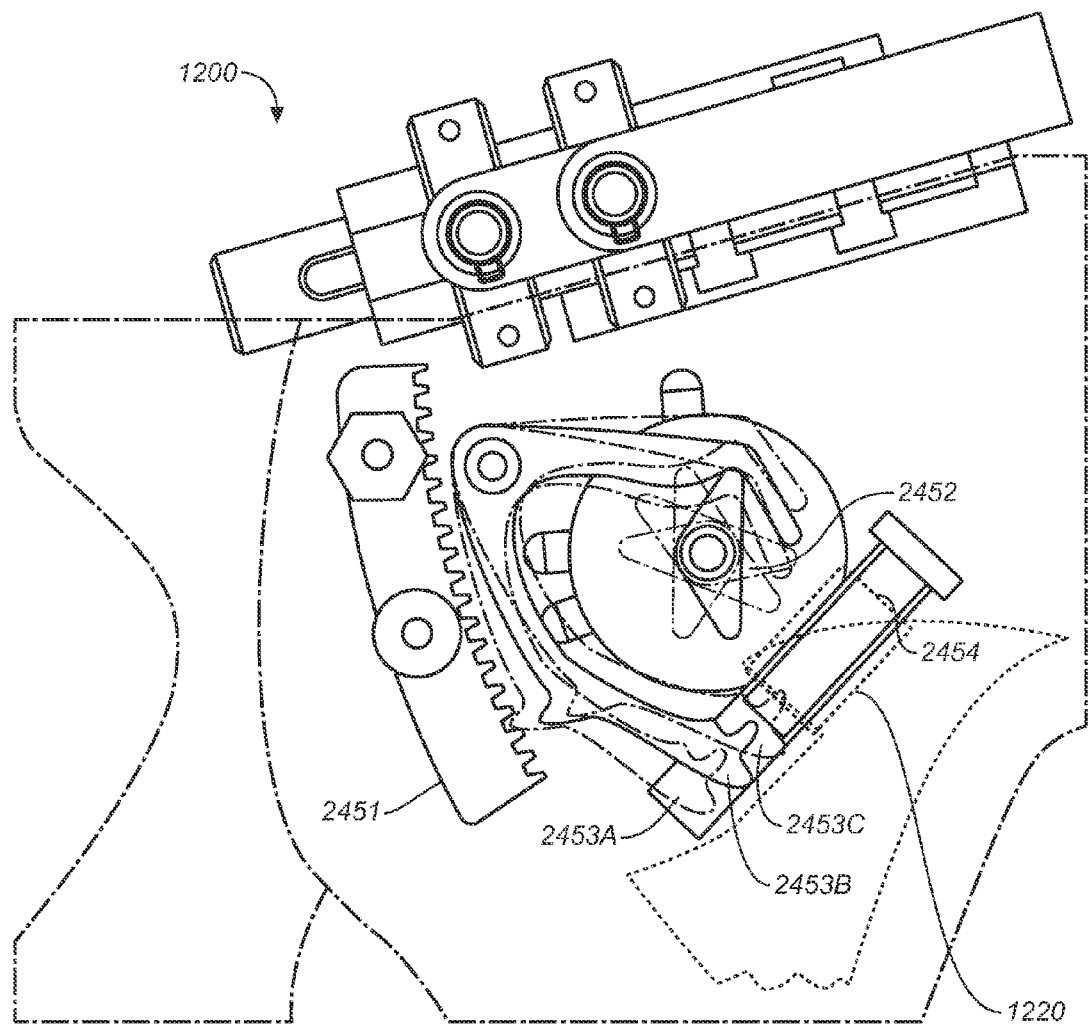
FIG. 24B illustrates an opposite side view from FIG. 24A, and depicts an inner plane of an example grasper handle, according to an embodiment.

FIG. 24B illustrates an opposite side view from FIG. 24A, and depicts an inner plane of grasper handle 1200, according to an embodiment. As can be seen lever 2455 is coupled with a single tooth pawl component 2453 (illustrated in three possible positions 2453A, 2453B, and 2453C) which is pivotally mounted with to trigger 1220. The tooth of pawl component 2453 catches on rack of teeth 2451 which is a stationary component mounted within grasper handle 1200. Cam 2452 is pivotally mounted to trigger 1220, which sets pawl 2453 into the correct orientation according to the position which the surgeon activates via lever 2550 (FIG. 24A). Spring 2454 is a compression spring which is fixed on a distal end from pawl 2453 and used to apply a force against pawl 2453 to maintain correct orientation as set by cam 2452. According to one embodiment, the three positions of cam 2450, which may be selected via rotation of lever 2455 are: 1) "released," which allows a user to temporarily disengage ratchet 2450, such as to open jaws of a tool 7; 2) "locked," which allows a user to lock a position of trigger 1220, such as to close jaws of a tool 7 and keep them closed without continually manually applying closing force; and 3) "defeated," which allows a user to disengage ratchet 2450 so that trigger 1220 can be opened and closed without engagement between rack of teeth 2451 and pawl 2453. By virtue of controlling a degree of freedom of movement of control portion 50 (and thus locking down or allowing a user input), ratchet 2450 is one implementation of a function control mechanism.

Example Methods of Use and Operation

Example Method of Manipulating an Articulating Surgical Instrument

Figure 25:
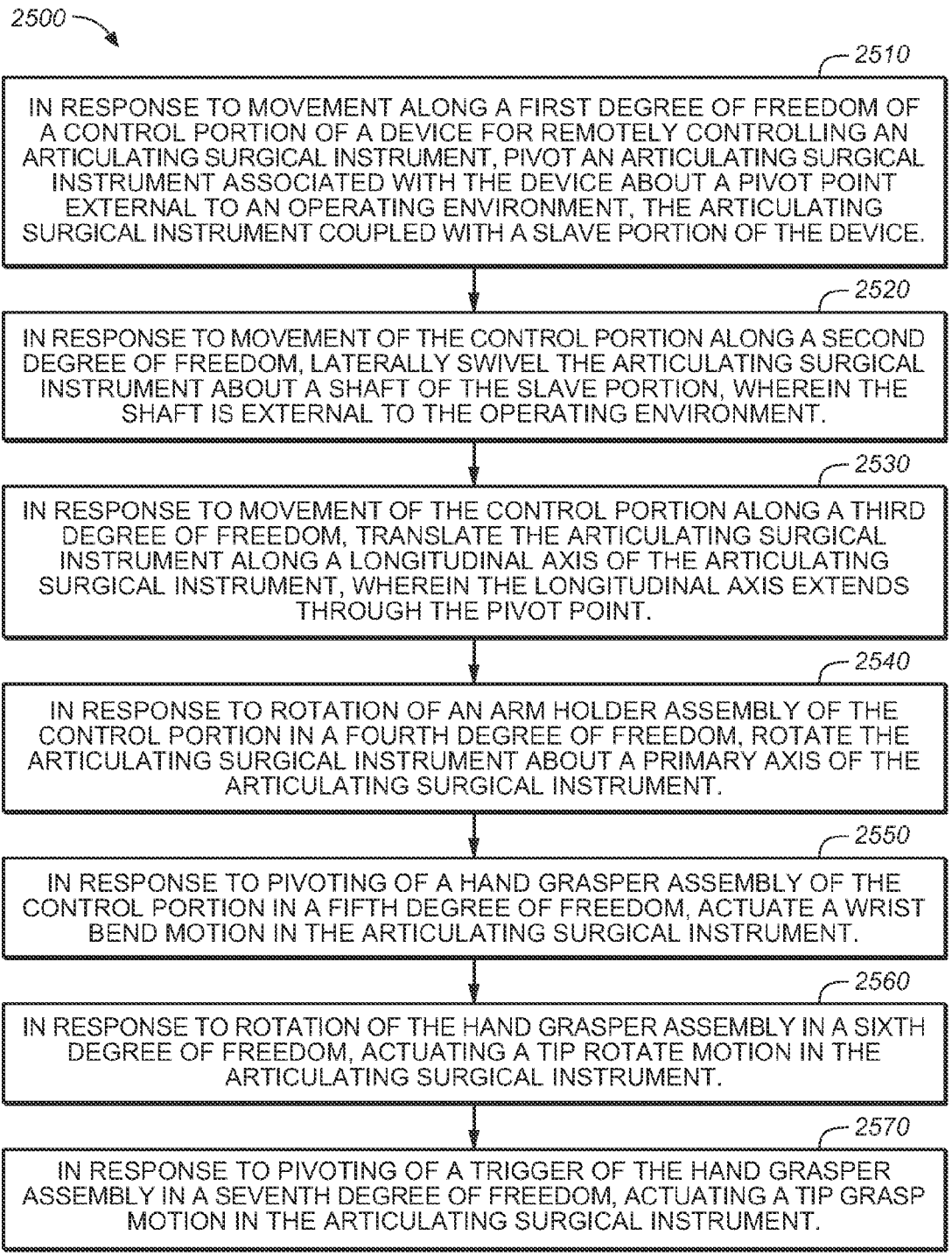
FIG. 25 illustrates a flow diagram of an example method of manipulating an articulating surgical instrument, in accordance with various embodiments of the present invention.

FIG. 25 is a flow diagram 2500 of an example method of manipulating an articulating surgical instrument, according to one embodiment. According to one embodiment, flow diagram 2500 illustrates an example method of manipulating articulating surgical instrument 4 in response to input via control portion 50. Although specific procedures are disclosed in flow diagram 2500, such procedures are example. That is, embodiments of the present invention are well suited to performing various other procedures or variations of the procedures recited in flow diagram 2500. It is appreciated that the procedures in flow diagram 2500 may be performed in an order different than presented, and that not all of the procedures described in flow diagram 2500 may be performed in every embodiment. In the description of the procedures of the method of flow diagram 2500, reference will be made to elements of FIGS. 1A-23, to include reference to control portion 50 (and components thereof), slave portion 70 (and components thereof), and/or instrument 4 (and components thereof).

At 2510 of flow diagram 2500, in one embodiment, an articulating surgical instrument is pivoted about a pivot point external to an operating environment. That is, in one embodiment the articulating surgical instrument is the instrument which the device remotely controls. The articulating surgical instrument is associated with or a portion of a "device" for remotely controlling an articulating surgical instrument. Device 1 is one example of such a device for remotely controlling an articulating surgical instrument, and instrument 4 is one example of an articulating surgical instrument that may be controlled by device 1. In one embodiment, as illustrated in FIGS. 1A, 1C, 7-12A, 14D, 15A, 16D, 16E, 17D, and 17E articulating surgical instrument 4 is coupled with a slave portion 70 of device 1.

"Remote control" and "remotely controlling" as used herein mean that a user can manipulate instrument 4 while being located remotely from the patient or operating room, by controlling instrument 4 remotely via manipulation of a control, such as control portion 50. The distance of the remoteness may vary from control from a few feet away to control from a separate room from instrument 4, or to control via tele-manipulation from much greater distances away from surgical instrument 4. When the remote location of control is fairly close, such as a few feet away or in the next room, there may be direct coupling, such as via hydraulic means, electrical means, mechanical means, and the like between control portion 50 and slave portion 70 and/or between control portion 50 and articulating surgical instrument 4. When the distance of remote control is great, such as miles, there may be telecommunications involved to communicate control signals generated at control portion 50 such that they are replicated at the location of slave portion 70 and instrument 4.

As has been described herein in conjunction with FIGS. 14A-14E and FIGS. 15A-15E, in one embodiment the pivoting about the pivot point occurs in response to a movement along a first degree of freedom of all or some portion of control portion 50 of device 1. The movement along a first degree of freedom of movement can be imparted to control portion 50 by a human shoulder, arm, and/or hand of a user of device 1. In one embodiment, the pivoting of articulating surgical instrument 4 about the pivot point occurs in response to a displacement of hydraulic fluid that is generated in control portion 50 by the movement along the first degree of freedom. As has been described previously, a user may input a first motion, by swiveling the entire micro control assembly 50a along arc D2 about pivot point 401. Macro control portion 50b then translates swiveling motion along arc D2 to a linear motion of one or more master control cylinders 100. Hydraulic lines may then transmit control signals, in the form of a displacement of hydraulic fluid, generated from the linear motion of control cylinder(s) 100 to one or more corresponding slave control cylinders 100 in slave portion 70 to effect motion of components of slave 70 that are coupled to the corresponding slave control cylinder(s) in slave portion 70. This causes instrument holder 4a and the instrument 4 (coupled thereto) to pivot about Pivot Point 2 (FIGS. 15A and 15B). In one embodiment, Pivot Point 2 is designed to be located external to an operating environment (that is, external to the body of a patient being operated upon), however in other embodiments, Pivot Point 2 may be within an operating environment. In other embodiments the translated movement may be in a different plane may be produced or motion may be produced depending on the orientation of components in a slave portion. In the interest of brevity and clarity, reference is made to FIGS. 14A-14E and 15A-15E for further description of the mechanics and process of pivoting instrument 4 about a pivot point in response to motion imparted by a user to control portion 50 of device 1.

At 2520 of flow diagram 2500, in one embodiment, the articulating surgical instrument may be laterally swiveled about a shaft of the slave portion 70. In one embodiment, such a shaft is external to the operating environment. This lateral swiveling occurs in response to movement of all or some portion of control portion 50 along a second degree of freedom. The movement along the second degree of freedom can be imparted to control portion 50 by the same human shoulder, arm, and/or hand used to impart motion along the first degree of freedom. The second degree of freedom is a different degree of freedom of movement of control portion 50 than the first degree of freedom.

As has been described herein in conjunction with FIGS. 16A-16F, in one embodiment, this swiveling motions comprises swiveling (see arc D8 of FIGS. 16D-16E) instrument 4 about shaft 550 (as is depicted and described in conjunction with FIGS. 16D-16F) in response to a motion being imparted to macro controls 50b, such as swiveling macro controls 50b along arc D6 (see FIG. 16A). In one embodiment, the laterally swiveling of articulating surgical instrument 4 about shaft 55.0a occurs in response to a displacement of hydraulic fluid generated in the control portion by the movement along the second degree of freedom. In one embodiment, macro control portion 50b translates swiveling motion along arc D6 to a linear motion of one or more master control cylinders 100. Hydraulic lines may then transmit control signals, in the form of a displacement of hydraulic fluid, generated from the linear motion of master control cylinder(s) 100 to one or more corresponding slave control cylinders 100 in slave portion 70 to effect motion of components of slave 70 (such as motion of shaft 550a) that are coupled to the corresponding slave control cylinder(s) in slave portion 70. This causes instrument 4, which is coupled to shaft 550a, to laterally swivel about arc D8 (FIGS. 16D-16E). It is appreciated that other motions, swiveling or otherwise, can be produced by orienting components in a different fashion within slave portion 70. In the interest of brevity and clarity, reference is made to FIGS. 16A-16E for further description of the mechanics and process of laterally swiveling instrument 4 along arc D8 in response to motion imparted by a user to control portion 50 of device 1.

At 2530 of flow diagram 2500, in one embodiment, the articulating surgical instrument is translated along a longitudinal axis of the articulating surgical instrument. In one embodiment, this longitudinal axis extends through the pivot point (e.g., Pivot Point 2) about which the articulating surgical instrument can be pivoted. This translating along the longitudinal axis occurs in response to movement of at least a portion of control portion 50 along a third degree of freedom. The movement along the third degree of freedom of movement of control portion 50 can be imparted to control portion 50 by the same human arm that is used to impart motion along the first and second degrees of freedom. The third degree of freedom is a different degree of freedom of movement of control portion 50 than the first and second degrees of freedom.

As has been described herein in conjunction with FIGS. 17A-17E, in one embodiment, this comprises extending and retracting actuator 40 of slave portion 70 along direction D11 (as is depicted and described in conjunction with FIGS. 17D-16E) in response to a motion being imparted to macro controls 50b, such as translating macro controls 50b along direction D10 (see FIGS. 17A-17C). As instrument 4 is coupled with actuator 40 via instrument holder 4a, translation of actuator 40 along direction D10 correspondingly translates instrument 4 along direction D12. In one embodiment, the translating of articulating surgical instrument 4 along direction D12 occurs in response to a displacement of hydraulic fluid generated in the control portion by the movement along the third degree of freedom. In one embodiment, macro control portion 50b translates the motion along direction D10 to a linear motion of one or more master control cylinders 100. Hydraulic lines may then transmit control signals, in the form of displacement of hydraulic fluid, generated from the linear motion of master control cylinder(s) 100 to one or more corresponding slave control cylinders 100 in slave portion 70 to effect motion of components of slave 70 (such as motion of actuator 40 along direction D11) that are coupled to the corresponding slave control cylinders in slave portion 70. This causes instrument 4, which is coupled to actuator 40 via instrument holder 4*a*, to correspondingly translate (extend/retract) along direction D12 (FIGS. 17D-16E). It is appreciated that other motions, translating or otherwise, can be produced by orienting components in a different fashion within slave portion 70. In the interest of brevity and clarity, reference is made to FIGS. 17A-17E for further description of the mechanics and process of translating instrument 4 along direction D12 in response to motion imparted by a user to control portion 50 of device 1.

At 2540 of flow diagram 2500, in one embodiment, the articulating surgical instrument is rotated about a primary axis of the articulating surgical instrument. According to one embodiment, FIG. 18A illustrates one example of such rotation by depicting rotation 1800*a* of instrument 4 about primary axis 1901. This rotation about a primary axis of the articulating surgical instrument occurs in response to movement of a portion of control portion 50 along a fourth degree of freedom. For example, with reference to FIG. 18B, rotation 1800*b* of arm holder assembly 1100 of micro controls 50*a* can comprise the movement along the fourth degree of freedom. The movement along the fourth degree of freedom of movement of control portion 50 can be imparted to control portion 50 by the same human arm that is used to impart motion along the first, second, and third degrees of freedom. The fourth degree of freedom is a different degree of freedom of movement of control portion 50 than the first, second, and third degrees of freedom.

As has been described herein in conjunction with FIGS. 18A-18B, in one embodiment, this comprises rotating 1800*a* instrument 4 about axis 1901 in response to a motion being imparted to micro controls 50*a*, such as rotating 1800*b* arm holder assembly 1100 about axis F or alternatively by rotating thumbwheel 2410 (as is described in conjunction with FIG. 24A). In one embodiment, rotating articulating surgical instrument 4 about primary axis 1901 occurs in response to a displacement of hydraulic fluid, generated in control portion 50 by the rotation of arm holder assembly 1100 in the fourth degree of freedom or the rotation of thumbwheel 2410 in a fourth degree of freedom. For example, in one embodiment, micro control portion 50*a* translates rotation of arm holder assembly 1100 about axis F or the rotation of thumbwheel 2410 into a linear motion of one or more master control cylinders 100. Hydraulic lines may then transmit control signals, in the form of displacement of hydraulic fluid, generated from the linear motion of master control cylinder(s) 100, to one or more corresponding slave control cylinders of instrument 4 (such as slave control cylinder 1440'). This causes instrument 4, to rotate 1800*a* about primary axis 1901. It is appreciated that other motions, rotating or otherwise, can be produced by orienting components in a different fashion within instrument 4 and/or slave portion 70. In the interest of brevity and clarity, reference is made to FIGS. 18A and 18B for further description of the mechanics and process of rotating instrument 4 about a primary axis of instrument 4 in response to motion imparted by a user to control portion 50 of device 1.

At 2550 of flow diagram 2500, in one embodiment, a wrist bend motion is actuated in the articulating surgical instrument. According to one embodiment, FIG. 18A illustrates one example of such a wrist bend by wrist bend motion 1801*a* of instrument 4. This wrist bend motion 1801*a* of the articulating surgical instrument occurs in response to movement of a portion of control portion 50 along a fifth degree of freedom. For example, with reference to FIG. 18B, pivoting 1801*b* of grasper frame 1230 around axis W of micro controls 50*a* can comprise the movement along the fifth degree of freedom. The movement along the fifth degree of freedom of movement of control portion 50 can be imparted to control portion 50 by the same human shoulder, arm, and/or hand used to impart motion along the first, second, third and fourth degrees of freedom. For example, the fifth degree of motion may be imparted by using a wrist bend motion of the user's wrist while the user grasps grasper handle assembly 1200. The fifth degree of freedom is a different degree of freedom of movement of control portion 50 than the first, second, third, and fourth degrees of freedom.

As has been described herein in conjunction with FIGS. 18A-18B, in one embodiment, this comprises bending 1801*a* a portion of instrument 4 in response to a motion being imparted to micro controls 50*a*, such as pivoting grasper frame 1230 of micro controls 50*a* about axis W. In one embodiment, bending 1801*a* in articulating surgical instrument 4 occurs in response to a displacement of hydraulic fluid, generated in control portion 50 by the pivoting of grasper frame 1230 in the fifth degree of freedom. For example, in one embodiment, micro control portion 50*a* translates pivoting of grasper frame 1230 about axis W into a linear motion of one or more master control cylinders 100. Hydraulic lines may then transmit control signals, in the form of displacement of hydraulic fluid, generated from the linear motion of master control cylinder(s) 100, to one or more corresponding slave control cylinders in instrument 4 (such as slave control cylinder 1430') to effect a bending motion 1801*a* of instrument 4. It is appreciated that other motions, bending or otherwise, can be produced by orienting components in a different fashion within instrument 4 and/or slave portion 70. In the interest of brevity and clarity, reference is made to FIGS. 18A and 18B for further description of the mechanics and process of performing a wrist bend motion 1801*a* with instrument 4 in response to motion imparted by a user to control portion 50 of device 1.

At 2560 of flow diagram 2500, in one embodiment, a tip rotate motion is actuated in the articulating surgical instrument. According to one embodiment, FIG. 18A illustrates one example of such a tip rotate motion 1802*a* of instrument 4. This tip rotate motion 1802*a* of the articulating surgical instrument occurs in response to movement of a portion of control portion 50 along a sixth degree of freedom. For example, with reference to FIG. 18B, rotating 1802*b* grasper handle 1210 around axis T of micro controls 50*a* can comprise the movement along the sixth degree of freedom. The movement along the sixth degree of freedom of movement of control portion 50 can be imparted to control portion 50 by the same human shoulder, arm, and/or hand used to impart motion along the first, second, third, fourth, and fifth degrees of freedom. For example, the sixth degree of motion may be imparted by using a wrist rotate motion while the user grasps grasper handle assembly 1200. The sixth degree of freedom is a different degree of freedom of movement of control portion 50 than the first, second, third, fourth, and fifth degrees of freedom.

As has been described herein in conjunction with FIGS. 18A-18B, in one embodiment, this comprises rotating 1802*a* a tip portion of instrument 4 in response to a motion being imparted to micro controls 50*a*, such as rotating grasper handle 1210 of micro controls 50*a* about axis T. In one embodiment, tip rotating 1802*a* in articulating surgical instrument 4 occurs in response to a displacement of hydraulic fluid, generated in control portion 50 by the rotating of grasper handle 1210 in the sixth degree of freedom. For example, in one embodiment, micro control portion 50*a* translates rotation 1802*b* of grasper handle 1210 about axis T into a linear motion of one or more master control cylinders 100. Hydraulic lines may then transmit control signals, in the form of displacement of hydraulic fluid, generated from the linear motion of master control cylinder(s) 100, to one or more corresponding slave control cylinders in instrument 4 (such as slave control cylinder 1410') to effect a tip rotating motion 1802*a* of instrument 4. It is appreciated that other motions, tip rotating or otherwise, can be produced by orienting components in a different fashion within instrument 4 and/or slave portion 70. In the interest of brevity and clarity, reference is made to FIGS. 18A and 18B for further description of the mechanics and process of performing a tip rotate motion with instrument 4 in response to motion imparted by a user to control portion 50 of device 1.

At 2570 of flow diagram 2500, in one embodiment a tip grasp motion is actuated in the articulating surgical instrument. According to one embodiment, FIG. 18A illustrates one example of such a tip grasp motion 1803*a* of instrument 4. This tip grasp motion 1803*a* of the articulating surgical instrument occurs in response to movement of a portion of control portion 50 along a seventh degree of freedom. For example, with reference to FIG. 18B, rotating 1803*b* trigger 1220 around grasp axis G (by squeezing or pushing trigger 1220) of micro controls 50*a* can comprise the movement along the seventh degree of freedom. The movement along the seventh degree of freedom of movement of control portion 50 can be imparted to control portion 50 by the same human shoulder, arm, and/or hand used to impart motion along the first, second, third, fourth, fifth, and sixth degrees of freedom. For example, the seventh degree of motion may be imparted by squeezing trigger 1220 with one or more fingers or pushing thumb flange 1222 with a thumb or with the same fingers used for squeezing, while the user grasps grasper handle assembly 1200. The seventh degree of freedom is a different degree of freedom of movement of control portion 50 than the first, second, third, fourth, fifth, and sixth degrees of freedom.

As has been described herein in conjunction with FIGS. 18A-18B, in one embodiment, this comprises performing a tip grasp motion 1803*a* with a tip portion of instrument 4 in response to a motion being imparted to micro controls 50*a*, such as a squeeze or push of trigger 1220 of micro controls 50*a*. In one embodiment, tip grasping 1803*a* in articulating surgical instrument 4 occurs in response to a displacement of hydraulic fluid, generated in control portion 50 by the pivoting of trigger 1220 in the seventh degree of freedom. For example, in one embodiment, micro control portion 50*a* translates pivoting of trigger 1220 about axis G into a linear motion of one or more master control cylinders 100. Hydraulic lines may then transmit control signals, in the form of displacement of hydraulic fluid, generated from the linear motion of master control cylinder(s) 100, to one or more corresponding slave control cylinders in instrument 4 (such as slave control cylinder 1420') to effect a tip grasping motion 1803*a* (which can include both open and close motions of the tip) of instrument 4. It is appreciated that other motions, grasping or otherwise, can be produced by orienting components in a different fashion within instrument 4 and/or slave portion 70. In the interest of brevity and clarity, reference is made to FIGS. 18A and 18B for further description of the mechanics and process of performing a tip grasping motion with instrument 4 in response to motion imparted by a user to control portion 50 of device 1

Example Method of Articulation Control Signal Generation

Figure 26A:
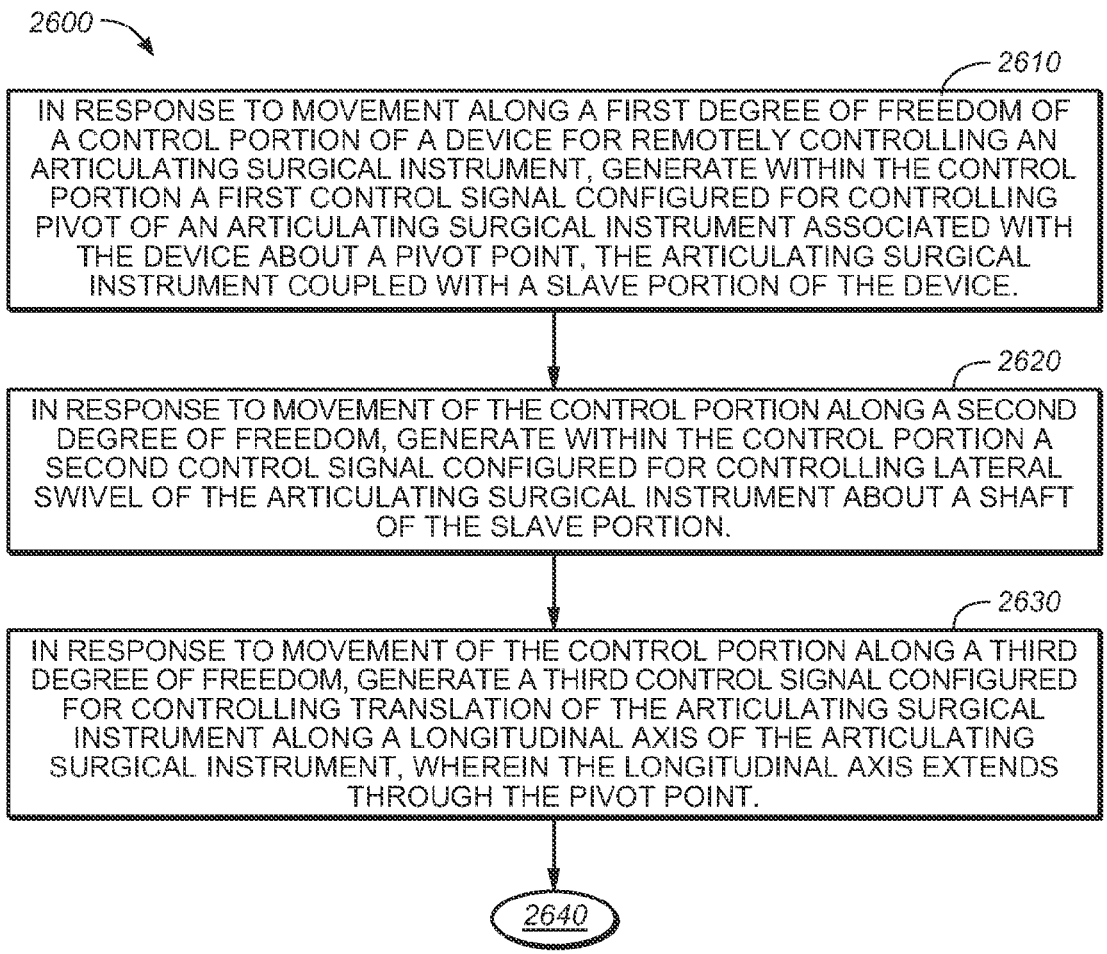
FIGS. 26A and 26B illustrate a flow diagram of an example method of articulation control signal generation, in accordance with various embodiments of the present invention.
Figure 26B:
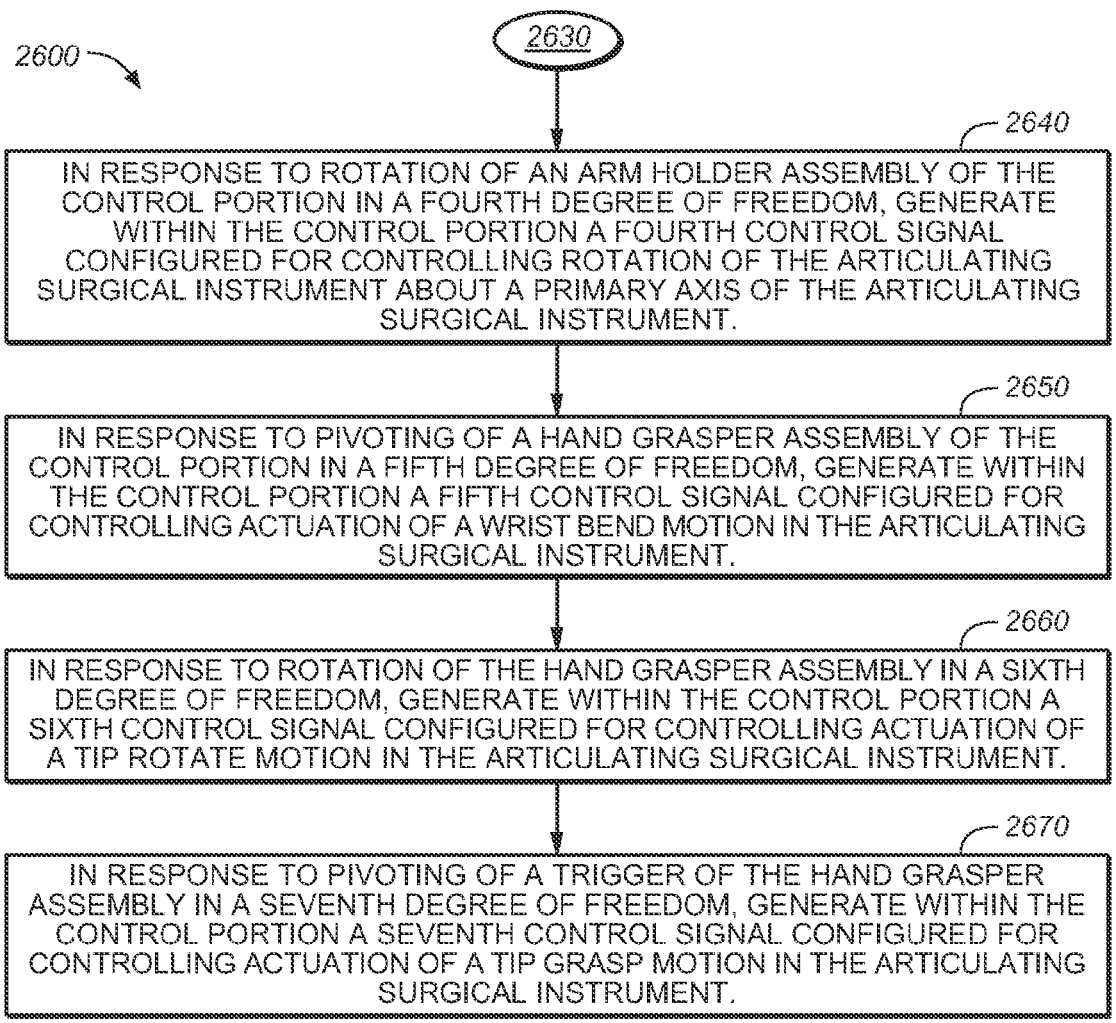

FIGS. 26A and 26B illustrate a flow diagram 2600 of an example method of articulation control signal generation, according to one embodiment. According to one embodiment, flow diagram 2600 illustrates an example method of control portion 50 generating articulation control signals for the control of slave portion 70 and/or articulating surgical instrument 4. Although specific procedures are disclosed in flow diagram 2600, such procedures are example. That is, embodiments of the present invention are well suited to performing various other procedures or variations of the procedures recited in flow diagram 2600. It is appreciated that the procedures in flow diagram 2600 may be performed in an order different than presented, and that not all of the procedures described in flow diagram 2600 may be performed in every embodiment. In the description of the procedures of the method of flow diagram 2600, reference will be made to elements of FIGS. 1A-23, to include reference to control portion 50 (and components thereof), slave portion 70 (and components thereof), and instrument 4 (and components thereof).

At 2610 of flow diagram 2600, in one embodiment, a first control signal is generated within the control portion in response to movement along a first degree of freedom of a control portion of a "device" for remotely controlling an articulating surgical instrument. The first control controls pivot of an articulating surgical instrument, associated with the device. That is, in one embodiment the articulating surgical instrument is the instrument which the device remotely controls. The pivoting takes place about a pivot point which, in one embodiment, is located external to an operating environment (where the operating environment is considered to be the environment within a patient being operated on by the articulating surgical instrument). Device 1 is one example of such a device for remotely controlling an articulating surgical instrument, control portion 50 is one example of a control portion, and instrument 4 is one example of an articulating surgical instrument that may be controlled by control portion 50 of device 1. In one embodiment, as illustrated in FIGS. 1A, 1C, 7-12A, 14D, 15A, 16D, 16E, 17D, and 17E articulating surgical instrument 4 is coupled with a slave portion 70 of device 1.

As has been described herein in conjunction with FIGS. 14A-14E and FIGS. 15A-15E, in one embodiment the pivoting about the pivot point occurs in response to a movement along a first degree of freedom of all or some portion of control portion 50 of device 1. The movement along a first degree of freedom of movement can be imparted to control portion 50 by a human shoulder, arm, and/or hand of a user of device 1. In one embodiment, the pivoting of articulating surgical instrument 4 about the pivot point occurs in response to a first control signal, in the form of a third displacement of hydraulic fluid, that is generated in the control portion by the movement along the first degree of freedom. In one embodiment, a user may input a motion in a first degree of freedom of motion, by swiveling the entire micro control assembly 50*a* along arc D2 about pivot point 401. In one embodiment, macro control portion 50*b* of control portion 50 then translates swiveling motion along arc D2 to a linear motion of one or more master control cylinders 100 to generate the first control signal. Hydraulic lines may then transmit this first control to one or more corresponding slave control cylinders 100 in slave portion 70 to effect motion of components of slave 70 that are coupled to the corresponding slave control cylinder(s) in slave portion 70. In this, the first control signal causes instrument holder 4a and the instrument 4 (coupled thereto) and portions of slave portion 70 to pivot about Pivot Point 2 (FIGS. 15A and 15B). In one embodiment, Pivot Point 2 is designed to be located external to an operating environment (that is, external to the body of a patient being operated upon), however in other embodiments, Pivot Point 2 may be within an operating environment. In the interest of brevity and clarity, reference is made to FIGS. 14A-14E and 15A-15E for further description of the mechanics and process of pivoting instrument 4 about a pivot point in response to motion imparted by a user to control portion 50 of device 1.

At 2620 of flow diagram 2600, in one embodiment, a second control signal is generated within the control portion in response to movement of the control portion along a second degree of freedom. The second control signal controls lateral swivel of the articulating surgical instrument about a shaft of the slave portion. The shaft is located external to the operating environment. This lateral swiveling occurs in response to movement of all or some portion of control portion 50 along a second degree of freedom. The movement along the second degree of freedom can be imparted to control portion 50 by the same human shoulder, arm, and/or hand used to impart motion along the first degree of freedom. The second degree of freedom is a different degree of freedom of movement of control portion 50 than the first degree of freedom.

As has been described herein in conjunction with FIGS. 16A-16F, in one embodiment, the swiveling controlled by the second control signal comprises swiveling (see arc D8 of FIGS. 16D-16E) instrument 4 about shaft 550 (as is depicted and described in conjunction with FIGS. 16D-16F). The second control signal is generated in response to a motion being imparted to macro controls 50b, such as swiveling macro controls 50b along arc D6 (see FIG. 16A). In one embodiment, the laterally swiveling of articulating surgical instrument 4 about shaft 550a occurs in response to a second control signal, in the form of a second displacement of hydraulic fluid, generated in the control portion by the movement along the second degree of freedom. In one embodiment, macro control portion 50b of control portion 50 translates swiveling motion along arc D6 to a linear motion of one or more master control cylinders 100 to generate the second control signal. Hydraulic lines may then transmit the second control signal to one or more corresponding slave control cylinders 100 in slave portion 70 to effect motion of components of slave 70 (such as motion of shaft 550a) that are coupled to the corresponding slave control cylinder(s) in slave portion 70. In this manner, the second control signal causes instrument 4, which is coupled to shaft 550a, to laterally swivel about arc D8 (FIGS. 16D-16E). In the interest of brevity and clarity, reference is made to FIGS. 16A-16E for further description of the mechanics and process of laterally swiveling instrument 4 along arc D8 in response to motion imparted by a user to control portion 50 of device 1.

At 2630 of flow diagram 2600, in one embodiment, a third control signal is generated in response to movement of the control portion along a third degree of freedom. The third control signal controls translation of the articulating surgical instrument along a longitudinal axis of the articulating surgical instrument. In one embodiment, this longitudinal axis extends through the pivot point (e.g., Pivot Point 2) about which the articulating surgical instrument can be pivoted. This translating along the longitudinal axis occurs in response to movement of at least a portion of control portion 50 along a third degree of freedom. The movement along the third degree of freedom of movement of control portion 50 can be imparted to control portion 50 by the same human shoulder, arm, and/or hand used to impart motion along the first and second degrees of freedom. The third degree of freedom is a different degree of freedom of movement of control portion 50 than the first and second degrees of freedom.

As has been described herein in conjunction with FIGS. 17A-17E, in one embodiment, the longitudinal translation controlled by the third control signal comprises control cylinder 100 (of extending and retracting actuator 40 of slave portion 70) moving along direction D11 (as is depicted and described in conjunction with FIGS. 16E-17D). The third control signal is generated in response to a motion being imparted to macro controls 50b, such as translating macro controls 50b along direction D10 (see FIGS. 17A-17C). As instrument 4 is coupled with extending/retracting actuator 40 via instrument holder 4a, translation of actuator 40 along direction D10 correspondingly translates instrument 4 along direction D12. In one embodiment, the translating of articulating surgical instrument 4 along direction D12 occurs in response to a third control signal, in the form of a third displacement of hydraulic fluid, generated in control portion 50 by the movement along the third degree of freedom. Macro control portion 50b translates motion along direction D10 to a linear motion of one or more master control cylinders 100 to generate the third control signal. Hydraulic lines may then transmit the third control signal to one or more corresponding slave control cylinders 100 in slave portion 70 to effect motion of components of slave 70 (such as motion of actuator 40 along direction D11) that are coupled to the corresponding slave control cylinders in slave portion 70. In this manner, the third control signal causes instrument 4, which is coupled to actuator 40 via instrument holder 4a, to correspondingly translate (extend/retract) along direction D12 (FIGS. 17D-16E). In the interest of brevity and clarity, reference is made to FIGS. 17A-17E for further description of the mechanics and process of translating instrument 4 along direction D12 in response to motion imparted by a user to control portion 50 of device 1.

At 2640 of flow diagram 2600, in one embodiment, a fourth control signal is generated within the control portion in response to rotation of an arm holder assembly of the control portion in a fourth degree of freedom. Additionally or alternatively, in some embodiments the fourth control signal is generated within the control portion in response to rotation of thumbwheel 2410 in a fourth degree of freedom. The fourth control signal controls rotation of the articulating surgical instrument about a primary axis of the articulating surgical instrument. According to one embodiment, FIG. 18A illustrates one example of such rotation by depicting rotation 1800a of instrument 4 about primary axis 1901. With reference to FIG. 18B, rotation 1800b of arm holder assembly 1100 of micro controls 50a or thumb wheel 2410 of micro controls 50a can comprise the movement along the fourth degree of freedom causes generation of the fourth control signal. The movement along the fourth degree of freedom of movement of control portion 50 can be imparted to control portion 50 by the same human shoulder, arm, and/or hand used to impart motion along the first, second, and third degrees of freedom. The fourth degree of freedom is a different degree of freedom of movement of control portion 50 than the first, second, and third degrees of freedom.

As has been described herein in conjunction with FIGS. 18A-18B, in one embodiment, the motion controlled by the fourth control signals comprises rotating 1800a instrument 4 about axis 1901 in response to a motion being imparted to micro controls 50*a*, such as rotating 1800*b* arm holder assembly 1100 about axis F. In one embodiment, rotating articulating surgical instrument 4 about primary axis 1901 occurs in response to a fourth control signal, in the form of a fourth displacement of hydraulic fluid, generated in control portion 50 by the rotation of arm holder assembly 1100 in the fourth degree of freedom. For example, in one embodiment, micro control portion 50*a* translates rotation of arm holder assembly 1100 about axis F or rotation of thumbwheel 2410 into a linear motion of one or more master control cylinders 100 to generate the fourth control signal. Hydraulic lines may then transmit the fourth control signal to one or more corresponding slave control cylinders of instrument 4 (such as slave control cylinder 1440'). In this manner, the fourth control signal causes instrument 4, to rotate 1800*a* about primary axis 1901. In the interest of brevity and clarity, reference is made to FIGS. 18A and 18B for further description of the mechanics and process of rotating instrument 4 about a primary axis of instrument 4 in response to motion imparted by a user to control portion 50 of device 1.

At 2650 of flow diagram 2600, in one embodiment, a fifth control signal is generated within the control portion in response to pivoting of a grasper handle assembly of the control portion in a fifth degree of freedom. The fifth control signal controls actuation of a wrist bend motion in the articulating surgical instrument. According to one embodiment, FIG. 18A illustrates one example of such a wrist bend by wrist bend motion 1801*a* of instrument 4. This wrist bend motion 1801*a* of the articulating surgical instrument occurs in response to movement of a portion of control portion 50 along a fifth degree of freedom. For example, with reference to FIG. 18B, pivoting 1801*b* of grasper frame 1230 around axis W of micro controls 50*a* can comprise the movement along the fifth degree of freedom. The movement along the fifth degree of freedom of movement of control portion 50 can be imparted to control portion 50 by the same human shoulder, arm, and/or hand used to impart motion along the first, second, third and fourth degrees of freedom. For example, the fifth degree of motion may be imparted by using a wrist bend motion 1801*b* of the user's wrist while the user grasps grasper handle assembly 1200. The fifth degree of freedom is a different degree of freedom of movement of control portion 50 than the first, second, third, and fourth degrees of freedom.

As has been described herein in conjunction with FIGS. 18A-18B, in one embodiment, the motion controlled by the fifth control signal comprises bending 1801*a* a portion of instrument 4 in response to a motion being imparted to micro controls 50*a*, such as pivoting grasper frame 1230 of micro control 50*a* about axis W. In one embodiment, bending 1801*a* in articulating surgical instrument 4 occurs in response to a fifth control signal, in the form of a fifth displacement of hydraulic fluid, generated in control portion 50 by the pivoting of grasper frame 1230 in the fifth degree of freedom. For example, in one embodiment, micro control portion 50*a* translates pivoting of grasper frame 1230 about axis W into a linear motion of one or more master control cylinders 100 to generate the fifth control signal. Hydraulic lines may then transmit the fifth control signal, to one or more corresponding slave control cylinders in instrument 4 (such as slave control cylinder 1430') to effect a bending motion 1801*a* of instrument 4. In the interest of brevity and clarity, reference is made to FIGS. 18A and 18B for further description of the mechanics and process of performing a wrist bend motion with instrument 4 in response to motion imparted by a user to control portion 50 of device 1.

At 2660 of flow diagram 2600, in one embodiment, a sixth control signal is generated within the control portion. The sixth control signal controls actuation of a tip rotate motion in the articulating surgical instrument. The sixth control signal is generated in response to rotation of said grasper handle assembly in a sixth degree of freedom. According to one embodiment, FIG. 18A illustrates one example of such a tip rotate motion 1802*a* of instrument 4. This tip rotate motion 1802*a* of the articulating surgical instrument occurs in response to movement of a portion of control portion 50 along a sixth degree of freedom. For example, with reference to FIG. 18B, rotating 1802*b* grasper handle 1210 around axis T of micro controls 50*a* can comprise the movement along the sixth degree of freedom. The movement along the sixth degree of freedom of movement of control portion 50 can be imparted to control portion 50 by the same human shoulder, arm, and/or hand used to impart motion along the first, second, third, fourth, and fifth degrees of freedom. For example, the sixth degree of motion may be imparted by using a wrist rotate motion while the user grasps grasper handle assembly 1200. The sixth degree of freedom is a different degree of freedom of movement of control portion 50 than the first, second, third, fourth, and fifth degrees of freedom.

As has been described herein in conjunction with FIGS. 18A-18B, in one embodiment, the motion controlled by the sixth control signal comprises rotating 1802*a* a tip portion of instrument 4 in response to a motion being imparted to micro controls 50*a*, such as rotating grasper handle 1210 of micro controls 50*a* about axis T. In one embodiment, tip rotating 1802*a* in articulating surgical instrument 4 occurs in response to a sixth control signal, in the form of a sixth displacement of hydraulic fluid, generated in control portion 50 by the rotating of grasper handle 1210 in the sixth degree of freedom. For example, in one embodiment, micro control portion 50*a* translates rotation 1802*b* of grasper handle 1210 about axis T into a linear motion of one or more master control cylinders 100 to generate the sixth control signal. Hydraulic lines may then transmit the sixth control signal, to one or more corresponding slave control cylinders in instrument 4 (such as slave control cylinder 1410') to effect a tip rotating motion 1802*a* of instrument 4. In the interest of brevity and clarity, reference is made to FIGS. 18A and 18B for further description of the mechanics and process of performing a tip rotate motion with instrument 4 in response to motion imparted by a user to control portion 50 of device 1.

At 2670 of flow diagram 2600, in one embodiment, a seventh control signal is generated within the control portion. The seventh control signal controls actuation of a tip grasp motion in the articulating surgical instrument in response to pivoting of a trigger of the grasper handle assembly in a seventh degree of freedom. According to one embodiment, FIG. 18A illustrates one example of such a tip grasp motion 1803*a* of instrument 4. This tip grasp motion 1803*a* of the articulating surgical instrument occurs in response to movement of a portion of control portion 50 along a seventh degree of freedom. For example, with reference to FIG. 18B, rotating 1803*b* trigger 1220 around grasp axis G (by squeezing or pushing trigger 1220) of micro controls 50*a* can comprise the movement along the seventh degree of freedom. The movement along the seventh degree of freedom of movement of control portion 50 can be imparted to control portion 50 by the same human shoulder, arm, and/or hand used to impart motion along the first, second, third, fourth, fifth, and sixth degrees of freedom. For example, the seventh degree of motion may be imparted by squeezing finger loop 1214 of trigger 1220 with one or more fingers or pushing trigger thumb flange 1222 with a thumb or pushing on finger loop 1214 with the same finger(s) used for squeezing, while the user grasps grasper handle assembly 1200. The seventh degree of freedom is a different degree of freedom of movement of control portion 50 than the first, second, third, fourth, fifth, and sixth degrees of freedom.

As has been described herein in conjunction with FIGS. 18A-18B, in one embodiment, the motion controlled the seventh control signal comprises performing a tip grasp motion 1803a with a tip portion of instrument 4 in response to a motion being imparted to micro controls 50a, such as a squeeze or push of trigger 1220 of micro controls 50a. In one embodiment, tip grasping 1803a in articulating surgical instrument 4 occurs in response to a seventh control signal, in the form of a seventh displacement of hydraulic fluid, generated in control portion 50 by the pivoting of trigger 1220 in the seventh degree of freedom. For example, in one embodiment, micro control portion 50a translates pivoting of trigger 1220 about axis G into a linear motion of one or more master control cylinders 100 to generate the seventh control signal. Hydraulic lines may then transmit the seventh control signal to one or more corresponding slave control cylinders in instrument 4 (such as slave control cylinder 1420') to effect a tip grasping motion 1803a (which can include both open and close motions of the tip) of instrument 4. In the interest of brevity and clarity, reference is made to FIGS. 18A and 18B for further description of the mechanics and process of performing a tip grasping motion with instrument 4 in response to motion imparted by a user to control portion 50 of device 1.

Example Method of Remotely Controlled Surgical Device Control Signal Generation

Figure 27:
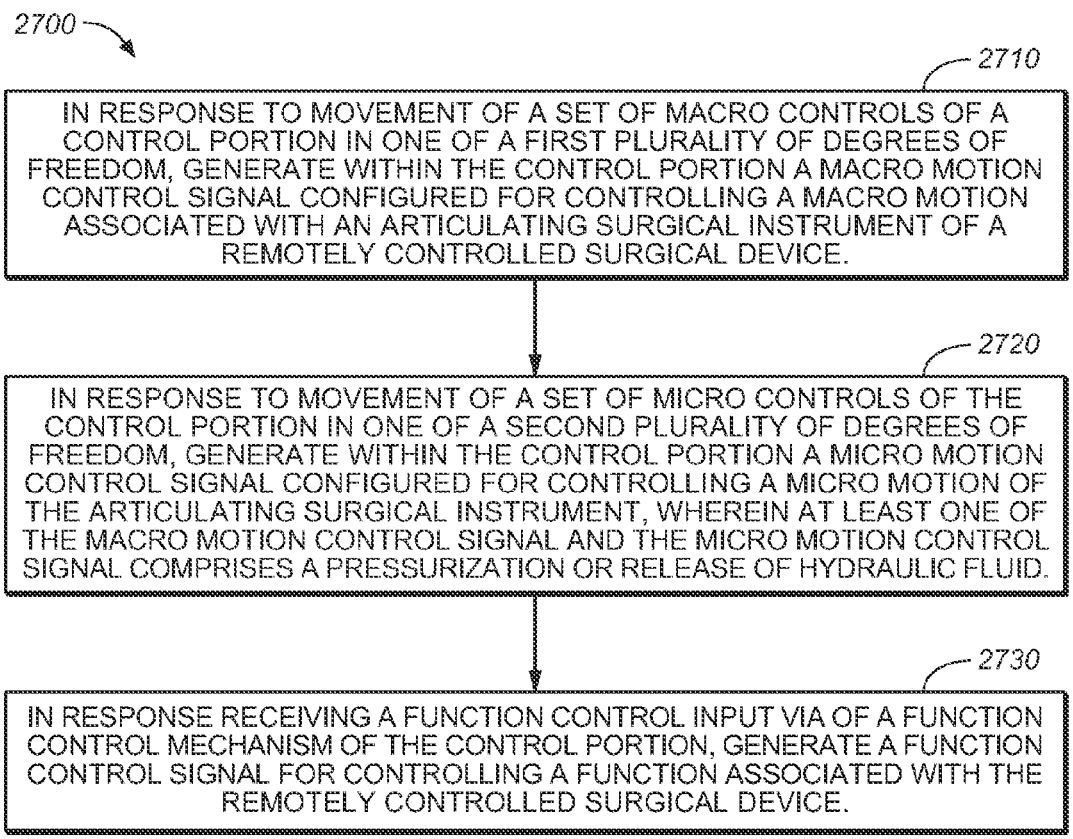
FIG. 27 illustrates a flow diagram of an example method of remotely controlled surgical device control signal generation, in accordance with various embodiments of the present invention.

FIG. 27 illustrates a flow diagram 2700 of an example method of remotely controlled surgical device 1 control signal generation, according to one embodiment. According to one embodiment, flow diagram 2700 illustrates an example method of control portion 50 generating control signals. These control signals can comprise articulation control signals for the control of slave portion 70 and/or articulating surgical instrument 4. These control signals can also comprise one or more function control signals for controlling a function associated with remotely controlled surgical device 1. A function control signal may be generated to control a function associated with any portion of device 1, including: control portion 50, slave portion 70, and/or articulating surgical instrument 4. In some instances a function control signal may include the generation of no signal at all, such as by locking a control signal in a manner that it cannot be altered by a user input (e.g., via ratchet 2450). Although specific procedures are disclosed in flow diagram 2700, such procedures are example. That is, embodiments of the present invention are well suited to performing various other procedures or variations of the procedures recited in flow diagram 2700. It is appreciated that the procedures in flow diagram 2700 may be performed in an order different than presented, and that not all of the procedures described in flow diagram 2700 may be performed in every embodiment. In the description of the procedures of the method of flow diagram 2700, reference will be made to various elements of FIGS. 1A-23, and 26A and 26B to include reference to control portion 50 (and components thereof), slave portion 70 (and components thereof), and instrument 4 (and components thereof).

At 2710 of flow diagram 2700, in one embodiment, a macro motion control signal is generated within the control portion. The macro motion control signal is configured for controlling a macro motion associated with an articulating surgical instrument of a remotely controlled surgical device. The macro motion control signal is generated in response to movement of all or a part of a first set of controls 50b (which are a subset of control portion 50) in one of a first plurality of degrees of freedom. As previously described in 2610, 2620, and 2630 of the method of flow diagram 2600, macro controls 50b can be moved in at least three separate degrees of freedom of movement (described in conjunction with the method of flow diagram 2600 as first, second, and third degrees of freedom of movement) to generate macro control signals for controlling movements of slave portion 70 which is coupled to and thus moves instrument 4 in one or more macro motions.

With reference to flow diagram 2600, in one embodiment, an shoulder, arm, and/or hand of a user may of input movements to macro controls 50b in any of these three separate degrees of freedom of movement. For example, an input in the first degree of freedom of movement causes macro controls 50b to generate an articulation control signal for controlling pivot of an articulating surgical instrument 4 of device 1; while an input in the second degree freedom of movement causes macro controls 50b generate a control signal for control lateral swivel of the articulating surgical instrument 4 about a shaft of the slave portion 70; and while an input in the third degree of freedom of movement causes macro controls 50b to generate a control signal control for controlling translation (extension/retraction) of articulating surgical instrument 4 along a longitudinal axis of the articulating surgical instrument 4. Any of the inputs in the first plurality of degrees of freedom of movement may occur simultaneously with one another or independently in time from one another.

As previously described, in some embodiments, a macro motion control signal may comprise a displacement of hydraulic fluid within control portion 50 that may then be coupled via hydraulic lines to one or more control cylinders within slave portion 70 as hydraulic signals for controlling of the motion of these one or more slave control cylinders. In other embodiments, the macro motion control signal may comprise an electrical signal, a mechanical signal (movement of a cable or rod) or some combination of hydraulic, electrical, and mechanical signals.

At 2720 of flow diagram 2700, in one embodiment, a micro motion control signal is generated within the control portion. The micro motion control signal is configured for controlling a micro motion of the articulating surgical instrument of a remotely controlled surgical device. The micro motion control signal is generated in response to movement of all or a part of a set of micro controls 50a (which are a subset of control portion 50) in one of a second plurality of degrees of freedom. As previously described in 2610, 2620, and 2630 of the method of flow diagram 2600, macro controls 50b can be moved in at least four separate degrees of freedom of movement (described in conjunction with the method of flow diagram 2600 as fourth, fifth, sixth, and seventh degrees of freedom of movement) to generate macro control signals for controlling movements of slave portion 70 which is coupled to and thus moves instrument 4 in one or more macro motions. These four separate degrees of freedom of movement are separate and different from the first plurality of degrees of freedom of movement.

With reference to flow diagram 2600, in one embodiment, the same shoulder, arm, and/or hand of a user that are used to input any of the first plurality of degrees of movement to macro controls 50b may provide input movements to micro controls 50a in any of the four separate degrees of freedom of movement of the second plurality of degrees of freedom of movement. For example, an input in the first degree of freedom of movement causes macro controls 50b to generate an articulation control signal for controlling pivot of an articulating surgical instrument 4 of device 1; while an input in the second degree freedom of movement causes macro controls

50b generate a control signal for control lateral swivel of the articulating surgical instrument 4 about a shaft of the slave portion 70; and while an input in the third degree of freedom of movement causes macro controls 50b to generate a control signal control for controlling translation (extension/retraction) of articulating surgical instrument 4 along a longitudinal axis of the articulating surgical instrument 4. Any of the inputs in the second plurality of degrees of freedom of movement may occur simultaneously with one or independently in time from one another. Similarly, any input in the first plurality of degrees of freedom of movement may occur simultaneously or independently in time from inputs in the first plurality of degrees of freedom of movement. This means that control portion 50 may generate macro and micro control signals simultaneously or one at a time, depending on the number of and timing of movement inputs which are received by control portion 50.

As previously described, in some embodiments, a micro motion control signal may comprise a displacement of hydraulic fluid within control portion 50 that may then be coupled via hydraulic lines to one or more control cylinders within instrument 4 as hydraulic signals for controlling of the motion of these one or more slave control cylinders. In other embodiments, the micro motion control signal may comprise an electrical signal, a mechanical signal (e.g., movement of a cable, rod, or linkage) or some combination of hydraulic, electrical, and mechanical signals.

At 2730 of flow diagram 2700, in one embodiment, a function control signal is generated within the control portion. The function control signal is configured for controlling a function associated with remotely controlled surgical device 1. The function may control a function of any portion of device 1. In one embodiment, the function control signal is an interrupt which interrupts some other signal between its source and its destination proximal to an instrument 4 and/or tool 7. The function control signal is generated in response to receiving an input via a function control mechanism of control portion 50. For example, function control mechanism 50c may a lever, trigger, screw, button, latch, switch, paddle, moveable pin, knob, ratcheting selector, pedal (e.g., a foot pedal), touchless sensor, dial, pressure sensor, or other input. In one embodiment, function control mechanism 50c may be disposed as a portion of grasper handle assembly 1200; such that it may be directly manipulated by the same shoulder, arm, and/or hand which provides inputs to micro controls 50a and macro controls 50b. For example, as illustrated in FIG. 12B, function control mechanism 50c is implemented as knob 50c-1 which disposed upon grasper handle assembly 1200 such that it may be spun by a finger or thumb of user U while utilizing grasper handle assembly 1200. Lever 2455 of ratchet 2450 is another example of a function control mechanism. The input motion may be a different degree of freedom of movement than any of the first and second pluralities of degrees of freedom of movement. In another embodiment, a function control mechanism 50c may be disposed at a physically separate location from micro controls 50a and 50b, such as in the form of a foot pedal 50c-2 (as illustrated in FIG. 13A) which a user may move with a foot to trigger/control a function of device 1. In one embodiment, function control mechanism 50c may be imbedded within micro controls 50a or macro controls 50b. For example, a pressure sensor coupled to a control cylinder could be utilized to receive coded inputs (such as three quick and timed tip rotate 1802b inputs) for interpretation by processor 2310 as a user input which causes processor 2310 to generate function control signal to control a function of device 1.

Some examples of functions of device 1 that may a function control signal may be generated to control include, but are not limited to: illumination, control locking, irrigation, suction, magnetization, viewing (e.g., camera), cauterization, therapeutic energy emission (e.g., ultrasonic, light, heat, laser emissions from instrument 4). Illumination can comprise turning on/off or varying intensity of an illumination function of instrument 4. Such an illumination function may comprise, for example, light supplied via fiber optic fiber routed from control portion 50 to instrument 4 or light generated by electricity at some location on instrument 4 (such as by a light emitting diode disposed near a distal tip of instrument 4). Control locking can comprise locking out all or part of control portion 50, such that the locked out portion(s) cannot generate inputs which cause movement of instrument 4. Irrigation can comprise enabling/disabling and/or controlling the flow rate of irrigation fluid, such as saline or water, that is routed to and expelled from a portion of instrument 4 (e.g., at a location near the distal tip). Suction can comprise enabling/disabling and/or controlling the rate of suction that is routed to and available for use at portion of instrument 4 (e.g., at a location near the distal tip). Viewing can comprise turning on/off or adjusting the viewpoint of a camera or viewing device (e.g., a lens coupled with a fiber optic fiber) which is positioned on a portion of instrument 4 (e.g., proximal to a distal tip). Magnetization can comprise enabling/disabling and/or adjusting the intensity of magnetization of a portion of instrument 4. For example, a distal tip portion of instrument 4 may be magnetized by an electromagnet to engage and hold in place a tool 7 and demagnetized to allow release of tool 7. In a similar manner, a function control signal may be generated to control application/removal and/or variance of the amount of power supplied to any electrically powered function or portion associated with device 1, instrument 4, and/or a tool 7. Electrical lines and or control signal lines for routing one or more function control signals may be routed along or through instrument 4 to desired points. For example, electrical power may be applied/removed and/or varied to control cauterization by a cauterizing instrument (e.g., a heated element) or a therapeutic energy emission point (e.g., ultrasonic, laser, light) which is positioned on a portion of instrument 4 (e.g., proximal to a distal tip).

Although embodiments of the invention have been described with reference to various embodiments of the present invention and examples with respect to a surgical instrument, it is within the scope and spirit to incorporate or use with any suitable mechanical device. Further, while some aspects and embodiments of the invention have been described with reference to a surgeon as a user, the aspects and embodiments of the present invention may be used with another user, depending on circumstances in which the invention is used.

The foregoing descriptions of specific embodiments have been presented for purposes of illustration and description. They are not intended to be exhaustive or to limit the presented technology to the precise forms disclosed, and obviously many modifications and variations are possible in light of the above teaching. The embodiments were chosen and described in order to best explain the principles of the presented technology and its practical application, to thereby enable others skilled in the art to best utilize the presented technology and various embodiments with various modifications as are suited to the particular use contemplated. Thus, it should be understood that numerous and various modifications may be made without departing from the spirit of embodiments of the invention.

What is claimed is:

1. A remotely controlled surgical device control portion, said control portion comprising:
   a user moveable bi-directional trigger configured for receiving a motion input in opposing first and second directions, said motion input for controlling an articulation motion of an articulating surgical instrument;
   a finger loop disposed within said trigger and configured for receiving said motion input in the form of a user squeezing said trigger in said first direction with at least one finger or pushing said trigger in said second direction with said at least one finger; and
   a flange extending from said trigger and configured such that pushing said flange in said second direction with a thumb pushes the trigger in said second direction.

2. The control portion of claim 1, further comprising:
   a central frame assembly; and
   a grasper handle assembly coupled with said central frame assembly, said grasper handle assembly including said trigger.

3. The control portion of claim 2, wherein said grasper handle assembly further comprises:
   a second finger loop configured to remain immobile in response to a user input via said trigger loop.

4. The control portion of claim 2, wherein said grasper handle assembly further comprises:
   a rotatable arm holder assembly coupled to said central frame assembly.

5. The control portion of claim 2, wherein said grasper handle assembly further comprises:
   a thumbwheel coupled with said grasper handle assembly.

6. The control portion of claim 1, wherein said trigger further comprises:
   an axis about which said trigger is configured to rotate in said first direction in response user input in said first direction and about which said trigger is further configured to rotate about in said second direction in response to user input in said second direction.

7. The control portion of claim 6, further comprising:
   an extension protruding from said axis; and
   a control cylinder coupled with said extension and configured for translating said motion input into a control signal for remotely controlling an articulation motion of an articulating surgical instrument, wherein said control signal comprises a displacement of hydraulic fluid.

8. A remotely controlled surgical device control portion, said control portion comprising:
   a first set of controls for receiving articulating surgical instrument motion inputs in a first plurality of degrees of freedom of movement; and
   a second set of controls coupled with said first set of controls said second set of controls configured for receiving articulating surgical instrument motion inputs in a second plurality of degrees of freedom of movement, said second set of controls comprising:
   a user moveable bi-directional trigger configured for receiving a motion input in opposing first and second directions via one of said second plurality of degrees of freedom of movement, said motion input for controlling an articulation motion of an articulating surgical instrument;
   a finger loop disposed within said trigger and configured for receiving said motion input in the form of a user squeezing said trigger in said first direction with at least one finger or said user pushing said trigger in said second direction with said at least one finger; and
   a flange extending from said trigger and configured such that pushing said flange in said second direction with a thumb pushes the trigger in said second direction.

9. The control portion of claim 8, wherein said first set of controls and said second set of controls are configured to receive said motion inputs in said first and second pluralities of degrees of freedom of movement from a contiguous human shoulder, arm, and hand and to translate received motion inputs into one or more control signals for controlling motion of an articulating surgical instrument.

10. The control portion of claim 9, wherein said second set of controls is configured to generate one or more control signals, and wherein at least one of said one or more control signals comprises a displacement of hydraulic fluid.

11. The control portion of claim 8, wherein said first set of controls comprises:
    a first transmission configured for receiving a motion input in a first degree of freedom;
    a first control cylinder coupled with said first transmission and configured for translating said motion input in said first degree of freedom into a first control signal, wherein said first control signal comprises a displacement of hydraulic fluid;
    a second transmission configured for receiving a motion input in a second degree of freedom;
    a second control cylinder coupled with said second transmission and configured for translating said motion input in said second degree of freedom into a second control signal, wherein said second control signal comprises a displacement of hydraulic fluid;
    a third transmission configured for receiving a motion input in a third degree of freedom; and
    a third control cylinder coupled with said third transmission and configured for translating said motion input in said third degree of freedom into a third control signal, wherein said third control signal comprises a displacement of hydraulic fluid.

12. The control portion of claim 8, wherein said second set of controls further comprises:
    a central frame assembly;
    a grasper handle assembly coupled with said central frame assembly, said grasper handle assembly including said user moveable bi-directional trigger; and
    a rotatable thumbwheel coupled with said grasper handle assembly.

13. The control portion of claim 12, further comprising:
    a fourth control cylinder coupled with said thumbwheel and configured for translating a motion input in a fourth degree of freedom into a fourth control signal, wherein said fourth control signal comprises a displacement of hydraulic fluid;
    a fifth control cylinder coupled with said grasper handle assembly and configured for translating a motion input in a fifth degree of freedom into a fifth control signal, wherein said fifth control signal comprises a displacement of hydraulic fluid;
    a sixth control cylinder coupled with said grasper handle assembly and configured for translating a motion input in a sixth degree of freedom into a sixth control signal, wherein said sixth control signal comprises a displacement of hydraulic fluid; and
    a seventh control cylinder coupled with said trigger and configured for translating a motion input in a seventh degree of freedom into a seventh control signal, wherein said seventh control signal comprises a displacement of hydraulic fluid.

14. The control portion of claim 13, wherein said grasper handle assembly comprises:
a plurality of finger loops configured for receiving one or more fingers, wherein at least one of said finger loops is associated with said trigger.

15. The control portion of claim 8, wherein said second set of controls further comprises:
a central frame assembly;
a rotatable arm holder assembly coupled to said central frame assembly; and
a grasper handle assembly coupled with said central frame assembly, said grasper handle assembly including said user moveable bi-directional trigger.

16. The control portion of claim 15, further comprising:
a fourth control cylinder coupled with said arm holder assembly and configured for translating a motion input in a fourth degree of freedom into a fourth control signal, wherein said fourth control signal comprises a displacement of hydraulic fluid.

17. A surgical device for remotely controlling an articulating surgical instrument, said device comprising:
an articulating surgical instrument;
a control portion configured for receiving user inputs in a plurality of degrees of freedom from a human shoulder, arm and hand and translating said user inputs into one or more control signals for controlling motion of said articulating surgical instrument, said control portion comprising:
a user moveable bi-directional trigger;
a finger loop disposed within said trigger and configured for facilitating a user input of squeezing said trigger in a first direction or pushing said trigger in a second direction, said second direction being opposite of said first direction; and
a flange extending from said trigger and configured such that pushing said flange in a second direction pushes the trigger in said second direction; and
a slave portion coupled between said control portion and said articulating surgical instrument, said slave portion configured for moving said articulating surgical instrument in response to said one or more control signals.

18. The device of claim 17, further comprising:
a tool coupled with a distal tip of said articulating surgical instrument.

19. The device of claim 17, wherein said at least one of said one or more control signals comprises a displacement of hydraulic fluid.

20. The device of claim 17, wherein said control portion is configured for remote location from said slave portion and said articulating surgical instrument.

21. The device of claim 17, wherein said control portion comprises:
a first set of controls configured for receiving said motion inputs in first, second, and third degrees of freedom from said human shoulder, arm, and hand and translating one or more of said motion inputs in said first, second, and third degrees of freedom into one or more of said control signals for controlling one or more macro motions of said slave portion of said device; and
a second set of controls configured for receiving motion inputs in fourth, fifth, sixth, and seventh degrees of freedom from said human shoulder, arm, and hand and translating one or more of said motion inputs in said fourth, fifth, sixth, and seventh degrees of freedom into one or more of said control signals for controlling one or more micro motions of said articulating surgical instrument.

22. The device of claim 21, wherein said first set of controls comprises:
a first transmission configured for receiving said motion input in said first degree of freedom;
a first control cylinder coupled with said first transmission and configured for translating said motion input in said first degree of freedom into a first control signal of said control signals, wherein said first control signal comprises a displacement of hydraulic fluid;
a second transmission configured for receiving said motion input in said second degree of freedom;
a second control cylinder coupled with said second transmission and configured for translating said motion input in said second degree of freedom into a second control signal of said control signals, wherein said second control signal comprises a displacement of hydraulic fluid;
a third transmission configured for receiving said motion input in said third degree of freedom; and
a third control cylinder coupled with said third transmission and configured for translating said motion input in said third degree of freedom into a third control signal of said control signals, wherein said third control signal comprises a displacement of hydraulic fluid.

23. The device of claim 22, wherein said second set of controls comprises:
a central frame assembly; and
a grasper handle assembly coupled with said central frame assembly, said grasper handle assembly including said trigger.

24. The device of claim 23, further comprising:
a fourth control cylinder coupled with said a rotatable element of said second set of controls and configured for translating said motion input in said fourth degree of freedom into a fourth control signal of said one or more control signals, wherein said fourth control signal comprises a displacement of hydraulic fluid;
a fifth control cylinder coupled with said grasper handle assembly and configured for translating said motion input in said fifth degree of freedom into a fifth control signal of said one or more control signals, wherein said fifth control signal comprises a displacement of hydraulic fluid;
a sixth control cylinder coupled with said grasper handle assembly and configured for translating said motion input in said sixth degree of freedom into a sixth control signal of said one or more control signals, wherein said sixth control signal comprises a displacement of hydraulic fluid; and
a seventh control cylinder coupled with said trigger and configured for translating said motion input in said seventh degree of freedom into a seventh control signal of said one or more control signals, wherein said seventh control signal comprises a displacement of hydraulic fluid.

25. The device of claim 24, wherein said rotatable element comprises:
a rotatable arm holder assembly coupled to said central frame.

26. The device of claim 24, wherein said rotatable element comprises:
a rotatable thumbwheel coupled with said grasper handle assembly.

* * * * *